(12) United States Patent
Hakonarson et al.

(10) Patent No.: US 12,121,514 B2
(45) Date of Patent: *Oct. 22, 2024

(54) NONSELECTIVE METABOTROPIC GLUTAMATE RECEPTOR ACTIVATORS FOR TREATMENT OF ATTENTION DEFICIT DISORDER AND 22Q SYNDROME

(71) Applicant: THE CHILDREN'S HOSPITAL OF PHILADELPHIA, Philadelphia, PA (US)

(72) Inventors: Hakon Hakonarson, Malvern, PA (US); Charlly Kao, Philadelphia, PA (US)

(73) Assignee: THE CHILDREN'S HOSPITAL OF PHILADELPHIA

( * ) Notice: Subject to any disclaimer, the term of this patent is extended or adjusted under 35 U.S.C. 154(b) by 184 days.

This patent is subject to a terminal disclaimer.

(21) Appl. No.: 17/125,164

(22) Filed: Dec. 17, 2020

(65) Prior Publication Data

US 2021/0205288 A1 Jul. 8, 2021

Related U.S. Application Data

(60) Continuation of application No. 15/850,307, filed on Dec. 21, 2017, now Pat. No. 10,869,861, which is a division of application No. 15/258,828, filed on Sep. 7, 2016, now Pat. No. 9,884,057.

(60) Provisional application No. 62/215,633, filed on Sep. 8, 2015, provisional application No. 62/215,636, filed on Sep. 8, 2015, provisional application No. 62/215,673, filed on Sep. 8, 2015, provisional application No. 62/215,628, filed on Sep. 8, 2015.

(51) Int. Cl.
| | | |
|---|---|---|
| *A61K 31/454* | | (2006.01) |
| *A61K 45/06* | | (2006.01) |
| *C12Q 1/6883* | | (2018.01) |

(52) U.S. Cl.
CPC ............ *A61K 31/454* (2013.01); *A61K 45/06* (2013.01); *C12Q 1/6883* (2013.01); *C12Q 2600/156* (2013.01); *C12Q 2600/158* (2013.01)

(58) Field of Classification Search
CPC .................................................. A61K 31/454
See application file for complete search history.

(56) References Cited

U.S. PATENT DOCUMENTS

| | | | |
|---|---|---|---|
| 9,884,057 B2 | 2/2018 | Hakonarson et al. | |
| 10,869,861 B2 * | 12/2020 | Hakonarson | A61P 25/00 |
| 2004/0116505 A1 | 6/2004 | Krauss et al. | |
| 2005/0233321 A1 | 10/2005 | Hess et al. | |
| 2007/0244152 A1 | 10/2007 | Lowy | |
| 2007/0299113 A1 | 12/2007 | Kalvinsh et al. | |
| 2009/0176740 A1 | 7/2009 | Dauglas | |
| 2010/0120628 A1 | 5/2010 | Belouchi et al. | |
| 2010/0143921 A1 | 6/2010 | Sadee et al. | |
| 2010/0216734 A1 | 8/2010 | Barlow et al. | |
| 2011/0269688 A1 | 11/2011 | Hakonarson et al. | |
| 2012/0149677 A1 | 6/2012 | Dudkin et al. | |
| 2013/0143867 A1 | 6/2013 | Fogel et al. | |
| 2013/0203814 A1 | 8/2013 | Glessner et al. | |
| 2013/0225623 A1 | 8/2013 | Buxbaum et al. | |
| 2014/0303243 A1 | 10/2014 | Hakonarson et al. | |
| 2014/0315992 A1 | 10/2014 | Hakonarson et al. | |
| 2016/0032390 A1 | 2/2016 | Hakonarson et al. | |
| 2017/0083664 A1 | 3/2017 | Hakonarson et al. | |
| 2017/0087139 A1 | 3/2017 | Hakonarson et al. | |
| 2017/0087140 A1 | 3/2017 | Hakonarson et al. | |
| 2017/0087141 A1 | 3/2017 | Hakonarson et al. | |

FOREIGN PATENT DOCUMENTS

| | | |
|---|---|---|
| WO | 2003/054167 A2 | 7/2003 |
| WO | 2005/094801 A1 | 10/2005 |
| WO | 2007/104035 A1 | 9/2007 |
| WO | 2009/105718 A1 | 8/2009 |
| WO | 2010/057112 A2 | 5/2010 |
| WO | 2012/027491 A1 | 3/2012 |
| WO | 2013/006857 A1 | 1/2013 |
| WO | 2016/022324 A1 | 2/2016 |
| WO | 2016/205348 A1 | 12/2016 |
| WO | 2008/136995 A1 | 11/2018 |

OTHER PUBLICATIONS

Santa Cruz Biotechnology. "mGluR-3 activators." Accessed Dec. 9, 2021. Available on: < www.scbt.com/browse/chemicals-Protein-Interacting-Inhibitors-Activators-Substrates-Protein-Activators-mGluR-3-Activators/_/N-xni6r1/>/>. (Year: 2021).*
Clinical Trials.gov Identifier: NCT02286817, Posted Nov. 10, 2014, https://clinicaltrials.gov/ct2/history/NCT02286817?A=1&B=1&C=merged, accessed Aug. 5, 2018. (Year: 2014).*
Nature Communications, published Jan. 16, 2018, 9 (4), 1-9, accessed Aug. 5, 2018. (Year: 2018).*
Castro, Adriana, et al. "ADHD and genetic syndromes." Brain and Development. (2011), vol. 33, pp. 456-461, accessed Aug. 5, 2018. (Year: 2011).*
Simon, T., et al. "22q11.2 microdeletions: linking DNA structural variation to brain dysfunction and schizophrenia." Nature. (Jun. 2010), vol. 11, pp. 402-416. (Year: 2010).*
Hamilton, S. Sutton, et al. "Oppositional Defiant Disorder." American Family Physician. (Oct. 1, 2008), vol. 78, No. 7, pp. 861-866. (Year: 2008).*

(Continued)

*Primary Examiner* — John S Kenyon
(74) *Attorney, Agent, or Firm* — Howson & Howson, LLP; Kathleen D. Rigaut; Richard F. Kane

(57) ABSTRACT

This application relates to methods of treating attention deficit hyperactivity disorder (ADHD), 22q deletion and/or duplication syndrome, and co-morbidities with a nonselective activator of metabotropic glutamate receptors, such as fasoracetam, for example, in subjects having a genetic alteration in at least one metabotropic glutamate receptor (mGluR) network gene.

18 Claims, 52 Drawing Sheets

(56) References Cited

OTHER PUBLICATIONS

Wang, K. et al., "PennCNV: An integrated hidden Markov model designed for high-resolution copy number variation detection in whole-genome SNP genotyping data," Genome Res. 17(11):1665-74 (2007).
Wang, K. et al., "Copy Number Variation Detection via High-Density SNP Genotyping," Cold Spring Harb Proloc. (2008).
Waschbusch, D.A. and Elgar, F. J., "Development and Validation of the Conduct Disorder Rating Scale," Assessmenl 14(1): 65-74 (2007).
Wigal, S. B. et al., "NWP06, an Extended-Release Oral Suspension of Methylphenidate, Improved Attention-Deficit/Hyperactivity Disorder Symptoms Compared with Placebo in a Laboratory Classroom Study," Journal of Child and Adolescent Psychopharmacology, 23(1):3-10 (2013).
Fasoracetam: LAM 105, NS 105, Drugs R&D, 2(2): 135-136 (1999).
Bloch, Michael et al., "Recent advances in Tourette syndrome," Current Opinion in Neurology, 24(2):119-125 (2011).
Caporino et al., "Defining Treatment Response and Remission in Child Anxiety: Signal Detection Analysis Using Pediatric Anxiety Rating Scale," J Am Acad Child Adolesc Psychiatry, 52(1):57-67 (2013).
Cohen, S. et al., "Clinical Assessment of Tourette Syndrome and Tic Disorders," Neurosci Biobehavb Rev., 37(6):997-1007 (2013).
Declaration of Hakon Hakonarson, MD, PhD dated Apr. 12, 2018, filed Apr. 16, 2018 in U.S. Appl. No. 15/258,969.
Declaration of Hakon Hakonarson, MD, PhD dated Apr. 12, 2018, filed Apr. 16, 2018 in U.S. Appl. No. 15/258,977.
Declaration of Hakon Hakonarson, MD, PhD dated Mar. 8, 2017, filed in Australian Appl. No. AU2011293363.
Dietrich, Andrea et al., "The Tourette International Collaborative Genetics (TIC Genetics) study, finding the genes causing Tourette syndrome: objectives and methods," European Child and Adolescent Psychiatry, 24(2):141-151 (2014).
Ebell, M. H., "Diagnosis of Anxiety Disorders in Primary Care," Am Fam Physician, 78(4):501-502 (2008).
Clinical Trials.gov Identifier: NCT02286817, Posted Nov. 10, 2014, https://clinicaltrials.gov/ct2/history/NCT02286817?A=1&B=1&C=merged, accessed Aug. 5, 2018.
Ercan, E. S. et al., "Risperidone in the treatment of conduct disorder in preschool children without intellectual disability," Child and Adolescent Psychiatry and Mental Health, 5:10 (2011).
Fistova et al., "Study specific effects of nootropic drugs on glutamate receptors in the rat brain," Eksp Klin Farmakol. 74 (1):abstract (2011).
Gasparini et al., "Allosteric Modulators for mGlu Receptors," Current Neuropharmacology, 5:187-194 (2007).
Gerevich, J. et al., "The generalizability of the Buss-Perry Aggression Questionnaire," Int J Methods Psychiatr. Res., 16 (3):124-136 (2007).
Gregory, Karen J. et al., "Pharmacology of metabotropic glutamate receptor allosteric modulators: structural basis and therapeutics potential for CNS disorders," Progress in Molecular Biology and Translational Science, 115: 61-121 (2013).
Gualtieri et al., "Design and Study of Piracetam-like Nootropics, Controversial Members of the Problematic Class of Cognition-Enhancing Drugs," Current Pharmaceutical Design, 8:125-138 (2002).
Hadley et al., "The impact of metabotropic glutamate receptor and other gene family interaction networks on autism," Nature Communications, 5:4074 (2014).
Halperin, J. et al. "Reliability, Validity, and Preliminary Normative Data for the Children's Aggression Scale-Teacher Version," J Am Acad Child Adolesc Psychiatry, 42(8):965-971 (2003).
Hamelin and Lehmann, "Effects of putative cognition enhancers on the NMDA receptor by [3H]MK801 binding," European Journal of Pharmacology 281: R11-R13 (1995).

Hellings et al., "The Overt Aggression Scale for Rating Aggression in Outpatient Youth with Autistic Disorder: Preliminary Findings," J of Neuropsychiatry and Clinical Neurosciences, 17:29-35 (2005).
Henrichsen et al., "Copy number variants, diseases and gene expression," Human Molecular Genetics 18(1):R1-R8 (2009).
Hirouchi et al., "Role of metabotropic glutamate receptor subclasses in modulation of adenylyl cyclase activity by a nootropic NS-105," European Journal of Pharmacology, 387:9-17 (2000).
Hodgins et al., "Adolescents with conduct disorder: does anxiety make a difference?," The J. of Forensic Psychiatric and Psychology (2011), vol. 22(5), pp. 669-691.
International Search Report and International Written Opinion for PCT/US2016/037596, dated Sep. 16, 2016.
International Search Report and Written Opinion issued in PCT/US2016/050573 dated Dec. 21, 2016.
International Search Report and Written Opinion issued in PCT/US2016/050580 on Dec. 20, 2016.
International Search Report and Written Opinion issued in PCT/US2016/050581 dated Dec. 21, 2016.
James, A. C., "Prescribing antipsychotics for children and adolescents," Advances in psychiatric treatment, 16:63-75 (2010).
Kelleher III et al., "High-Throughput Sequencing of mGluR Signaling Pathway Genes Reveals Enrichment of Rare Variants in Autism," PLoS One, 7(4):e35003 (2012).
Kendler, Kenneth S. et al., "Familial Influences on Conduct Disorder Reflect 2 Genetic Factors and 1 Shared Environmental Factor," JAMA Psychiatry, 70(1): 78.
Miller, Caroline, "How Anxiety Leads to Disruptive Behavior: kids who seem oppositional are often severely anxious," Child Mind Institute: Anxiety and Disruptive Behavior in Children, pp. 1-3. https://childmind.org/article/how-anxiety-leads-to-disruptive-behavior/) visited Nov. 27, 2017.
National Institute of Mental Health, "Anxiety Disorder," NIH Publication No. 09 3879 (2009).
Navarro, J.F. et al., "P.1.d.006 Effects of LY379268, a selective agonist of mGlu2/3 receptors, on isolation-induced aggression in male mice," European Neuropsychopharmacology, 18:S252 (2008).
Niswender, C.M. and Conn, P.J., "Metabotropic Glutamate Receptors: Physiology, Pharmacology and Disease," Ann. Rev. Pharmacol. Toxicol. 50:295-322 (2010).
Nock, M. K. et al., "Prevalence, Subtypes, and Correlates of DSM-IV Conduct Disorder in the National Comorbidity Survey Replication," Psychol Med., 36(5):699-710 (2006).
Nomura and Nishizaki, "Nefiracetam facilitates hippocampal neurotransmission by a mechanism independent of the piracetam and aniracetam action," Brain Research, 870: 157-162 (2000).
Ogasawara et al., "Involvement of Cholinergic and GABAergic Systems in the Reversal of Memory Disruption by NS-105, a Cognition Enhancer," Pharmacology Biochemistry and Behavior, 64(1):41-52 (1999).
Oka et al., "A novel cognition enhancer NS-105 modulates adenylate cyclase activity through metabotropic glutamate receptors in primary neuronal culture," Nauny-Schmiedeberg's Arch Pharmacol, 356:189-196 (1997).
Oka, M. et al., "Involvement of metabotropic glutamate receptors in Gi- and Gs-dependent modulation of adenylate cyclase activity induced by a novel cognition enhancer NS-105 in rat brain," Brain Research, 754: 121-130 (1997).
Palucha, et al., "Metabotropic glutamate receptor ligands as possible anxiolytic and antidepressant drug," Pharmacology and Therapeutics, 115(1):116-147 (2007).
Sansone, S. et al., "Psychometric Study of the Aberrant Behavior Checklist in Fragile X Syndrome and Implications or Targeted Treatment," J Autism Dev Disord, 42(7):1377-1392 (2012).
Shannon, P. et al., "Cytoscape: A Software Environment for Integrated Models of Bimolecular Interaction Networks," Genome Res. 13(11):2498-504 (2003).
Shimidzu, Takako et al., "Effect of a novel cognition enhancer NS-105 on learned helplessness in rats: Possible Involvement of GABAB receptor up-regulation after repeated treatment," European Journal of Pharmacology, 338(3):225-232 (1997).

(56) References Cited

OTHER PUBLICATIONS

Singer, H.S. et al., "Baclofen treatment in Tourette syndrome: A double-blind placebo-controlled, crossover trial," Neurology, 56(5):599-604 (2001).
Toteja, N. et al., "Prevalence and correlates of antipsychotic polypharmacy in children and adolescents receiving antipsychotic treatment," Int J Neuropsychopharmacol., 17(7):1095-1105 (2014).
U.S. Dept of Health and Human Services: Public Health Service, "Tourette Syndrome," NIH Publication No. 12-2163 (2012).
Van Ameringen, M. et al., "Anticonvulsants in Anxiety Disorders," CPA-Bull. de l'APC (2003) pp. 9-13.
Waschbusch, D. A. et al., "Development and Validation of the Conduct Disorder Rating Scale," Assessment, 14(1):65-74 (2007).
Winblad, "Piracetam: A Review of Pharmacological Properties and Clinical Uses," CNS Drug Reviews, 11(2):169-182 (2005).
Winnicka et al., "Piracetam—An Old Drug with Novel Properties?," Acta Poloniae Pharmaceutica—Drug Research, 62(5):405-409 (2005).
Wittman, Marion et al., "Activation of Group III mGluRs Inhibits GABergic and Glutamatergic Transmission in Substantia Nigra Pars Reticulata," Journal of Neurophysiology, 1960-1968 (2001).
Zavadenko et al., "Atomoxetine and piracetam in the treatment of attention deficit hyperactivity disorder in children," ZH Nevrol Psikhiatr IM S S Korsakova, 108(7):abstract (2008).
Addington, A. et al., "Annual Research Review: Impact of advances in genetics in understanding developmental psychopathology," J. Child Psychol. Psychiast, (2012) vol. 53(5) 510-518.
Auerbach, B. D. et al., "Mutations causing syndromic autism define an axis of synaptic pathophysiology," Nature, 480 (7375):63-8 (2011).
Clarke, R. A. et al., "Tourette Syndrome and Klippel-Feil Anomaly in a Child with Chromosome 22q11 Duplication," (2009) Case Reports in Medicine vol. ID 361518 pp. 1-5.
Cooper, G. M. et al., "Systematic assessment of copy number variant detection via genome-wide SNP genotyping," nature genetics 2008, 40(10):1199-1203.
Children's Hospital, "22q 11.2 Deletion Syndrome," (Aug. 14, 2010). Accessed Aug. 13, 2019. Available from: <https://www.stlouischildrens.org/conditions-treatments/22q112-deletion-syndrome>.
Fewtrell, MS et al., "Hirschsprung's disease associated with a deletion of chromosome 10 (q11.2q21.2): a further link with neurocristopathies?," J Med Genet 1994: 31:325-327.
Jarrett, M. A. et al., "A conceptual review of the comorbidity of attention-deficit/hyperactivity disorder and anxiety: Implications for future research and practice," Clinical Psychology Review, 28:1266-1280 (2008).
Jones, G. et al., "Exploratory dose-escalation study of NFC-1 in ADHD adolescents with glutamatergic gene network variants," 62nd Annual Meeting AACAP, 2015, poster.
Office Action issued in Canadian Application No. 2,807,505 on May 7, 2018.
Rizzo et al., "Clinical Pharmacology of Comorbid Attention Deficit Hyperactivity Disorder in Tourette Syndrome," Int. Rev. Neurobiol, Chapter 14, vol. 112, 415-444 (2013).
Turgay, A., "Treatment of Comorbidity in Conduct Disorder with Attention-Deficit Hyperactivity Disorder (ADHD)," Essent. Psychopharmacol., 6(5):277-290 (2005).
Childress, A. et al., "Current Investigational Drugs for the Treatment of Attention-Deficit/Hyperactivity Disorder," Expert Opinion on Investigational Drugs, 2016, vol. 25(4):463-474.
Karayiorgou, M. et al., "22q11.2 microdeletions: linking DNA structural variation to brain dysfunction and schizophrenia," Nature Reviews—Neuroscience, 2010, vol. 11:402-416.
Aevi Genomic Medicine, "Aevi Genomic Medicine Announces Top-Line Results from Placebo-Controlled Ascend Trial (Parts A & B) of AEVI-001 in Children with ADHD," New Release, https://aevigenomicmedicine.gcs-web.com/news-releases/news-release-details/aevi-genomic-medicine-announces-top-line-results-placebo, Jan. 2, 2019.

Simon, T. et al., "22q11.2 microdeletions: linking DNA structural variation to brain dysfunction and schizophrenia," Nature, vol. 11, 2010, pp. 402-416.
"Fasoracetam Review—Its Effects, Dosage, Benefits, and Risks," Nootropics Review Nerd (Aug. 13, 2019). Accessed Aug. 10, 2020. Available from: <https://nootropicsreviewnerd.com/fasoracetam/>.
Niklasson, Lena et al., "Autism, ADHD, mental retardation and behavior problems in 100 individuals with 22q11 deletion syndrome," Research in Developmental Disabilities, vol. 30, No. 4, 2009, pp. 763-773.
Newcorn J.H., et al., "Symptom profiles in children with ADHD: effects of comorbidity and gender," Journal of the American Academy of Child and Adolescent Psychiatry, vol. 40, No. 2, 2001, pp. 137-146.
U.S. National Library of Medicine, "Phase I Single Dose, Open-Label Pharmacokinetic Study and Single-Blind, Placebo-Controlled Dose Escalation Study of NFC-1 in Adolescents With Attention Deficit Hyperactivity Disorder (NFC1-GREAT)," Clinical Trials.gov Identifier: NCT02286817, 2014.
Lo-Castro, Adriana et al., "ADHD and genetic syndromes," Brain and Development, vol. 33, 2011, pp. 456-461.
Elia, Josephine et al., "Fasoracetam in adolescents with ADHD and glutamatergic gene network variants disrupting mGluR neurotransmitter signaling," Nature Communications, vol. 9, No. 4, 2018, pp. 1-9.
Akhundian, J., "Effect of Piracetam on attention deficit and hyperactivity disorder," Iranian Journal of Pediatrics, 2001, 11(2): 32-36; abstract only.
Akutagava-Martins et al., Glutamatergic Copy Number Variants and Their Role in Attention-Deficit/Hyperactivity Disorder, Am J Med Genet Part B. 165B:502-509 (2014).
Aman, M.G., "Annotated Biography on the Aberrant Behavior Checklist (ABC)," Unpublished Manuscript. Columbus, OH: The Ohio State University (2010).
Baker, K. and Vorstman, J., "Is there a core neuropsychiatric phenotype in 22q11.2 deletion syndrome," Curr Opin Neurol, 25:131-137 (2012).
Cokum, P., "Actigraphy and Parental Ratings of Sleep in Children with Attention-Deficit/Hyperactivity Disorder (ADHD)," Sleep, 24(3):303-312 (2001).
Database Geo [online] NCBI, "Illumina HumanHap550 Genotyping Beadchip v1," Feb. 5, 2008, XP002717448.
Elia, et al., "Genome-wide copy number variation study associates metabotropic glutamate receptor gene networks, with attention deficit hyperactivity disorder," Nat Genet., 44(1):78-84 (2011).
Elia, J. et al., "Rare Structural Variants Found in Attention-Deficit Hyperactivity Disorder are Preferentially Associated with Neurodevelopmental Genes," Molecular Psychiatry, 2010, 15(6): 637-646, and supplementary table s1 (p. 1-7).
Extended European Search Report in copending European Patent Application No. 11820610.1, dated Jan. 2, 2014.
File history for U.S. Appl. No. 13/776,662, filed Feb. 25, 2013.
Firth, H. V., "22q11.2 Duplication," Gene Reviews—NCBI Bookshelf (2013).
Forero, D. et al., "Candidate Genes Involved in Neural Plasticity and the Risk for Attention-Deficit Hyperactivity Disorder: a Meta-Analysis of 8 Common Variants," Journal of Psychiatry and Neuroscience, 2009, 34(5): 361-366.
Forkmann, T. et al., "The clinical global impression scale and the influence of patient or staff perspective on butcome," BMC Psychiatry, 11 :83 (2011).
Gerevich, J. et al., "The generalizability of the Buss-Perry Aggression Questionnaire," Int. J. Meth. Psychiatr. Res. 16(3): 124-136 (2007).
Ghelardini et al., "DM235 (Sunifiram): a Novel Nootropic with Potential as a Cognitive Enhancer," Naunyn-Schmiedeberg's Archives of Pharmacology, 365:419-426 (2002).
Goodman et al., "Interpreting ADHS Rating Scale Scores: Linking ADHD Rating Scale Scores and CGI Levels in Two Randomized Controlled Trials of Lisdexamfetamine Dimesylate in ADHD," Primary Psychiatry, 17(3):44-52 (2010).

(56) References Cited

OTHER PUBLICATIONS

Hadley, D. et al., "The impact of the metabotropic glutamate receptor and other gene family interaction networks on autism," Nature Communications, 5:4074 (2014).
Halperin, J.M., et al., "Reliability, Validity, and Preliminary Normative Data for the Children's Aggression Scale-Teacher Version," J. Am. Acad. Child Adolesc. Psychiatry 42(8): 965-971 (2003).
Harty, S.C. et al., "Adolescents with Childhood ADHD and Comorbid Disruptive Behavior Disorders: Aggression, Anger, and Hostility," Child Psychiatry Hum. Dev. 40(1): 85-97 (2009).
Hellings, J.A. et al., "The Overt Aggression Scale for Rating Aggression in Outpatient Youth with Autistic Disorder: Preliminary Findings," J. Neuropsychiatry Clin. Neurosci. 17: 29-35 (2005).
Hidalgo et al., "An effect-size analysis of pharmacologic treatments for generalized anxiety disorder," Journal of Psychopharmacology, 21 (8):864-872 (2007).
Hirouchi, Masaaki, "Role of metabotropic glutamate receptor subclasses in modulation of adenylyl cyclase activity by a nootropic NS-105," European Journal of Pharmacology 387: 9-17 (2009).
International Search Report and Written Opinion issued in PCT/US2016/050559 dated Feb. 16, 2017.
International Search Report for PCT/US2011/048993, dated Jan. 27, 2012.
Jonas et al., "The 22q11.2 Deletion Syndrome as a Window into Complex Neuropsychiatric Disorders Over the Lifespan," Biol Psychiatry, 75(5):351-360 (2014).
Kam, H.J. et al. "High-Resolution Actigraphic Analysis of ADHD: A Wide Range of Movement Variability Observation in Three School Courses—A Pilot Study," Health Inform Res, 17(1):29-37 (2011).
Klopocki et al., "Copy-Number Variations, Noncoding Sequences, and Human Phenotypes," Annual Review Genomics Human Genetics, 2011, 12:53-72.
Krom, M. et al., "A Common Variant in DRD3 Receptor is Associated with Autism Spectrum Disorder," Biological Psychiatry, 2009, 65(7): 625-630.
Leigh, M. et al., "A Randomized Double-Blind, Placebo-Controlled Trial of Minocycline in Children and Adolescents , With Fragile X Syndrome," J. Dev Behav Pediatr, 34(3):147-155 (2013).
Malykh, Andrei G. et al., "Piracetam and piracetam-like drugs: from basic science to novel clinical application to CNS disorders," Drugs, 70(3): 287-312 (2010).
Manning, M. et al., "Array-based technology and recommendations for utilization in medical genetics practice for detection of chromosomal abnormalities," Genetics in Medicine, 12(11):742-745 (2010).
Murck, et al., "Taking Personalized Medicine Seriously:Biomarker Approaches in Phase IIb/III Studies in Major Depression and Schizophrenia," Innov clin Neurosci 12(3-4 Suppl A):26S-40S (2015).
Nagamitsu, S. et al., "Upregulated GABA inhibitory function in ADHD children with child behavior checklist—dysregulation profile: 123I-iomazenil SPECT study," Frontiers in Psychiatry 6: 84 (Jun. 2015).
Neale, B. et al., "Genome-Wide Association Scan of Attention Deficit Hyperactivity Disorder," American Journal of Medical Genetics Part B: Neuropsychiatric Genetics, 2008, vol. 147B, pp. 1337-1344.
O'Connor et al., "Metabotropic Glutamate Receptor 7: At the Interface of Cognition and Emotion," Eur J Pharacol. Apr. 2, 2010;639: 123-131 [Abstract].
Park, S. et al., "Association between the GRM7 rs3792452 polymorphism and attention deficit hyperactivity disorder in a Korean sample," Behavioral and Brain Functions, 9:1 (2013).
Park, S. et al., "The Metabotropic Glutamate Receptor Subtype 7 rw 3792452 Polymorphism is Associated with the Response to Methylphenidate in Children with Attention-Deficit/Hyperactivity Disorder," J. Child Adolesc. Phychopharmacology 24(4): 223-227 (2014).
Prosecution History of U.S. Appl. No. 13/108,652.
Prosecution History of U.S. Appl. No. 14/131,359.
Prosecution History of U.S. Appl. No. 14/292,480.
Schneider, M. et al., "Psychiatric Disorders From Childhood to Adulthood in 22q11.2 Deletion Syndrome: Results from the International Consortium on Brain Behavior in 22q11.2 Deletion Syndrome," Am J. Psychiatry 171(6):627-639 (2014).
Semenova et al., "The Effects of the mGluR5 Antagonist MPRP and the mGluR2/3 Antagonist LY341495 on Rats' Performance in the 5-choice Serial Reaction Time Task," Neuropharmacology, 2007, 52(3):863-872 [Abstract].
Shaffer, L. et al., "American College of Medical Genetics guideline on the cytogenetic evaluation of the individual with the developmental delay or mental retardation," Genetics in Medicine, 7(9):650-654 (2005).
Steele, et al., "Remission Versus Response as the Goal of Therapy in ADHD: A New Standard for the Field?," Clinical Therapeutics, 28(11): 1892-1908 (2006).
Stofanko, M. et al., "Simple, Rapid and Inexpensive Quantitative Fluorescent PCT Method for Detection of Microdeletion and Microduplication Syndromes," Plos One, 8(4): e61328 (2013).
Tarver, J. et al., "Attention deficit hyperactivity disorder (ADHD): an updated review of the essential facts," Child: Care, Health and Development, 40(6):762-774 (2014).
The Research Unit on Pediatric Psychopharmacology Anxiety Stud Group, "Fluvoxamine for the Treatment of Anxiety Disorders in Children and Adolescents," N Engl J Med, vol. 344(17):1279-1285 (2001).

\* cited by examiner

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| ACAT1 | chr11:107992257-108018891 | chr11:107492257-108518891 | chr11:107497467-107523485 | rs7925970 | kgp3957860 |
| ACCN1 | chr17:31340105-32483825 | chr17:30840105-32983825 | chr17:28364218-29507938 | rs2519865 | kgp10854156 |
| ACTR2 | chr2:65454828-65498390 | chr2:64954828-65998390 | chr2:65308405-65351891 | rs1477043 | kgp4266233 |
| ADCY1 | chr7:45614124-45762714 | chr7:45114124-46262714 | chr7:45580649-45729239 | rs2289367 | kgp13398740 |
| ADRBK1 | chr11:67033904-67054029 | chr11:66533904-67554029 | chr11:66790480-66810605 | kgp7862175 | kgp2126040 |
| ALDOA | chr16:30064410-30081741 | chr16:29564410-30581741 | chr16:29971972-29989236 | kgp733881 | kgp6386467,rs33997546 |
| APP | chr21:27252860-27543446 | chr21:26752860-28043446 | chr21:26174731-26465003 | rs7281883 | kgp2004872 |
| ARL15 | chr5:53180613-53606403 | chr5:52680613-54106403 | chr5:53216370-53642160 | kgp10474479 | rs10058571 |
| ATXN7L3 | chr17:42269172-42275529 | chr17:41769172-42775529 | chr17:39624698-39631055 | rs11650560 | rs6503398 |
| BDKRB2 | chr14:96671134-96710666 | chr14:96171134-97210666 | chr14:95740887-95780419 | kgp19731302 | kgp1905230 |
| CA8 | chr8:61101422-61193954 | chr8:60601422-61693954 | chr8:61263976-61356508 | kgp9568230 | kgp1623935 |
| CACNA1B | chr9:140772240-141019076 | chr9:140272240-141519076 | chr9:139892061-140136452 | kgp18327422 | kgp12374930 |
| CACYBP | chr1:174968570-174981163 | chr1:174468570-175481163 | chr1:173235193-173247786 | rs1013769 | kgp15391194 |
| CALM1 | chr14:90863326-90874619 | chr14:90363326-91374619 | chr14:89933125-89944363 | kgp828819 | kgp22766175 |
| CHRM3 | chr1:239549864-240049896 | chr1:239049864-240549896 | chr1:237616487-238116519 | kgp1999037 | rs1537850 |
| CIC | chr19:42788816-42799949 | chr19:42288816-43299949 | chr19:47480656-47491789 | kgp21495548 | kgp22794755 |
| CNP | chr17:40118758-40129754 | chr17:39618758-40629754 | chr17:37372284-37383280 | kgp4988562 | kgp1573374 |

*Fig. 1-1*

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| CNTN4 | chr3:2140549-3099645 | chr3:1640549-3599645 | chr3:2117246-3074645 | kgp7465125 | kgp11488181,rs9811783 |
| CRHR1 | chr17:954314-1170453 | chr17:454314-1670453 | chr17:41217448-41268973 | kgp12243700 | kgp2967880 |
| CTNNA2 | chr2:79412356-80875988 | chr2:78912356-81375988 | chr2:79265864-80729416 | kgp2692843 | kgp6161954 |
| DISC1 | chr1:231664398-232177019 | chr1:231164398-232677019 | chr1:229829183-230243641 | kgp15830047 | kgp10247084 |
| DPP6 | chr7:153584418-154685995 | chr7:153084418-155185995 | chr7:153215351-154316928 | rs1822707 | rs7781545 |
| DYNLL1 | chr12:120907659-120936298 | chr12:120407659-121436298 | chr12:119392042-119420681 | rs2393569 | rs1169303 |
| FPR1 | chr19:52249022-52255150 | chr19:51749022-52755150 | chr19:56940837-56946962 | rs11084062 | kgp21351572 |
| GAPDH | chr12:6643656-6647536 | chr12:6143656-7147536 | chr12:6513917-6517797 | kgp12277967 | kgp3951989 |
| GNA15 | chr19:3136190-3163766 | chr19:2636190-3663766 | chr19:3087190-3114766 | kgp9441497 | rs8109485 |
| GNAI2 | chr3:50263723-50296786 | chr3:49763723-50796786 | chr3:50238727-50271790 | rs1049256 | kgp1163947 |
| GNAO1 | chr16:56225250-56391356 | chr16:55725250-56891356 | chr16:54782751-54948857 | rs36013 | kgp16402238 |
| GNAQ | chr9:80335190-80646219 | chr9:79835190-81146219 | chr9:79525010-79836012 | rs3802497 | kgp478959 |
| GRIK1 | chr21:30909253-31312282 | chr21:30409253-31812282 | chr21:29831124-30234153 | kgp6759057 | kgp13183414 |
| GRIK3 | chr1:37261127-37499844 | chr1:36761127-37999844 | chr1:37033714-37272431 | kgp15160339 | kgp6185747 |
| GRM1 | chr6:146348781-146758731 | chr6:145848781-147258731 | chr6:146390474-146800424 | kgp17333275 | rs17076442 |
| GRM3 | chr7:86273229-86494192 | chr7:85773229-86994192 | chr7:86111165-86332128 | rs7809507 | rs6950721 |
| GRM5 | chr11:88237743-88796816 | chr11:87737743-89296816 | chr11:87881005-88436464 | kgp11022062 | rs7123374 |
| GRM7 | chr3:6902801-7783218 | chr3:6402801-8283218 | chr3:6877926-7758217 | rs17288121 | kgp10770379 |
| GRM8 | chr7:126078651-126893147 | chr7:125578651-127393147 | chr7:125865887-126680383 | rs11767202 | kgp13721602 |
| GSN | chr9:123963760-124095120 | chr9:123463760-124595120 | chr9:123003581-123134941 | rs10984984 | kgp10246924 |
| HOMER1 | chr5:78669785-78809700 | chr5:78169785-79309700 | chr5:78705541-78845456 | kgp22480767 | rs2438612 |

*Fig. 1-2*

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| HTR2A | chr13:47407512-47471169 | chr13:46907512-47971169 | chr13:46305513-46368995 | rs4942513 | rs2185411 |
| LARP7 | chr4:113558119-113578742 | chr4:113058119-114078742 | chr4:113777568-113798191 | kgp20778198 | rs10516593 |
| MAPK1 | chr22:22113946-22221970 | chr22:21613946-22721970 | chr22:20443946-20551970 | rs2019503 | rs5758017 |
| MTHFD1 | chr14:64854758-64926725 | chr14:64354758-65426725 | chr14:63924845-63996474 | kgp8236539 | kgp19721535 |
| MX1 | chr21:42792519-42831141 | chr21:42292519-43331141 | chr21:41714311-41753008 | rs7280789 | kgp9356591 |
| NARG1 | chr4:140222675-140311935 | chr4:139722675-140811935 | chr4:140442125-140531385 | kgp951257 | kgp22761518 |
| NEGR1 | chr1:71868624-72748405 | chr1:71368624-73248405 | chr1:71641212-72520993 | kgp15840593 | kgp15187386 |
| NLN | chr5:65018022-65125111 | chr5:64518022-65625111 | chr5:65053840-65155145 | kgp8540617 | kgp6780911 |
| NMI | chr2:152126981-152146430 | chr2:151626981-152646430 | chr2:151835227-151854676 | rs9789673 | rs4303715 |
| PCBP3 | chr21:47063682-47355618 | chr21:46563682-47855618 | chr21:45888110-46180046 | rs13047590 | rs17371795 |
| PDE1C | chr7:31792631-32338383 | chr7:31292631-32838383 | chr7:31759156-32305466 | rs960434 | rs10264489 |
| PPP2R1A | chr19:52693054-52729678 | chr19:52193054-53229678 | chr19:57385045-57421483 | kgp3827878 | kgp21490256 |
| PRPSAP1 | chr17:74306867-74350279 | chr17:73806867-74850279 | chr17:71818609-71861526 | kgp13936725 | kgp5222426 |
| PSMD11 | chr17:30771501-30808042 | chr17:30271501-31308042 | chr17:27795614-27832155 | kgp12010810 | rs8065019 |
| PSMD13 | chr11:236807-252984 | chr11:1-752984 | chr11:226807-242984 | kgp9815230 | kgp7252222 |
| PXN | chr12:120648241-120703574 | chr12:120148241-121203574 | chr12:119132632-119187946 | kgp9790305 | kgp10851563 |
| QRICH2 | chr17:74270129-74303761 | chr17:73770129-74803761 | chr17:71781724-71815356 | kgp9494493 | kgp13978344 |
| RANBP1 | chr22:20105023-20114706 | chr22:19605023-20614706 | chr22:18485023-18494704 | kgp15081773 | kgp240898 |
| RAP2A | chr13:98086474-98120252 | chr13:97586474-98620252 | chr13:96884476-96918245 | kgp1964422 | kgp12456635 |
| RCC1 | chr1:28832454-28865708 | chr1:28332454-29365708 | chr1:28717331-28738194 | kgp4972332 | kgp10549261 |
| RGS12 | chr4:3315873-3441640 | chr4:2815873-3941640 | chr4:3285671-3411438 | kgp6603457 | kgp12100218 |

*Fig. 1-3*

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| RIF1 | chr2:152266396-152333860 | chr2:151766396-152833860 | chr2:151974645-152040665 | rs13010870 | kgp14366130 |
| RUVBL2 | chr19:49497155-49519182 | chr19:48997155-50019182 | chr19:54188967-54210994 | kgp2866116 | rs6509434 |
| RYR1 | chr19:38924339-39078204 | chr19:38424339-39578204 | chr19:43616179-43770044 | kgp21463042 | kgp10827233 |
| RYR2 | chr1:237205701-237997288 | chr1:236705701-238497288 | chr1:235272324-236063911 | kgp15265824 | kgp855991 |
| SDC3 | chr1:31342312-31381480 | chr1:30842312-31881480 | chr1:31114899-31154067 | kgp3545961 | rs1039630 |
| SELE | chr1:169691780-169703220 | chr1:169191780-170203220 | chr1:167958404-167969844 | kgp11738441 | kgp5736867 |
| SERPINB9 | chr6:2887503-2903545 | chr6:2387503-3403545 | chr6:2832502-2848506 | rs4959652 | kgp9198993 |
| SETD4 | chr21:37415981-37451687 | chr21:36915981-37951687 | chr21:36337851-36373557 | rs8131794 | kgp10193814 |
| SGTB | chr5:64961754-65017941 | chr5:64461754-65517941 | chr5:64997510-65053697 | rs2367239 | rs253229 |
| SHANK1 | chr19:51165083-51220195 | chr19:50665083-51720195 | chr19:55856895-55912007 | kgp8880890 | kgp5265049 |
| SLC7A10 | chr19:33699569-33716756 | chr19:33199569-34216756 | chr19:38391410-38408548 | kgp3880561 | kgp21532613 |
| SORD | chr15:45315301-45367287 | chr15:44815301-45867287 | chr15:43102632-43154331 | rs3752691 | rs17627219 |
| STRAP | chr12:16035287-16056410 | chr12:15535287-16556410 | chr12:15926554-15947677 | kgp9763258 | kgp18858589 |
| TK1 | chr17:76170159-76183285 | chr17:75670159-76683285 | chr17:73681754-73694880 | kgp13960604 | kgp4569268 |
| TNIK | chr3:170780291-171178197 | chr3:170280291-171678197 | chr3:172264363-172660546 | kgp17660929 | kgp3100328 |
| USP24 | chr1:55532031-55681039 | chr1:55032031-56181039 | chr1:55304619-55453350 | kgp3052862 | kgp5594096 |
| VHL | chr3:10183318-10195354 | chr3:9683318-10695354 | chr3:10158318-10168746 | kgp6652387 | rs9942062 |

*Fig. 1-4*

| Tier 2 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| ACAT2 | chr6:160182988-160200087 | chr6:159682988-160700087 | chr12:51783540-51804590 | kgp17016252 | rs3119312 |
| ACCN2 | chr12:50451486-50477394 | chr12:49951486-50977394 | chr12:48737753-48763661 | kgp6083801 | kgp2326833 |
| ACP1 | chr2:264868-278282 | chr2:1-778282 | chr2:254871-268282 | kgp14878812 | kgp6217001 |
| ACTB | chr7:5566778-5570232 | chr7:5066778-6070232 | chr7:5533304-5536758 | kgp10503129 | rs17136342 |
| ADA | chr20:43248162-43280376 | chr20:42748162-43780376 | chr20:42681576-42713790 | kgp505723 | rs2207199 |
| ADD1 | chr4:2845583-2931802 | chr4:2345583-3431802 | chr4:2815381-2901587 | kgp5601859 | kgp5383382 |
| ADD2 | chr2:70834749-70995375 | chr2:70334749-71495375 | chr2:70688257-70848837 | kgp14188216 | kgp4077094 |
| ADORA1 | chr1:203096835-203136533 | chr1:202596835-203636533 | chr1:201363458-201403156 | rs16850143 | rs12568960 |
| ADRA1B | chr5:159343739-159400017 | chr5:158843739-159900017 | chr5:159276317-159332595 | rs17056747 | kgp2774549 |
| ADRA2A | chr10:112836789-112840662 | chr10:112336789-113340662 | chr10:112826910-112830560 | kgp3219023 | rs10787379 |
| ADRA2C | chr4:3768295-3770253 | chr4:3268295-4270253 | chr4:3737872-3740016 | kgp21189210 | kgp21320659 |
| ADRB2 | chr5:148206155-148208197 | chr5:147706155-148708197 | chr5:148186348-148188381 | kgp6738042 | rs352336 |
| ANXA2 | chr15:60639349-60690185 | chr15:60139349-61190185 | chr15:58426641-58477477 | kgp19904124 | kgp1248561 |
| APTX | chr9:32972603-33001639 | chr9:32472603-33501639 | chr9:32962607-33015110 | kgp8123814 | kgp22778750 |
| AQP1 | chr7:30893009-30965131 | chr7:30393009-31465131 | chr7:30917992-30931656 | kgp13347683 | rs11983505 |
| ARHGAP24 | chr4:86396283-86923823 | chr4:85896283-87423823 | chr4:86615307-87142847 | kgp12192788 | kgp20991115 |
| ARRB1 | chr11:74971165-75062875 | chr11:74471165-75562875 | chr11:74654129-74740521 | kgp13077708 | kgp12867051 |
| ARRB2 | chr17:4613788-4624795 | chr17:4113788-5124795 | chr17:4560537-4571544 | kgp10630047 | rs2304905 |

Fig. 2-1

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| BDKRB1 | chr14:96722546-96731100 | chr14:96222546-97231100 | chr14:95792311-95800853 | rs10146784 | kgp10194056 |
| BTBD2 | chr19:1985446-2015702 | chr19:1485446-2515702 | chr19:1936446-1966702 | kgp9698924 | rs12985186 |
| BTG2 | chr1:203274663-203278729 | chr1:202774663-203778729 | chr1:201541286-201545352 | kgp11073362 | kgp22834576 |
| C17orf44 | chr17:8123966-8127361 | chr17:7623966-8627361 | chr17:8064691-8068086 | kgp14083005 | kgp8066962 |
| C1orf116 | chr1:207191865-207206101 | chr1:206691865-207706101 | chr1:205258488-205272724 | kgp15208593 | rs12094477 |
| C7orf25 | chr7:42948871-42971805 | chr7:42448871-43471805 | chr7:42915396-42938330 | kgp13766903 | kgp8523923 |
| CALB2 | chr16:71392615-71424342 | chr16:70892615-71924342 | chr16:69950126-69981843 | rs1774414 | kgp16319275 |
| CALM2 | chr2:47387220-47403740 | chr2:46887220-47903740 | chr2:47146583-47257154 | kgp12094177 | kgp4237241 |
| CALM3 | chr14:90863326-90874619 | chr14:90363326-91374619 | chr19:51796351-51805879 | kgp828819 | kgp22766175 |
| CAMK1 | chr3:9799028-9811668 | chr3:9299028-10311668 | chr3:9774030-9786661 | kgp4340327 | kgp1318661 |
| CAMK2B | chr7:44256748-44365230 | chr7:43756748-44865230 | chr7:44223273-44331749 | rs10245456 | kgp10338229 |
| CAMK4 | chr5:110559946-110820748 | chr5:110059946-111320748 | chr5:110587980-110848647 | kgp11981357 | kgp22673631 |
| CCNB1 | chr5:68462836-68474070 | chr5:67962836-68974070 | chr5:68498668-68509826 | kgp5100830 | rs28529133 |
| CDC42 | chr1:22379119-22419436 | chr1:21879119-22919436 | chr1:22251706-22292023 | kgp15282552 | rs209696 |
| CENTG1 | chr12:58118076-58135944 | chr12:57618076-58635944 | chr12:56404343-56422211 | kgp22774357 | rs12825103 |
| CHGB | chr20:5891973-5906005 | chr20:5391973-6406005 | chr20:5840167-5854003 | kgp19217529 | kgp5406173 |
| CHP | chr15:41523436-41574083 | chr15:41023436-42074083 | chr15:39310728-39361375 | kgp9389002 | kgp10815429 |
| CHRM2 | chr7:136553398-136701771 | chr7:136053398-137201771 | chr7:136203938-136352311 | rs2882248 | kgp11051162 |
| CMPK | chr2:6988440-7005950 | chr2:6488440-7505950 | chr2:6905891-6923401 | rs16865056 | kgp6717309 |
| CNR1 | chr6:88849584-88875767 | chr6:88349584-89375767 | chr6:88910155-88932281 | kgp11366911 | kgp5424340 |

*Fig. 2-2*

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| COPB2 | chr3:139076432-139108522 | chr3:138576432-139608522 | chr3:140559122-140591212 | kgp17652827 | rs2554152 |
| CYCS | chr7:25158269-25164980 | chr7:24658269-25664980 | chr7:25124799-25131480 | kgp22782658 | kgp9259047 |
| DCN | chr12:91539034-91576806 | chr12:91039034-92076806 | chr12:90063165-90100937 | rs11105720 | rs1602946 |
| DHCR7 | chr11:71145456-71159477 | chr11:70645456-71659477 | chr11:70823104-70837125 | rs2016495 | kgp4157665 |
| DLST | chr14:75348593-75370450 | chr14:74848593-75870450 | chr14:74418371-74440198 | kgp6099186 | rs11621369 |
| DRD2 | chr11:113280316-113346001 | chr11:112780316-113846001 | chr11:112785526-112851211 | kgp12732525 | rs1062613 |
| DRD3 | chr3:113847556-113918254 | chr3:113347556-114418254 | chr3:115330246-115400944 | kgp18078164 | kgp7361746 |
| DSTN | chr20:17550598-17588652 | chr20:17050598-18088652 | chr20:17498598-17536652 | kgp19350858 | rs1581925 |
| ECHS1 | chr10:135175986-135186908 | chr10:134675986-135686908 | chr10:135025979-135036898 | kgp21664075 | kgp22837031 |
| EGFR | chr7:55086724-55275031 | chr7:54586724-55775031 | chr7:55054218-55242525 | kgp12053718 | kgp3314724 |
| EIF3S3 | chr8:117657055-117768062 | chr8:117157055-118268062 | chr8:117726236-117837243 | kgp10576753 | rs1793723 |
| ERBB2 | chr17:37844392-37884915 | chr17:37344392-38384915 | chr17:35097918-35138441 | kgp11528115 | kgp670921 |
| F2R | chr5:76011867-76031595 | chr5:75511867-76531595 | chr5:76047623-76067351 | kgp22518836 | kgp1549629 |
| F2RL2 | chr5:75911306-75919240 | chr5:75411306-76419240 | chr5:75947062-75954996 | kgp10188048 | kgp8041699 |
| F2RL3 | chr19:16999825-17002830 | chr19:16499825-17502830 | chr19:16860825-16863830 | kgp9756004 | kgp12567834 |
| F3 | chr1:94994731-95007413 | chr1:94494731-95507413 | chr1:94767460-94779903 | kgp22732356 | kgp5203715 |
| FKBP3 | chr14:45584801-45604009 | chr14:45084801-46104009 | chr14:44654858-44674272 | kgp8973198 | kgp19724486 |
| FSCN1 | chr7:5632435-5646287 | chr7:5132435-6146287 | chr7:5598979-5612812 | kgp11535801 | kgp22733484 |
| FURIN | chr15:91411884-91426687 | chr15:90911884-91926687 | chr15:89212888-89227691 | kgp19755110 | kgp7570879 |
| FYN | chr6:111981534-112194655 | chr6:111481534-112694655 | chr6:112089177-112301320 | kgp9553033 | kgp10843976 |

*Fig. 2-3*

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| GLP1R | chr6:39016556-39055520 | chr6:38516556-39555520 | chr6:39124534-39163498 | kgp11427391 | kgp8067157 |
| GLP2R | chr17:9729380-9793022 | chr17:9229380-10293022 | chr17:9670105-9733747 | kgp13857921 | kgp14095302 |
| GNAI1 | chr7:79764139-79848725 | chr7:79264139-80348725 | chr7:79602075-79686661 | kgp3340161 | kgp96572 |
| GNAI3 | chr1:110091185-110138452 | chr1:109591185-110638452 | chr1:109892708-109939975 | rs28503409 | kgp2138201 |
| GNB2L1 | chr5:180663927-180670906 | chr5:180163927-181170906 | chr5:180596533-180603512 | kgp9825803 | kgp22785368 |
| GOT1 | chr10:101156626-101190530 | chr10:100656626-101690530 | chr10:101146617-101180336 | kgp21656902 | kgp21815940 |
| GP1BA | chr17:4835591-4838325 | chr17:4335591-5338325 | chr17:4776371-4779067 | kgp13949132 | kgp11186643 |
| GPR26 | chr10:125425870-125456913 | chr10:124925870-125956913 | chr10:125415860-125444113 | kgp7582662 | kgp21578542 |
| GRB2 | chr17:73314156-73401790 | chr17:72814156-73901790 | chr17:70825751-70913385 | kgp13841089 | kgp14035219 |
| GRB7 | chr17:37894161-37903538 | chr17:37394161-38403538 | chr17:35147712-35157064 | kgp14102913 | kgp13833584 |
| GRIA1 | chr5:152870083-153193429 | chr5:152370083-153693429 | chr5:152850276-153173622 | rs1438937 | rs10057369 |
| GRM2 | chr3:51741080-51752625 | chr3:51241080-52252625 | chr3:51716127-51727665 | rs4367100 | rs13060808 |
| GRM4 | chr6:33989627-34113869 | chr6:33489627-34613869 | chr6:34097605-34231377 | kgp17076142 | rs6909637 |
| GRM6 | chr5:178405329-178422124 | chr5:177905329-178922124 | chr5:178337935-178354730 | rs603852 | rs11249632 |
| HBXIP | chr1:110943876-110950546 | chr1:110443876-111450546 | chr1:110745399-110752069 | kgp8686658 | rs1936942 |
| HD | chr6:125596496-125623282 | chr6:125096496-126123282 | chr6:125638195-125664981 | rs11154263 | rs11967627 |
| HNRPA3 | chr2:178077422-178088685 | chr2:177577422-178588685 | chr2:177785668-177796931 | kgp14203861 | rs1344924 |
| HOMER3 | chr19:19017768-19045219 | chr19:18517768-19545219 | chr19:18901011-18912983 | rs13344313 | rs4808199 |
| HRPT2 | chr1:193091088-193223942 | chr1:192591088-193723942 | chr1:191357711-191490565 | kgp2473538 | kgp12065536 |
| HSP90AB1 | chr6:44214848-44221614 | chr6:43714848-44721614 | chr6:44322826-44329592 | kgp5836209 | kgp8706663 |

*Fig. 2-4*

| Tier 2 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| IL8RB | chr2:218989997-219001975 | chr2:218489997-219501975 | chr2:218698242-218710220 | kgp22730583 | rs1055816 |
| IMPDH2 | chr3:49061761-49066875 | chr3:48561761-49566875 | chr3:49036765-49041879 | kgp22731595 | kgp5626213 |
| IQGAP2 | chr5:75699148-76003957 | chr5:75199148-76503957 | chr5:75734904-76039713 | kgp22490664 | rs11739698 |
| ITGB1 | chr10:33189245-33247293 | chr10:32689245-33747293 | chr10:33229251-33287299 | kgp12034252 | rs11009395 |
| ITGB7 | chr12:53585106-53601000 | chr12:53085106-54101000 | chr12:51871373-51887267 | kgp19011413 | kgp3313746 |
| ITPR1 | chr3:4535031-4889524 | chr3:4035031-5389524 | chr3:4510033-4864286 | kgp17889944 | kgp1749057 |
| KIAA0090 | chr1:19544583-19578046 | chr1:19044583-20078046 | chr1:19417170-19450633 | rs624761 | rs1009631 |
| KIAA1683 | chr19:18367905-18385319 | chr19:17867905-18885319 | chr19:18228907-18246235 | kgp6435620 | rs10412356 |
| LAMA4 | chr6:112429133-112575828 | chr6:111929133-113075828 | chr6:112535826-112682521 | kgp16962466 | kgp17024247 |
| LRP2BP | chr4:186285031-186300172 | chr4:185785031-186800172 | chr4:186522026-186537166 | kgp7238414 | rs9994907 |
| LRRC59 | chr17:48458593-48474914 | chr17:47958593-48974914 | chr17:45813597-45829831 | kgp1609816 | kgp13856216 |
| LTA | chr6:2825414-2827639 | chr6:2825414-2827639 | chr6:2787675-2789683 | kgp11675228 | rs6912537 |
| LYAR | chr4:4269428-4291896 | chr4:3769428-4791896 | chr4:4320337-4342744 | kgp22780996 | kgp7317116 |
| LYN | chr8:56792385-56925006 | chr8:56292385-57425006 | chr8:56954939-57086494 | kgp8836202 | rs2670027 |
| MAP4 | chr3:47892179-48130769 | chr3:47392179-48630769 | chr3:47867188-48105715 | kgp17741397 | rs35623035 |
| MAPT | chr17:43971747-44105699 | chr17:43471747-44605699 | chr17:41327543-41461546 | kgp22730329 | kgp13941400 |
| MARK4 | chr19:45754515-45808541 | chr19:45254515-46308541 | chr19:50446681-50500381 | kgp10230030 | kgp21456098 |
| MC4R | chr18:58038563-58040001 | chr18:57538563-58540001 | chr18:56189543-56190981 | kgp7049183 | kgp1258536 |
| MGC11082 | chr18:3602998-3604385 | chr18:3102998-4104385 | chr18:3592998-3594385 | kgp15965827 | kgp12318627 |
| MRPL14 | chr6:44081372-44095191 | chr6:43581372-44595191 | chr6:44189349-44203169 | kgp17033193 | rs527322 |

*Fig. 2-5*

| Tier 2 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| MRPS16 | chr10:75006445-75012451 | chr10:74506445-75512451 | chr10:74678606-74682457 | kgp21628722 | rs12243089 |
| MTNR1A | chr4:187454808-187476537 | chr4:186954808-187976537 | chr4:187691802-187713531 | rs12648771 | rs4476657 |
| MTNR1B | chr11:92702788-92715948 | chr11:92202788-93215948 | chr11:92342436-92355596 | kgp10063029 | rs2658801 |
| MYC | chr8:128748314-128753680 | chr8:128248314-129253680 | chr8:128817497-128822855 | kgp3177285 | kgp1944877 |
| MYO6 | chr6:76458908-76629254 | chr6:75958908-77129254 | chr6:76515628-76685974 | kgp17262775 | kgp17183304 |
| NANS | chr9:100818958-100845365 | chr9:100318958-101345365 | chr9:99847709-99885178 | rs10817759 | rs2778908 |
| NCK1 | chr3:136581049-136667968 | chr3:136081049-137167968 | chr3:138063762-138150658 | kgp117446 | kgp10600232 |
| NFKBIA | chr14:35870715-35873960 | chr14:35370715-36373960 | chr14:34940466-34943711 | kgp19552677 | kgp19707730 |
| NPY2R | chr4:156129780-156138228 | chr4:155629780-156638228 | chr4:156349230-156357678 | kgp3956236 | kgp20850236 |
| NUDC | chr1:27248223-27272887 | chr1:26748223-27772887 | chr1:27120810-27145474 | rs11247955 | kgp15594139 |
| OPRD1 | chr1:29138653-29190208 | chr1:28638653-29690208 | chr1:29011240-29062795 | kgp9104521 | kgp15855740 |
| PAFAH1B3 | chr19:42801184-42806952 | chr19:42301184-43306952 | chr19:47493024-47498563 | kgp21540635 | kgp22735078 |
| PCBP1 | chr2:70314584-70316334 | chr2:69814584-70816334 | chr2:70168204-70169836 | kgp14596264 | kgp6568959 |
| PCDHA4 | chr5:140186671-140391929 | chr5:139686671-140891929 | chr5:140166855-140372115 | kgp6468526 | kgp10727572 |
| PCID1 | chr11:32605313-32624037 | chr11:32105313-33124037 | chr11:32561889-32580613 | kgp13035948 | rs10836023 |
| PCMT1 | chr6:150070830-150132557 | chr6:149570830-150632557 | chr6:150112657-150174249 | kgp17277449 | kgp10169289 |
| PDCD5 | chr19:33072093-33078358 | chr19:32572093-33578358 | chr19:37763943-37770169 | kgp21531284 | rs7259333 |
| PDE1B | chr12:54943176-54973023 | chr12:54443176-55473023 | chr12:53229670-53259290 | kgp18962385 | rs11171250 |
| PDE6G | chr17:79617488-79623607 | chr17:79117488-80123607 | chr17:77227893-77234038 | kgp317116 | kgp13898509 |
| PGM1 | chr1:64058946-64125916 | chr1:63558946-64625916 | chr1:63831534-63898505 | kgp175729 | kgp15416792 |

Fig. 2-6

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| PHKB | chr16:47495209-47735434 | chr16:46995209-48235434 | chr16:46052710-46292935 | kgp8481371 | rs16945930 |
| PHKG2 | chr16:30759619-30772497 | chr16:30259619-31272497 | chr16:30667237-30676183 | kgp16316196 | kgp22773724 |
| PICK1 | chr22:38453261-38471708 | chr22:37953261-38971708 | chr22:36783207-36801654 | kgp5170623 | kgp1759680 |
| PIK3CA | chr3:178866310-178952497 | chr3:178366310-179452497 | chr3:180349004-180435191 | rs7615444 | rs1025864 |
| PIK3R1 | chr5:67511583-67597649 | chr5:67011583-68097649 | chr5:67547359-67633405 | kgp7844449 | rs7737296 |
| PLA2G7 | chr6:46672052-46703430 | chr6:46172052-47203430 | chr6:46780011-46811110 | kgp4678268 | kgp9155835 |
| PLCB1 | chr20:8113295-8865547 | chr20:7613295-9365547 | chr20:8061295-8813547 | kgp19226483 | rs2076234 |
| PLCB3 | chr11:64018994-64036924 | chr11:63518994-64536924 | chr11:63775697-63793195 | kgp9427286 | rs484886 |
| PLCG2 | chr16:81812898-81991899 | chr16:81312898-82491899 | chr16:80370430-80549400 | kgp4622733 | kgp3230988 |
| PPIH | chr1:43124047-43142429 | chr1:42624047-43642429 | chr1:42896634-42915016 | kgp1870818 | rs11210802 |
| PRDX1 | chr1:45976706-45988562 | chr1:45476706-46488562 | chr1:45749293-45760196 | rs3806405 | kgp15560310 |
| PRKCA | chr17:64298925-64806862 | chr17:63798925-65306862 | chr17:61729387-62237324 | kgp13847618 | kgp13994829 |
| PRLHR | chr10:120352915-120355160 | chr10:119852915-120855160 | chr10:120342905-120345150 | rs853584 | kgp21690663 |
| PRMT1 | chr19:50180408-50191707 | chr19:49680408-50691707 | chr19:54872307-54883516 | kgp1460116 | kgp5315133 |
| PSAT1 | chr9:80912058-80945009 | chr9:80412058-81445009 | chr9:80101878-80134829 | kgp2581728 | kgp9769053 |
| PSEN1 | chr14:73603142-73690399 | chr14:73103142-74190399 | chr14:72672931-72756862 | kgp8405661 | kgp19611371 |
| PSMA1 | chr11:14526421-14665180 | chr11:14026421-15165180 | chr11:14482997-14621739 | kgp12643195 | kgp13010596 |
| PSMC1 | chr14:90722893-90738966 | chr14:90222893-91238966 | chr14:89792646-89808719 | rs10140098 | kgp19595798 |
| PSMD1 | chr2:231921577-232037540 | chr2:231421577-232537540 | chr2:231629852-231745717 | rs1678155 | kgp11602861 |
| PSMD6 | chr3:63996230-64009658 | chr3:63496230-64509658 | chr3:63971270-63984698 | kgp9706776 | kgp17718198 |

*Fig. 2-7*

| Tier 2 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| PSME1 | chr14:24605377-24608176 | chr14:24105377-25108176 | chr14:23675217-23678016 | kgp11494860 | kgp2234181 |
| PTHR2 | chr2:209353736-209704818 | chr2:208853736-210204818 | chr2:209061981-209413063 | kgp14652386 | rs1020407 |
| PYGL | chr14:51371934-51411248 | chr14:50871934-51911248 | chr14:50441686-50480984 | kgp10991856 | rs7146882 |
| PYGM | chr11:64513860-64528187 | chr11:64013860-65028187 | chr11:64270436-64284763 | kgp12876954 | rs675671 |
| RAB2 | chr8:61429469-61536203 | chr8:60929469-62036203 | chr8:61592023-61698757 | kgp7067636 | rs3864667 |
| RALA | chr7:39663151-39747723 | chr7:39163151-40247723 | chr7:39629686-39714242 | kgp22733616 | rs11768838 |
| RCC2 | chr1:17733250-17766250 | chr1:17233250-18266250 | chr1:17605865-17638807 | kgp15535308 | kgp7647703 |
| RGS2 | chr1:192778168-192781407 | chr1:192278168-193281407 | chr1:191044793-191048026 | rs10921130 | kgp11065785 |
| RHOA | chr3:49396578-49449526 | chr3:48896578-49949526 | chr3:49371582-49424530 | kgp11466037 | rs868891 |
| RPA2 | chr1:28218048-28241236 | chr1:27718048-28741236 | chr1:28090635-28113823 | rs12033326 | kgp15705538 |
| RPLP2 | chr11:809935-812876 | chr11:309935-1312876 | chr11:799935-802876 | kgp11473410 | kgp7750669 |
| RPN2 | chr20:35807455-35870025 | chr20:35307455-36370025 | chr20:35240887-35303439 | kgp9846122 | kgp19260650 |
| RPS14 | chr5:149823791-149829319 | chr5:149323791-150329319 | chr5:149803984-149809512 | kgp22444746 | kgp22218062 |
| RRM1 | chr11:4137307-4223759 | chr11:3637307-4723759 | chr11:4072499-4116682 | rs6578398 | kgp4491491 |
| S100A6 | chr1:153507075-153508717 | chr1:153007075-154008717 | chr1:151773699-151775341 | kgp15193014 | rs10908627 |
| SACS | chr13:23902964-24007841 | chr13:23402964-24507841 | chr13:22800964-22905841 | kgp16818396 | rs2765089 |
| SARS | chr1:109756514-109780804 | chr1:109256514-110280804 | chr1:109558062-109582308 | kgp5910329 | rs1803687 |
| SCTR | chr2:120197418-120282028 | chr2:119697418-120782028 | chr2:119913888-119998498 | kgp12364473 | kgp22762988 |
| SET | chr9:131445933-131458675 | chr9:130945933-131958675 | chr9:130485754-130498496 | kgp11282765 | kgp18608937 |
| SF3B14 | chr2:24290453-24299314 | chr2:23790453-24799314 | chr2:24143957-24152818 | kgp14521970 | rs12474894 |

*Fig. 2-8*

| Tier 2 Gene | GeneRange(hg19) | GeneRange+500kb(hg19) | GeneRange(hg18) | StartSNP (GeneRange+ 500kb) | EndSNP (GeneRange+ 500kb) |
|---|---|---|---|---|---|
| SHBG | chr17:7517381-7536700 | chr17:7017381-8036700 | chr17:7458106-7477395 | kgp7760759 | rs6503086 |
| SIAH1 | chr16:48390274-48482309 | chr16:47890274-48982309 | chr16:46947777-47039810 | kgp4639784 | kgp7644930 |
| SLC2A1 | chr1:43391045-43424847 | chr1:42891045-43924847 | chr1:43163632-43197434 | kgp2036523 | rs2782652 |
| SLC6A3 | chr5:1392904-1445543 | chr5:892904-1945543 | chr5:1445909-1498538 | kgp22585075 | kgp9690399 |
| SNCA | chr4:90645249-90759447 | chr4:90145249-91259447 | chr4:90865727-90978470 | kgp11552673 | kgp8195783 |
| SNRPB2 | chr20:16710608-16722417 | chr20:16210608-17222417 | chr20:16658628-16670037 | kgp19326624 | kgp19208923 |
| SOCS6 | chr18:67956136-67997434 | chr18:67456136-68497434 | chr18:66107116-66148414 | kgp10928836 | rs4243325 |
| SOCS7 | chr17:36508006-36561846 | chr17:36008006-37061846 | chr17:33761530-33809545 | rs12936144 | rs4794796 |
| SRC | chr20:35973087-36033821 | chr20:35473087-36533821 | chr20:35406501-35467235 | kgp19359278 | kgp9150551 |
| STAU1 | chr20:47729875-47805288 | chr20:47229875-48305288 | chr20:47163282-47238695 | rs11905650 | kgp19233876 |
| STX12 | chr1:28099693-28150963 | chr1:27599693-28650963 | chr1:27972280-28023550 | kgp22731625 | kgp15287949 |
| SYK | chr9:93564011-93660842 | chr9:93064011-94160842 | chr9:92603890-92698304 | kgp12394293 | rs894962 |
| TBCA | chr5:76986994-77072185 | chr5:76486994-77572185 | chr5:77022750-77107941 | rs2928164 | rs10059285 |
| TBXA2R | chr19:3594503-3606831 | chr19:3094503-4106831 | chr19:3545503-3557658 | kgp21472781 | kgp1760692 |
| TCP1 | chr6:160199529-160210735 | chr6:159699529-160710735 | chr6:160119519-160130725 | kgp16923201 | kgp10518192 |
| TEAD3 | chr6:35441373-35464861 | chr6:34941373-35964861 | chr6:35549351-35572839 | rs847861 | kgp3339 |
| TFAM | chr10:60145175-60155897 | chr10:59645175-60655897 | chr10:59815181-59825903 | kgp9406331 | kgp6514369 |
| TGM2 | chr20:36756863-36793700 | chr20:36256863-37293700 | chr20:36190277-36227114 | rs6067098 | kgp9992037 |
| TJP1 | chr15:29992356-30114706 | chr15:29492356-30614706 | chr15:27779648-27901998 | kgp19895791 | rs2604694 |
| TLR10 | chr4:38773859-38784611 | chr4:38273859-39284611 | chr4:38450646-38460984 | kgp9612652 | rs6531705 |

*Fig. 2-9*

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| TMEM4 | chr12:56704213-56710128 | chr12:56204213-57210128 | chr12:54990480-54996395 | kgp6718939 | kgp6565807 |
| TPI1 | chr12:6976583-6980110 | chr12:6476583-7480110 | chr12:6846966-6850253 | kgp3883976 | kgp18849054 |
| TRAF2 | chr9:139776384-139821067 | chr9:139276384-140321067 | chr9:138896205-138940888 | rs3812570 | kgp9465784 |
| TRMT112 | chr11:64084164-64085033 | chr11:63584164-64585033 | chr11:63840740-63841609 | kgp1242205 | rs2957154 |
| TUBA1 | chr12:49521565-49525304 | chr12:49021565-50025304 | chr12:47807832-47811571 | kgp4948752 | kgp18737983 |
| TUBA1A | chr12:49578582-49582861 | chr12:49078582-50082861 | chr12:47864849-47869128 | kgp5373125 | kgp1407179 |
| TUBA1B | chr12:49521566-49525304 | chr12:49021566-50025304 | chr12:47807832-47866883 | kgp4948752 | kgp18737983 |
| TUBA2 | chr12:49578793-49580616 | chr12:49078793-50080616 | chr12:47865060-47866883 | kgp18983720 | kgp75177 |
| TUBB | chr6:1981087-1986127 | chr6:1981087-1986127 | chr6:1935034-1940074 | kgp17000846 | kgp16908954 |
| TUBG1 | chr17:40761357-40767256 | chr17:40261357-41267256 | chr17:38015219-38020777 | rs12600570 | kgp3534380 |
| TXN | chr9:113006091-113018920 | chr9:112506091-113518920 | chr9:112046130-112058599 | kgp18601393 | kgp652846 |
| TXNDC4 | chr9:102741463-102861330 | chr9:102241463-103361330 | chr9:101781284-101901151 | kgp22740558 | rs10989168 |
| TXNL2 | chr10:131934639-131977932 | chr10:131434639-132477932 | chr10:131824629-131867922 | kgp21587397 | rs2921907 |
| TYMS | chr18:657603-673499 | chr18:157603-1173499 | chr18:647603-663499 | kgp1671520 | kgp5560925 |
| UBQLN4 | chr1:156005091-156023516 | chr1:155505091-156523516 | chr1:154271715-154290140 | rs12746592 | kgp204451 |
| UCHL1 | chr4:41258897-41270446 | chr4:40758897-41770446 | chr4:40953685-40965203 | rs10029833 | kgp21157719 |
| VIPR1 | chr3:42530790-42579065 | chr3:42030790-43079065 | chr3:42519120-42554064 | rs794894 | kgp10771397 |
| YWHAQ | chr2:9724105-9771106 | chr2:9224105-10271106 | chr2:9641556-9688557 | kgp7327726 | rs1138729 |
| ZAP70 | chr2:98330030-98356323 | chr2:97830030-98856323 | chr2:97696462-97722755 | kgp10723114 | kgp14308801 |

*Fig. 2-10*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| ABI3 | chr17:47287588-47300587 | chr17:46787588-47800587 | chr17:44642587-44655586 | rs7211412 | kgp13987803 |
| ACTA1 | chr1:229566992-229569843 | chr1:229066992-230069843 | chr1:227633615-227636466 | kgp706951 | kgp9594907 |
| ACTN2 | chr1:236849769-236927558 | chr1:236349769-237427558 | chr1:234916392-234994181 | kgp12139182 | kgp9945691 |
| ADCY5 | chr3:123001142-123167392 | chr3:122501142-123667392 | chr3:124486088-124650082 | kgp5729470 | kgp18234294 |
| ADCY8 | chr8:131792546-132052835 | chr8:131292546-132552835 | chr8:131861728-132122017 | rs11778881 | kgp4563992 |
| ADCYAP1R1 | chr7:31092075-31151093 | chr7:30592075-31651093 | chr7:31058666-31112836 | kgp6410265 | kgp5976045 |
| ADD3 | chr10:111756107-111895323 | chr10:111256107-112395323 | chr10:111746097-111885313 | kgp2922347 | kgp21705322 |
| AFAP1 | chr4:7760439-7941653 | chr4:7260439-8441653 | chr4:7811339-7992553 | kgp10066670 | kgp2565038 |
| AGTR1 | chr3:148415657-148460790 | chr3:147915657-148960790 | chr3:149898347-149943480 | kgp17969929 | rs9827666 |
| AHCYL1 | chr1:110527386-110566364 | chr1:110027386-111066364 | chr1:110328830-110367887 | kgp15280262 | kgp8467474 |
| AKAP12 | chr6:151561133-151679694 | chr6:151061133-152179694 | chr6:151603201-151719602 | kgp17415975 | kgp17180004 |
| AKAP13 | chr15:85923870-86292586 | chr15:85423870-86792586 | chr15:83724874-84093590 | rs11073778 | kgp10945265 |
| AKAP5 | chr14:64932216-64941221 | chr14:64432216-65441221 | chr14:64001969-64010974 | rs945029 | rs4499147 |
| AKAP9 | chr7:91570188-91739987 | chr7:91070188-92239987 | chr7:91408127-91577925 | kgp7513665 | kgp8102448 |
| AKR1C3 | chr10:5005453-5149878 | chr10:4505453-5649878 | chr10:4995453-5139878 | rs1679414 | kgp8379007 |
| AKT1 | chr14:105235686-105262080 | chr14:104735686-105762080 | chr14:104306731-104333125 | kgp10896929 | kgp7260890 |
| ANK2 | chr4:113739238-114304896 | chr4:113239238-114804896 | chr4:113958687-114524345 | kgp8454825 | kgp10144793 |
| ANKRD24 | chr19:4183350-4224811 | chr19:3683350-4724811 | chr19:4134350-4175811 | kgp3226366 | rs7255543 |

Fig. 3-1

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| ANXA6 | chr5:150480266-150537443 | chr5:149980266-151037443 | chr5:150460460-150517560 | kgp22603058 | rs11747938 |
| ANXA7 | chr10:75135188-75173841 | chr10:74635188-75673841 | chr10:74805194-74843847 | kgp21588521 | kgp5026768,rs2227568 |
| APLP2 | chr11:129939715-130014706 | chr11:129439715-130514706 | chr11:129445010-129519910 | kgp22802171 | rs7116475 |
| AR | chrX:66763873-66950461 | chrX:66263873-67450461 | chrX:66680598-66860844 | rs478505 | kgp22776402 |
| ARF1 | chr1:228270360-228286913 | chr1:227770360-228786913 | chr1:226336983-226353536 | kgp7035482 | kgp5092378 |
| ARF3 | chr12:49329991-49351252 | chr12:48829991-49851252 | chr12:47616258-47637519 | kgp9963537 | kgp19162961 |
| ARHGAP1 | chr11:46698631-46722120 | chr11:46198631-47222120 | chr11:46655207-46678696 | rs11038804 | kgp12872953 |
| ARHGEF1 | chr19:42399421-42434296 | chr19:41899421-42934296 | chr19:47079106-47103444 | kgp21546138 | kgp9753873 |
| ARL3 | chr10:104433483-104474190 | chr10:103933483-104974190 | chr10:104423477-104464180 | rs4919614 | kgp2065500 |
| ARL8B | chr3:5163929-5222601 | chr3:4663929-5722601 | chr3:5138929-5197601 | kgp5083934 | kgp17728482 |
| ASCL2 | chr11:2289727-2292182 | chr11:1789727-2792182 | chr11:2246303-2248758 | kgp12845252 | kgp7129584 |
| ATF3 | chr1:212738675-212794119 | chr1:212238675-213294119 | chr1:210805319-210860739 | rs10863936 | kgp12569686 |
| ATN1 | chr12:7033625-7053815 | chr12:6533625-7553815 | chr12:6903886-6924076 | kgp18714644 | kgp19128481 |
| ATP1B1 | chr1:169075946-169101960 | chr1:168575946-169601960 | chr1:167342570-167368584 | rs10800363 | kgp305361 |
| ATP2B1 | chr12:89981825-90049844 | chr12:89481825-90549844 | chr12:88505956-88573975 | kgp4237218 | kgp19117315 |
| ATP2B2 | chr3:10365706-10749716 | chr3:9865706-11249716 | chr3:10342743-10724716 | kgp7774534 | rs7625756 |
| ATXN1 | chr6:16299342-16761721 | chr6:15799342-17261721 | chr6:16407321-16869700 | kgp2173519 | rs6921352 |
| ATXN3 | chr14:92524895-92572965 | chr14:92024895-93072965 | chr14:91594648-91642718 | kgp11986238 | rs2146498 |
| ATXN7 | chr3:63850232-63989136 | chr3:63350232-64489136 | chr3:63825272-63964176 | rs9311874 | kgp797614 |
| AVPR1A | chr12:63540215-63546590 | chr12:63040215-64046590 | chr12:61826482-61832857 | rs952865 | kgp3671976 |
| B4GALT1 | chr9:33110638-33167356 | chr9:32610638-33667356 | chr9:33100638-33157356 | kgp18539535 | kgp18370584 |

Fig. 3-2

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| BANK1 | chr4:102341117-102995969 | chr4:101841117-103495969 | chr4:102560140-103214992 | rs6851921 | kgp20796561 |
| BCAP31 | chrX:152965946-152990201 | chrX:152465946-153490201 | chrX:152619145-152643081 | rs6627302 | kgp22764947 |
| BCAR1 | chr16:75262927-75301951 | chr16:74762927-75801951 | chr16:73820428-73859452 | kgp7158675 | kgp16367309 |
| BCL2 | chr18:60790578-60986657 | chr18:60290578-61486657 | chr18:58941558-59137637 | rs435439 | rs1720898 |
| BMI1 | chr10:22610138-22620414 | chr10:22110138-23120414 | chr10:22645304-22660192 | kgp3019331 | rs12775513 |
| BMPR2 | chr2:203241049-203432474 | chr2:202741049-203932474 | chr2:202949294-203140719 | rs2072504 | kgp3183288 |
| BOC | chr3:112930411-113006305 | chr3:112430411-113506305 | chr3:114413101-114488995 | kgp12164746 | kgp3299668 |
| BPGM | chr7:134331530-134364567 | chr7:133831530-134864567 | chr7:133982094-134015107 | kgp13720725 | kgp8542611 |
| BRCA1 | chr17:41196311-41322420 | chr17:40696311-41822420 | chr17:38449839-38530994 | kgp1014784 | kgp13921789 |
| BRCA2 | chr13:32889616-32973809 | chr13:32389616-33473809 | chr13:31787616-31871809 | rs2146284 | rs9596502 |
| BRD7 | chr16:50352928-50402845 | chr16:49852928-50902845 | chr16:48910441-48960330 | kgp3843480 | kgp6018549 |
| BRF2 | chr8:37701397-37707431 | chr8:37201397-38207431 | chr8:37820560-37826569 | rs7818467 | kgp22772561 |
| BRMS1 | chr11:66104803-66112582 | chr11:65604803-66612582 | chr11:65861379-65869158 | kgp22746103 | kgp12809093 |
| BTK | chrX:100604434-100645770 | chrX:100104434-101145770 | chrX:100491097-100532426 | kgp22759057 | kgp22747202 |
| C1orf128 | chr1:24104887-24114722 | chr1:23604887-24614722 | chr1:23977474-23987309 | kgp283495 | kgp2701674 |
| C1orf42 | chr1:152486978-152488481 | chr1:151986978-152988481 | chr1:150753602-150755105 | kgp15694971 | rs4363385 |
| C1QBP | chr17:5336098-5342471 | chr17:4836098-5842471 | chr17:5276822-5283195 | kgp14047547 | rs17825455 |
| C20orf20 | chr20:61427804-61431945 | chr20:60927804-61931945 | chr20:60898282-60902390 | kgp9228388 | kgp19363625 |
| C20orf24 | chr20:35234136-35240960 | chr20:34734136-35740960 | chr20:34636369-34674374 | rs6060820 | rs1744760 |
| C4orf14 | chr4:57829515-57843826 | chr4:57329515-58343826 | chr4:57524272-57538583 | kgp22756132 | kgp1831456 |
| C4orf17 | chr4:100432160-100463460 | chr4:99932160-100963460 | chr4:100651222-100682483 | kgp20878925 | kgp21204347 |

*Fig. 3-3*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| C5orf25 | chr5:175665369-175772990 | chr5:175165369-176272990 | chr5:175598008-175705596 | kgp7679859 | rs480782 |
| C9orf25 | chr9:34398181-34458568 | chr9:33898181-34958568 | chr9:34388181-34448568 | kgp22772722 | rs7031962 |
| CABIN1 | chr22:24407764-24574596 | chr22:23907764-25074596 | chr22:22737764-22904596 | kgp5637302 | kgp5793536 |
| CABP1 | chr12:121078421-121105127 | chr12:120578421-121605127 | chr12:119562804-119589510 | kgp18737891 | rs503720 |
| CACNA1C | chr12:2162415-2807115 | chr12:1662415-3307115 | chr12:2032676-2677376 | kgp9477564 | kgp1276729 |
| CALCR | chr7:93053798-93204042 | chr7:92553798-93704042 | chr7:92891734-93041978 | kgp3815436 | kgp10249142 |
| CALD1 | chr7:134464163-134655480 | chr7:133964163-135155480 | chr7:134114710-134306012 | rs16874469 | kgp22829820 |
| CAMK2A | chr5:149599053-149669403 | chr5:149099053-150169403 | chr5:149579247-149649529 | kgp9269229 | kgp22536863 |
| CAMK2G | chr10:75572258-75634349 | chr10:75072258-76134349 | chr10:75242264-75304349 | kgp5617603 | kgp4007437 |
| CAMKK1 | chr17:3763616-3796337 | chr17:3263616-4296337 | chr17:3710365-3743086 | kgp4927794 | kgp13998561 |
| CAMKK2 | chr12:121675494-121736111 | chr12:121175494-122236111 | chr12:120159877-120220494 | kgp3636283,rs1800556 | kgp3169612 |
| CAPN2 | chr1:223889294-223963720 | chr1:223389294-224463720 | chr1:221966741-222030343 | rs2430408 | kgp15138476 |
| CASP3 | chr4:185548849-185570629 | chr4:185048849-186070629 | chr4:185785843-185807623 | kgp8529169 | rs2046535 |
| CASP6 | chr4:110609784-110624629 | chr4:110109784-111124629 | chr4:110829233-110844078 | kgp20840443 | kgp20817413 |
| CASP7 | chr10:115438934-115490664 | chr10:114938934-115990664 | chr10:115428924-115480654 | kgp12503193 | rs12266538 |
| CASP8 | chr2:202098165-202152434 | chr2:201598165-202652434 | chr2:201806410-201860679 | kgp6115041 | rs12468196 |
| CASR | chr3:121902529-122005344 | chr3:121402529-122505344 | chr3:123385219-123488034 | kgp18115887 | rs13095775 |
| CAV1 | chr7:115929905-116201239 | chr7:115429905-116701239 | chr7:115717141-115988466 | kgp13705413 | kgp1550529,rs13222576 |
| CBL | chr11:119076989-119178859 | chr11:118576989-119678859 | chr11:118582199-118684069 | kgp4184476 | rs10892470 |
| CBX1 | chr17:46147413-46178883 | chr17:45647413-46678883 | chr17:43502412-43533882 | kgp4510682 | kgp14007862 |
| CCDC106 | chr19:56158953-56164526 | chr19:55658953-56664526 | chr19:60850765-60856338 | kgp2072564 | rs901476 |

*Fig. 3-4*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| CCND1 | chr11:69455872-69469242 | chr11:68955872-69969242 | chr11:69165053-69178423 | kgp12357966 | rs1893085 |
| CCNE1 | chr19:30302900-30315215 | chr19:29802900-30815215 | chr19:34994740-35007059 | kgp21358604 | kgp21349680 |
| CCR4 | chr3:32993065-32996403 | chr3:32493065-33496403 | chr3:32968069-32971407 | rs4955290 | kgp3855989 |
| CCR5 | chr3:46411632-46417697 | chr3:45911632-46917697 | chr3:46386636-46392701 | kgp17737690 | rs936173 |
| CD163 | chr12:7623411-7656414 | chr12:7123411-8156414 | chr12:7514676-7547681 | rs9668071 | kgp3219786 |
| CD5 | chr11:60869929-60895323 | chr11:60369929-61395323 | chr11:60626505-60651899 | rs7927817 | kgp13056421 |
| CD9 | chr12:6309481-6347437 | chr12:5809481-6847437 | chr12:6179133-6217688 | rs9669580 | kgp1124940 |
| CDC2 | chr10:62538235-62553924 | chr10:62038235-63053924 | chr10:62208241-62223930 | kgp21922934 | rs3125326 |
| CDKN2C | chr1:51433607-51440309 | chr1:50933607-51940309 | chr1:51206195-51212897 | rs17106219 | kgp15324656 |
| CENTA1 | chr7:937537-994306 | chr7:437537-1494306 | chr7:904063-960832 | kgp4856315,rs3924019 | kgp11391801 |
| CETN3 | chr5:89689528-89705603 | chr5:89189528-90205603 | chr5:89725284-89741359 | rs277054 | kgp22368793 |
| CFTR | chr7:117120016-117308718 | chr7:116620016-117808718 | chr7:116907252-117095954 | kgp13265715 | kgp13590397 |
| CHAT | chr10:50822349-50901939 | chr10:50322349-51401939 | chr10:50487146-50543156 | kgp8189482 | kgp8898453 |
| CHD3 | chr17:7788122-7816075 | chr17:7288122-8316075 | chr17:7728847-7756800 | rs7208523 | kgp11776706 |
| CHUK | chr10:101948123-101989344 | chr10:101448123-102489344 | chr10:101938113-101979334 | kgp6141810 | kgp9150190 |
| CISH | chr3:50643884-50649262 | chr3:50143884-51149262 | chr3:50618929-50624207 | kgp5610191 | rs6783700 |
| CKAP1 | chr19:36605888-36616849 | chr19:36105888-37116849 | chr19:41297728-41308689 | rs7249516 | rs3108171 |
| CKMT2 | chr5:80529138-80562217 | chr5:80029138-81062217 | chr5:80564894-80597973 | kgp9822295 | kgp7416171 |
| CLTB | chr5:175819455-175843540 | chr5:175319455-176343540 | chr5:175752061-175776146 | rs4867811 | kgp1551194 |
| CLU | chr8:27454433-27472328 | chr8:26954433-27972328 | chr8:27510367-27528244 | kgp886026 | rs4732823 |
| CMIP | chr16:81478774-81745367 | chr16:80978774-82245367 | chr16:80036394-80302866 | rs11150329 | kgp16425289 |

*Fig. 3-5*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| CNGA2 | chrX:150903217-150914036 | chrX:150403217-151414036 | chrX:150653873-150664692 | rs1202896 | kgp22766776 |
| CNKSR2 | chrX:21392535-21672813 | chrX:20892535-22172813 | chrX:21302900-21580700 | kgp22768242 | kgp22744096 |
| CNN1 | chr19:11649578-11661138 | chr19:11149578-12161138 | chr19:11510578-11522138 | kgp11148982 | rs8100428 |
| CNR2 | chr1:24200459-24239817 | chr1:23700459-24739817 | chr1:24073046-24112404 | rs9887921 | kgp7256331 |
| COIL | chr17:55015560-55038411 | chr17:54515560-55538411 | chr17:52370559-52393410 | rs7219528 | kgp13879956 |
| CORO1B | chr11:67205517-67211292 | chr11:66705517-67711292 | chr11:66962093-66967839 | kgp8733070 | kgp12910446 |
| COX17 | chr3:119388371-119396243 | chr3:118888371-119896243 | chr3:120871061-120878933 | rs2903301 | rs7634938 |
| CPE | chr4:166300096-166419482 | chr4:165800096-166919482 | chr4:166519546-166638932 | rs4541465 | kgp20841166 |
| CRADD | chr12:94071150-94288616 | chr12:93571150-94788616 | chr12:92595281-92768662 | kgp18995270 | rs10859694 |
| CREM | chr10:35415768-35501886 | chr10:34915768-36001886 | chr10:35455806-35541892 | kgp21684668 | rs654221 |
| CRIPT | chr2:46844324-46852881 | chr2:46344324-47352881 | chr2:46697811-46705687 | kgp11216746 | kgp5110136 |
| CSNK2A1 | chr20:463337-524482 | chr20:1-1024482 | chr20:411337-472482 | kgp19358001 | kgp2852236 |
| CSNK2A2 | chr16:58191811-58231782 | chr16:57691811-58731782 | chr16:56749312-56789283 | kgp3607479 | kgp9299300 |
| CSNK2B | chr6:2919235-2923423 | chr6:2919235-2923423 | chr6:31741635-31748206 | kgp7558035 | kgp17052091 |
| CTNNB1 | chr3:41236400-41280845 | chr3:40736400-41780845 | chr3:41211404-41255849 | kgp17791054 | kgp17873276 |
| DAPK3 | chr19:3958451-3971038 | chr19:3458451-4471038 | chr19:3909451-3922038 | kgp9392695 | kgp6448823 |
| DBN1 | chr5:176883613-176900694 | chr5:176383613-177400694 | chr5:176816219-176833300 | rs3733876 | kgp6700800 |
| DDIT4 | chr10:74033676-74035797 | chr10:73533676-74535797 | chr10:73703682-73705803 | kgp21593001 | kgp10561095 |
| DDX5 | chr17:62494373-62502484 | chr17:61994373-63002484 | chr17:59926199-59932869 | kgp14113893 | rs4239089 |
| DEFB1 | chr8:6728096-6735529 | chr8:6228096-7235529 | chr8:6715508-6722939 | kgp20078124 | rs12680482 |
| DGKD | chr2:234263152-234380743 | chr2:233763152-234880743 | chr2:233927891-234045482 | rs12477794 | rs28902188 |

*Fig. 3-6*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| DGKZ | chr11:46354454-46402104 | chr11:45854454-46902104 | chr11:46311314-46358680 | rs2090602 | kgp22737291 |
| DIRAS2 | chr9:93372113-93405108 | chr9:92872113-93905108 | chr9:92411933-92444928 | rs7860989 | kgp10944799 |
| DLG1 | chr3:196769430-197026143 | chr3:196269430-197526143 | chr3:198253827-198510540 | kgp18074003 | rs841672 |
| DLG3 | chrX:69664704-69725339 | chrX:69164704-70225339 | chrX:69581448-69642062 | kgp22756738 | kgp22752290 |
| DLG4 | chr17:7093209-7123369 | chr17:6593209-7623369 | chr17:7033933-7063781 | kgp10999626 | rs3744258 |
| DNM1 | chr9:130965662-131017527 | chr9:130465662-131517527 | chr9:130005483-130057348 | kgp1183767 | rs4836625 |
| DNM3 | chr1:171810620-172381857 | chr1:171310620-172881857 | chr1:170077260-170648480 | kgp15671556 | rs2213746 |
| DNMT2 | chr10:17184981-17243681 | chr10:16684981-17743681 | chr10:17224987-17283687 | kgp1566842 | kgp21855354 |
| DPYSL2 | chr8:26371708-26515693 | chr8:25871708-27015693 | chr8:26427707-26571610 | rs11998023 | rs12544814 |
| DRD1 | chr5:174867674-174871163 | chr5:174367674-175371163 | chr5:174800280-174803769 | kgp4432341 | kgp8293487 |
| DRD1IP | chr5:174867675-174871163 | chr5:174367675-175371163 | chr5:174800281-174803769 | kgp4432341 | kgp8293487 |
| DST | chr6:56479153-56716714 | chr6:55979153-57216714 | chr6:56430743-56816422 | kgp1980963 | rs12209200 |
| DVL1 | chr1:1270657-1284492 | chr1:770657-1784492 | chr1:1260520-1274355 | kgp4076808 | kgp15201879 |
| DVL2 | chr17:7128660-7137863 | chr17:6628660-7637863 | chr17:7069384-7078587 | kgp1788685 | kgp2456831,rs3744255 |
| DVL3 | chr3:183873283-183891314 | chr3:183373283-184391314 | chr3:185355977-185374008 | kgp10156744 | kgp4088221 |
| EDF1 | chr9:139756570-139760738 | chr9:139256570-140260738 | chr9:138876391-138880559 | rs3829109 | kgp4292076 |
| EDG3 | chr9:91606324-91620069 | chr9:91106324-92120069 | chr9:90796144-90809889 | kgp18366537 | kgp113389 |
| EDG5 | chr19:10332109-10341948 | chr19:9832109-10841948 | chr19:10193109-10202948 | kgp21505357 | kgp12277401 |
| EDG8 | chr19:10623418-10628668 | chr19:10123418-11128668 | chr19:10484418-10489668 | rs4804478 | kgp9055694 |
| EEF1D | chr8:144661866-144679845 | chr8:144161866-145179845 | chr8:144733040-144750726 | kgp20077380 | kgp4311396 |
| EEF2 | chr19:3976053-3985461 | chr19:3476053-4485461 | chr19:3927053-3936461 | kgp21334437 | rs10406730 |

Fig. 3-7

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| EFNB1 | chrX:68048839-68066029 | chrX:67548839-68566029 | chrX:67965564-67982754 | rs7879567 | kgp22774708 |
| EFNB2 | chr13:107142078-107187388 | chr13:106642078-107687388 | chr13:105940096-105985338 | rs9587049 | kgp1472981 |
| EIF1B | chr3:40351172-40353915 | chr3:39851172-40853915 | chr3:40326176-40328919 | kgp17543799 | kgp724180 |
| ENO2 | chr12:7023613-7032859 | chr12:6523613-7532859 | chr12:6893874-6903120 | kgp6644683 | kgp18788179 |
| EPB41 | chr1:29213602-29446558 | chr1:28713602-29946558 | chr1:29086214-29319545 | kgp15837735 | kgp8194212 |
| EPB41L1 | chr20:34679425-34820721 | chr20:34179425-35320721 | chr20:34142839-34284135 | rs1886695 | kgp10646202 |
| EPB41L2 | chr6:131160487-131384462 | chr6:130660487-131884462 | chr6:131202180-131426058 | kgp3398782 | kgp16921144 |
| EPHB2 | chr1:23037330-23241823 | chr1:22537330-23741823 | chr1:22909917-23114410 | rs2473249 | kgp22776625 |
| ESR1 | chr6:152011630-152424408 | chr6:151511630-152924408 | chr6:152053323-152466101 | rs9478984 | rs818451 |
| ESR2 | chr14:64693750-64805268 | chr14:64193750-65305268 | chr14:63763503-63875021 | kgp3039416 | kgp8515773 |
| ESRRG | chr1:216676587-217311097 | chr1:216176587-217811097 | chr1:214743210-215377720 | kgp2104463 | kgp3054869 |
| ETHE1 | chr19:44010870-44031396 | chr19:43510870-44531396 | chr19:48702710-48723236 | rs11668932 | kgp561363 |
| EWSR1 | chr22:29663997-29696515 | chr22:29163997-30196515 | chr22:27994016-28026515 | rs6005868 | rs4823054 |
| F11R | chr1:160965000-161008774 | chr1:160465000-161508774 | chr1:159231624-159275404 | rs678456 | kgp10744728 |
| FADD | chr11:70049268-70053508 | chr11:69549268-70553508 | chr11:69726916-69731134 | kgp12619639 | kgp12640488 |
| FAS | chr10:90729552-90775542 | chr10:90229552-91275542 | chr10:90740267-90765522 | kgp6970830 | kgp1640747 |
| FBLIM1 | chr1:16083153-16113084 | chr1:15583153-16613084 | chr1:15955740-15985671 | rs16851480 | kgp15648830 |
| FER | chr5:108083522-108523373 | chr5:107583522-109023373 | chr5:108111421-108551272 | rs11958626 | rs845734 |
| FEZ1 | chr11:125315640-125366206 | chr11:124815640-125866206 | chr11:124820857-124871333 | rs10160591 | kgp12966369 |
| FEZ2 | chr2:36779403-36825332 | chr2:36279403-37325332 | chr2:36632904-36678836 | kgp10246319 | kgp9712350 |
| FFAR1 | chr19:35842444-35843367 | chr19:35342444-36343367 | chr19:40534294-40535197 | rs8106116 | kgp21511691 |

*Fig. 3-8*

| Tier 3 Gene | GeneRange(hg19) | GeneRange+500kb(hg19) | GeneRange(hg18) | StartSNP (GeneRange+ 500kb) | EndSNP (GeneRange+500 kb) |
| --- | --- | --- | --- | --- | --- |
| FFAR2 | chr19:35939202-35941865 | chr19:35439202-36441865 | chr19:40631042-40633705 | rs2112502 | rs7247246 |
| FKBP1A | chr20:1349620-1373816 | chr20:849620-1873816 | chr20:1297621-1321745 | kgp4567229 | kgp10348674 |
| FLJ31945 | chr13:50699952-50702599 | chr13:50199952-51202599 | chr13:49597953-49600600 | kgp9786864 | kgp16621897 |
| FLJ41278 | chr12:65277553-65371302 | chr12:64777553-65871302 | chr12:63563820-63657569 | rs6581555 | kgp1662303 |
| FLNA | chrX:153576899-153603006 | chrX:153076899-154103006 | chrX:153230093-153256200 | rs7049293 | rs28412378 |
| FLNB | chr3:57994126-58157982 | chr3:57494126-58657982 | chr3:57969166-58133017 | rs7629743 | rs11130670 |
| FREQ | chr9:132934856-132999583 | chr9:132434856-133499583 | chr9:131974677-132039404 | kgp12208188 | kgp18380808 |
| FRS2 | chr12:69864128-69973562 | chr12:69364128-70473562 | chr12:68150395-68259829 | kgp19095191 | kgp12534834 |
| FSHR | chr2:49189295-49381666 | chr2:48689295-49881666 | chr2:49043155-49235134 | kgp297164 | kgp11229604 |
| FXN | chr9:71650478-71715094 | chr9:71150478-72215094 | chr9:70840163-70878772 | rs265076 | kgp213209 |
| FXR1 | chr3:180630233-180700539 | chr3:180130233-181200539 | chr3:182113145-182177647 | kgp22773686 | kgp3235523 |
| G6PD | chrX:153759605-153775787 | chrX:153259605-154275787 | chrX:153412799-153428981 | rs2239471 | kgp22745531 |
| GABRR1 | chr6:89887222-89927496 | chr6:89387222-90427496 | chr6:89944690-89983779 | kgp3728710 | kgp17056993 |
| GABRR2 | chr6:89967238-90024967 | chr6:89467238-90524967 | chr6:90023957-90081686 | kgp16994883 | kgp9012178 |
| GALR2 | chr17:74070891-74073573 | chr17:73570891-74573573 | chr17:71582486-71585168 | rs1042861 | rs16967307 |
| GAP43 | chr3:115342150-115440334 | chr3:114842150-115940334 | chr3:116825141-116922842 | rs10511341 | kgp18168870 |
| GC | chr4:72607410-72671237 | chr4:72107410-73171237 | chr4:72826274-72888622 | rs10013437 | kgp12025264 |
| GFAP | chr17:42982993-42992920 | chr17:42482993-43492920 | chr17:40338518-40348394 | rs8066197 | rs12947718 |
| GFI1 | chr1:92940317-92952433 | chr1:92440317-93452433 | chr1:92712905-92725021 | kgp80379 | kgp15436210 |
| GFI1B | chr9:135853893-135867084 | chr9:135353893-136367084 | chr9:134843714-134856903 | kgp1227599 | kgp22817803 |
| GFPT1 | chr2:69546900-69614386 | chr2:69046900-70114386 | chr2:69405910-69467829 | kgp7360674 | kgp14824626 |

*Fig. 3-9*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| GH1 | chr17:61994562-61996198 | chr17:61494562-62496198 | chr17:59348294-59349930 | kgp6455446 | kgp10132757 |
| GIT1 | chr17:27900486-27916610 | chr17:27400486-28416610 | chr17:24924612-24940736 | kgp14082001 | rs8065059 |
| GIT2 | chr12:110367606-110434194 | chr12:109867606-110934194 | chr12:108851991-108918483 | kgp8064273 | kgp556710 |
| GJA1 | chr6:121756744-121770873 | chr6:121256744-122270873 | chr6:121798443-121812572 | kgp5203283 | kgp1494786 |
| GJB1 | chrX:70435061-70445065 | chrX:69935061-70945065 | chrX:70351786-70361777 | kgp22820938 | rs35542412 |
| GMFB | chr14:54941208-54955744 | chr14:54441208-55455744 | chr14:54010958-54025494 | kgp5212952 | kgp7377769 |
| GNA12 | chr7:2767740-2883959 | chr7:2267740-3383959 | chr7:2734266-2850485 | kgp9177535 | kgp13694655 |
| GNAS | chr20:57414794-57486250 | chr20:56914794-57986250 | chr20:56848189-56919645 | rs471661 | rs729997 |
| GNAZ | chr22:23412668-23467221 | chr22:22912668-23967221 | chr22:21742668-21797221 | kgp15075658 | rs9680742 |
| GPM6A | chr4:176554087-176923648 | chr4:176054087-177423648 | chr4:176791081-177160642 | rs6849435 | kgp8852764 |
| GPSM2 | chr1:109419602-109476957 | chr1:108919602-109976957 | chr1:109221125-109274567 | kgp15175401 | kgp15178378 |
| GRB14 | chr2:165349322-165478360 | chr2:164849322-165978360 | chr2:165057568-165186606 | kgp8982508 | kgp14153450 |
| GRIA2 | chr4:158141294-158287226 | chr4:157641294-158787226 | chr4:158361185-158506676 | kgp22818527 | rs6836401 |
| GRIA3 | chrX:122318095-122624766 | chrX:121818095-123124766 | chrX:122145776-122452447 | rs7057244 | rs12559968 |
| GRIA4 | chr11:105480799-105852819 | chr11:104980799-106352819 | chr11:104986009-105358029 | kgp12888967 | kgp2959570 |
| GRIN1 | chr9:140033608-140063214 | chr9:139533608-140563214 | chr9:139153429-139183029 | kgp18425565 | kgp18521447 |
| GRIN2A | chr16:9847264-10276611 | chr16:9347264-10776611 | chr16:9762922-10184112 | kgp16441783 | rs9932893 |
| GRIN2B | chr12:13714409-14133022 | chr12:13214409-14633022 | chr12:13605676-14024289 | rs3741818 | kgp7391296 |
| GRK1 | chr13:114321596-114438637 | chr13:113821596-114938637 | chr13:113369597-113373973 | kgp16671784 | rs11147317 |
| GRK4 | chr4:2965342-3042474 | chr4:2465342-3542474 | chr4:2935140-3012272 | rs846252 | rs6821202 |
| GSK3A | chr19:42734337-42746736 | chr19:42234337-43246736 | chr19:47426177-47438576 | kgp21481263 | kgp10870487 |

*Fig. 3-10*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| GSK3B | chr3:119540801-119813264 | chr3:119040801-120313264 | chr3:121028235-121295203 | kgp17616951 | kgp4570827 |
| GSTM4 | chr1:110198697-110208123 | chr1:109698697-110708123 | chr1:110000225-110009648 | rs595635 | kgp15760598 |
| HABP4 | chr9:99212413-99253618 | chr9:98712413-99753618 | chr9:98252234-98293439 | kgp18578220 | kgp18630342 |
| HAND1 | chr5:153854531-153857824 | chr5:153354531-154357824 | chr5:153834724-153838017 | kgp7530958 | rs2431184 |
| HAND2 | chr4:174447651-174451378 | chr4:173947651-174951378 | chr4:174684226-174687953 | kgp20847640 | kgp20778226 |
| HARS | chr5:140053489-140070971 | chr5:139553489-140570971 | chr5:140033673-140051155 | rs6874491 | rs12654953 |
| HDAC6 | chrX:48660286-48683380 | chrX:48160286-49183380 | chrX:48545430-48568324 | kgp22835768 | rs2015487 |
| HES1 | chr3:193853930-193856401 | chr3:193353930-194356401 | chr3:195336627-195339090 | kgp11414670 | rs7649259 |
| HLA-A | chr6:1150035-1295564 | chr6:1150035-1295564 | chr6:30018304-30085130 | rs9392258 | rs9391920 |
| HLA-C | chr6:2585738-2671188 | chr6:2585738-2671188 | chr6:2486041-2572197 | rs9392400 | kgp1905253 |
| HLA-DQA2 | chr6:4166320-4171833 | chr6:4166320-4171833 | chr6:3895192-3901275 | kgp17451336 | kgp17218419 |
| HMGB1 | chr13:31032878-31191510 | chr13:30532878-31691510 | chr13:29930878-30089510 | rs1557088 | kgp8054835 |
| HMGN1 | chr21:40714240-40721047 | chr21:40214240-41221047 | chr21:39636110-39643140 | kgp4524272 | kgp8317624 |
| HMGN2 | chr1:26798901-26803133 | chr1:26298901-27303133 | chr1:26671488-26675720 | rs1429936 | kgp8260087 |
| HMMR | chr5:162887516-162918953 | chr5:162387516-163418953 | chr5:162820240-162851525 | kgp9548441 | rs1363073 |
| HMOX2 | chr16:4524718-4560348 | chr16:4024718-5060348 | chr16:4464719-4500349 | kgp16414002 | kgp7117794 |
| HMP19 | chr5:173472723-173536182 | chr5:172972723-174036182 | chr5:173405329-173468788 | kgp22404239 | rs12186684 |
| HOMER2 | chr15:83517728-83621476 | chr15:83017728-84121476 | chr15:81314789-81412477 | rs1267659 | kgp4123064 |
| HRH4 | chr18:22040592-22059921 | chr18:21540592-22559921 | chr18:20294590-20313919 | rs7235445 | kgp7887799 |
| HSP90AA1 | chr14:102547074-102606086 | chr14:102047074-103106086 | chr14:101616827-101675839 | kgp3260354 | kgp19714004 |
| HSPA1A | chr6:31783290-31785719 | chr6:31283290-32285719 | chr6:31891315-31893698 | kgp4709627 | rs9296020 |

*Fig. 3-11*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| HSPA1B | chr6:3089162-3091686 | chr6:3089162-3091686 | chr6:3043109-3045633 | kgp6503147 | kgp5869121 |
| HSPA4 | chr5:132387661-132440709 | chr5:131887661-132940709 | chr5:132415560-132468608 | kgp22352512 | kgp7658141 |
| HSPB1 | chr7:75931874-75933614 | chr7:75431874-76433614 | chr7:75769858-75771546 | kgp4195218 | kgp10852432 |
| HSPB3 | chr5:53751430-53752214 | chr5:53251430-54252214 | chr5:53787201-53787964 | rs16881895 | rs3815916 |
| HSPB8 | chr12:119616594-119632551 | chr12:119116594-120132551 | chr12:118100977-118116934 | kgp18981306 | kgp18823622 |
| HSPBP1 | chr19:55773590-55791751 | chr19:55273590-56291751 | chr19:60465518-60483540 | kgp3134010 | kgp21533588 |
| HSPE1 | chr2:198364720-198368187 | chr2:197864720-198868187 | chr2:198073364-198076416 | kgp9884304 | kgp12004769 |
| HSPH1 | chr13:31710762-31736502 | chr13:31210762-32236502 | chr13:30608762-30634502 | kgp16548529 | kgp16811501 |
| HTATIP | chr11:20385289-20405329 | chr11:19885289-20905329 | chr11:20341865-20361905 | rs2707094 | kgp309631 |
| HTR2B | chr2:231972949-231989824 | chr2:231472949-232489824 | chr2:231681198-231698068 | rs6761068 | rs4973459 |
| HTR2C | chrX:113818550-114144624 | chrX:113318550-114644624 | chrX:113724806-114050880 | rs7055827 | kgp22830072 |
| HTR6 | chr1:19991779-20006055 | chr1:19491779-20506055 | chr1:19864366-19878642 | kgp15912015 | kgp10523409 |
| IGSF4 | chr11:115044345-115375241 | chr11:114544345-115875241 | chr11:114549555-114880451 | rs1607260 | rs7928212 |
| IKBKB | chr8:42128819-42190171 | chr8:41628819-42690171 | chr8:42247985-42309122 | kgp9748756 | kgp3164559 |
| IKBKE | chr1:206643585-206670223 | chr1:206143585-207170223 | chr1:204710418-204736845 | kgp15543770 | kgp6359437 |
| IKBKG | chrX:153770458-153793261 | chrX:153270458-154293261 | chrX:153423652-153446455 | rs633 | kgp22831959 |
| IL4R | chr16:27325250-27376099 | chr16:26825250-27876099 | chr16:27232751-27283600 | kgp11144142 | kgp16489203 |
| IL5RA | chr3:3108007-3152058 | chr3:2608007-3652058 | chr3:3086420-3127031 | kgp10211459 | kgp22835987 |
| IL8RA | chr2:219027567-219031716 | chr2:218527567-219531716 | chr2:218735812-218739961 | kgp14521358 | rs16859170 |
| INSR | chr19:7112265-7294011 | chr19:6612265-7794011 | chr19:7063265-7245011 | kgp5914741 | kgp21453659 |
| IQCB1 | chr3:121488609-121553926 | chr3:120988609-122053926 | chr3:122971299-123036616 | rs11921531 | rs6438722 |

*Fig. 3-12*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| IQGAP1 | chr15:90931472-91045475 | chr15:90431472-91545475 | chr15:88732476-88846479 | kgp1876985 | kgp20028694 |
| IRAK1 | chrX:153275956-153285342 | chrX:152775956-153785342 | chrX:152929150-152938536 | kgp22756383 | rs6643680 |
| IRS1 | chr2:227596032-227663506 | chr2:227096032-228163506 | chr2:227304276-227371750 | kgp12414080 | kgp9391097 |
| IRS4 | chrX:107975726-107979607 | chrX:107475726-108479607 | chrX:107862367-107866295 | kgp22794644 | rs5985712 |
| ITGB2 | chr21:46305867-46348753 | chr21:45805867-46848753 | chr21:45130296-45173181 | kgp13225366 | rs11702782 |
| ITGB3BP | chr1:63906440-63988944 | chr1:63406440-64488944 | chr1:63679049-63761423 | rs1572109 | kgp5171315 |
| ITGB4 | chr17:73717515-73753899 | chr17:73217515-74253899 | chr17:71229110-71265494 | kgp2663142 | kgp4575494 |
| ITGB5 | chr3:124481794-124606144 | chr3:123981794-125106144 | chr3:125964484-126088834 | kgp5281659 | kgp17765518 |
| ITPKA | chr15:41786055-41795757 | chr15:41286055-42295757 | chr15:39573413-39583039 | kgp22747722 | kgp10507061 |
| ITPKB | chr1:226819390-226926876 | chr1:226319390-227426876 | chr1:224886013-224991987 | rs1219671 | rs7519099 |
| ITPR3 | chr6:33589155-33664348 | chr6:33089155-34164348 | chr6:33697138-33772326 | rs3117030 | kgp4515850 |
| IXL | chr19:39881963-39891203 | chr19:39381963-40391203 | chr19:44573803-44583043 | kgp986483 | kgp6117029 |
| JAK1 | chr1:65298905-65432619 | chr1:64798905-65932619 | chr1:65071493-65205207 | kgp8976721 | kgp9745392 |
| KCNE1 | chr21:35818987-35884573 | chr21:35318987-36384573 | chr21:34740857-34806443 | kgp13187567 | kgp5041106 |
| KCNE4 | chr2:223916861-223920355 | chr2:223416861-224420355 | chr2:223625105-223628599 | kgp14948218 | kgp14631899 |
| KCNH2 | chr7:150642043-150675402 | chr7:150142043-151175402 | chr7:150272981-150305947 | kgp13542655 | kgp7948285 |
| KCNJ2 | chr17:68164813-68176183 | chr17:67664813-68676183 | chr17:65676408-65687778 | rs6501341 | kgp2814913 |
| KCNN2 | chr5:113698015-113832197 | chr5:113198015-114332197 | chr5:113725914-113860096 | kgp9619904 | rs10056549 |
| KCNN4 | chr19:44270684-44285409 | chr19:43770684-44785409 | chr19:48962524-48977249 | rs6509074 | kgp21388839 |
| KCNQ2 | chr20:62037541-62103993 | chr20:61537541-62603993 | chr20:61507985-61574437 | rs16983364 | kgp19265466 |
| KCNQ3 | chr8:133133104-133493004 | chr8:132633104-133993004 | chr8:133210437-133562186 | kgp20244043 | rs4074676 |

*Fig. 3-13*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| KCNQ5 | chr6:73331570-73908573 | chr6:72831570-74408573 | chr6:73388555-73962301 | kgp7790415 | rs9446983 |
| KDR | chr4:55944425-55991762 | chr4:55444425-56491762 | chr4:55639405-55686519 | kgp11624145 | rs10022874 |
| KIAA1377 | chr11:101785745-101871793 | chr11:101285745-102371793 | chr11:101290955-101377003 | kgp12804311 | rs9667864 |
| KIAA1549 | chr7:138516126-138666064 | chr7:138016126-139166064 | chr7:138166666-138255110 | rs11769851 | kgp10209774 |
| KIF3A | chr5:132028322-132073265 | chr5:131528322-132573265 | chr5:132056221-132101164 | rs3805685 | rs4958109 |
| KIT | chr4:55524094-55606881 | chr4:55024094-56106881 | chr4:55218851-55301638 | kgp4467115 | kgp9403472 |
| KLHL20 | chr1:173684079-173755840 | chr1:173184079-174255840 | chr1:171950702-172022463 | rs13374515 | kgp5594942 |
| KLHL3 | chr5:136953188-137071779 | chr5:136453188-137571779 | chr5:136981087-137099678 | rs2966736 | rs10040989 |
| KLK10 | chr19:51515999-51523431 | chr19:51015999-52023431 | chr19:56207811-56215243 | kgp9495392 | kgp21503250 |
| KRAS | chr12:25358179-25403854 | chr12:24858179-25903854 | chr12:25249446-25295121 | kgp19038229 | kgp1316534 |
| KRT10 | chr17:38974368-38978863 | chr17:38474368-39478863 | chr17:36227894-36232373 | kgp7164026 | kgp6621387 |
| KRT18 | chr12:53342654-53346685 | chr12:52842654-53846685 | chr12:51628921-51632952 | rs406857 | rs11834179 |
| LCK | chr1:32716839-32751766 | chr1:32216839-33251766 | chr1:32489426-32524353 | rs12037400 | kgp6229337 |
| LGALS2 | chr22:37966252-37976024 | chr22:37466252-38476024 | chr22:36296198-36305970 | kgp14999686 | rs8135665 |
| LMNA | chr1:156052368-156108548 | chr1:155552368-156608548 | chr1:154318992-154375172 | kgp11675488 | rs12408758 |
| LMNB1 | chr5:126112314-126172712 | chr5:125612314-126672712 | chr5:126140731-126200608 | kgp5014465 | kgp22418220 |
| LOC100133669 | chr8:144063447-144099807 | chr8:143563447-144599807 | chr8:144134822-144171182 | rs10875483 | kgp10850793 |
| LOC154092 | chr6:134758853-134825158 | chr6:134258853-135325158 | chr6:134800546-134866851 | kgp11630779 | kgp22793805 |
| LOC339290 | chr18:5238098-5246505 | chr18:4738098-5746505 | chr18:5222874-5228525 | kgp5290787 | kgp989326 |
| LOC340357 | chr8:12623570-12668910 | chr8:12123570-13168910 | chr8:12667941-12713281 | kgp22754906 | kgp20305069 |
| LOC400604 | chr17:48944039-48945732 | chr17:48444039-49445732 | chr17:46299038-46300731 | kgp11815481 | kgp10163248 |

*Fig. 3-14*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| LOC613126 | chr7:91763906-91771854 | chr7:91263906-92271854 | chr7:91601842-91609790 | kgp13774218 | rs3731343 |
| LTB4R | chr14:24780704-24787242 | chr14:24280704-25287242 | chr14:23850544-23855992 | kgp19673807 | rs8007336 |
| LTF | chr3:46477495-46526724 | chr3:45977495-47026724 | chr3:46452499-46501728 | kgp17788490 | kgp1176589 |
| LXN | chr3:158384202-158390482 | chr3:157884202-158890482 | chr3:159866899-159873176 | rs6764092 | kgp7955381 |
| LYST | chr1:235824344-236030220 | chr1:235324344-236530220 | chr1:233890968-234096843 | rs2295815 | kgp9270301 |
| MAD2L1BP | chr6:43597278-43608688 | chr6:43097278-44108688 | chr6:43705256-43716666 | rs1537638 | kgp1522302 |
| MAGED1 | chrX:51546154-51645450 | chrX:51046154-52145450 | chrX:51562894-51662190 | kgp22779908 | kgp22784919 |
| MAP1A | chr15:43809805-43823818 | chr15:43309805-44323818 | chr15:41597097-41611110 | kgp12180163 | kgp10318377 |
| MAP1LC3A | chr20:33134691-33148149 | chr20:32634691-33648149 | chr20:32598352-32611810 | kgp19388199 | kgp5639543 |
| MAP2K1 | chr15:66679210-66783882 | chr15:66179210-67283882 | chr15:64466264-64570936 | kgp19795142 | kgp382480 |
| MAP2K4 | chr17:11924134-12047051 | chr17:11424134-12547051 | chr17:11864859-11987776 | rs16944942 | rs9915536 |
| MAP2K5 | chr15:67835020-68099455 | chr15:67335020-68599455 | chr15:65622074-65886506 | kgp19854650 | kgp20006731 |
| MAP3K10 | chr19:40697650-40721482 | chr19:40197650-41221482 | chr19:45389490-45413314 | kgp6290284 | rs2561531 |
| MAP3K3 | chr17:61699774-61773670 | chr17:61199774-62273670 | chr17:59053506-59127402 | kgp14048701 | kgp5230870 |
| MAP3K7 | chr6:91225352-91296907 | chr6:90725352-91796907 | chr6:91282073-91353628 | rs9451316 | rs9451576 |
| MAP3K7IP1 | chr22:39745953-39827887 | chr22:39245953-40327887 | chr22:38075899-38157833 | kgp10431646 | rs137981 |
| MAP3K7IP2 | chr6:149639062-149732747 | chr6:149139062-150232747 | chr6:149680755-149774440 | kgp9485571 | kgp9110056 |
| MAP3K8 | chr10:30722949-30750762 | chr10:30222949-31250762 | chr10:30762871-30790767 | kgp22034763 | kgp11496819 |
| MAP6 | chr11:75297962-75379479 | chr11:74797962-75879479 | chr11:74975610-75057127 | rs11236323 | kgp695651 |
| MAPK14 | chr6:35995453-36079013 | chr6:35495453-36579013 | chr6:36103550-36186513 | rs4711420 | kgp10854130 |
| MAPK3 | chr16:30125425-30134630 | chr16:29625425-30634630 | chr16:30032926-30042131 | kgp11463254 | kgp2105557 |

*Fig. 3-15*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| MARCKS | chr6:114178526-114184652 | chr6:113678526-114684652 | chr6:114285219-114291345 | kgp17187839 | kgp1113238 |
| MBP | chr18:74690788-74844774 | chr18:74190788-75344774 | chr18:72819776-72973762 | kgp5208536 | rs12960102 |
| MCC | chr5:112357795-112824527 | chr5:111857795-113324527 | chr5:112385694-112852426 | kgp22530369 | kgp22589538 |
| MGMT | chr10:131265453-131565783 | chr10:130765453-132065783 | chr10:131155455-131455358 | kgp11264334 | kgp1514587 |
| MIP | chr12:56843285-56848435 | chr12:56343285-57348435 | chr12:55130150-55134696 | kgp19052399,rs11834873 | kgp18750923 |
| MLF2 | chr12:6857935-6876641 | chr12:6357935-7376641 | chr12:6728196-6746902 | kgp18998724 | rs1001653 |
| MLLT3 | chr9:20344967-20622514 | chr9:19844967-21122514 | chr9:20334967-20612514 | kgp18504776 | rs1016129 |
| MNAT1 | chr14:61201458-61435398 | chr14:60701458-61935398 | chr14:60271222-60505151 | kgp5293246 | rs7142051 |
| MPHOSPH6 | chr16:82181766-82203829 | chr16:81681766-82703829 | chr16:80739267-80761330 | kgp406017 | rs3852734 |
| MRPS12 | chr19:39421347-39423659 | chr19:38921347-39923659 | chr19:44113187-44115499 | kgp21348524 | kgp21366907 |
| MRPS6 | chr21:35445822-35515334 | chr21:34945822-36015334 | chr21:34367692-34437204 | kgp11037760 | rs2834555 |
| MRVI1 | chr11:10594637-10715535 | chr11:10094637-11215535 | chr11:10551213-10672111 | rs7946995 | kgp11739225 |
| MSN | chrX:64887510-64961793 | chrX:64387510-65461793 | chrX:64804235-64878518 | rs7887705 | kgp22760405 |
| MYF5 | chr12:81110707-81113447 | chr12:80610707-81613447 | chr12:79634838-79637578 | rs12313692 | kgp5599463 |
| MYF6 | chr12:81101407-81103256 | chr12:80601407-81603256 | chr12:79625576-79627382 | rs7954738 | rs7972054 |
| MYLK | chr3:123331142-123603149 | chr3:122831142-124103149 | chr3:124813832-125085839 | kgp9270532 | rs510324 |
| MYO10 | chr5:16662015-16936385 | chr5:16162015-17436385 | chr5:16715015-16989385 | kgp22359577 | kgp12241403 |
| MYO7A | chr11:76839309-76926286 | chr11:76339309-77426286 | chr11:76516957-76603934 | rs2186677 | kgp304899 |
| MYO9B | chr19:17186590-17324104 | chr19:16686590-17824104 | chr19:17047595-17185104 | kgp21430919 | kgp4164870 |
| MYOC | chr1:171604556-171621823 | chr1:171104556-172121823 | chr1:169871179-169888396 | rs1736563 | kgp1482992 |
| MYOD1 | chr11:17741109-17743678 | chr11:17241109-18243678 | chr11:17697685-17700254 | kgp10809253 | rs12285714 |

*Fig. 3-16*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| MYOG | chr1:203052256-203055377 | chr1:202552256-203555377 | chr1:201318879-201322000 | rs4950858 | rs2798625 |
| MYOT | chr5:137022409-137223540 | chr5:136522409-137723540 | chr5:137231472-137251440 | kgp22294838 | kgp5559791 |
| MYT1L | chr2:1792884-2335045 | chr2:1292884-2835045 | chr2:1771891-2314052 | kgp356515 | kgp7720594 |
| NACA | chr12:57106210-57119326 | chr12:56606210-57619326 | chr12:55392477-55405593 | rs4759218 | kgp11483848 |
| NCALD | chr8:102698769-103137135 | chr8:102198769-103637135 | chr8:102767945-103206311 | kgp11277997 | rs16869664 |
| NCF1C | chr7:74572383-74587816 | chr7:74072383-75087816 | chr7:74210380-74225695 | kgp7635479 | kgp954065 |
| NCL | chr2:232319458-232329205 | chr2:231819458-232829205 | chr2:232027702-232037449 | rs13415867 | kgp12447433 |
| NCOR2 | chr12:124808956-125052010 | chr12:124308956-125552010 | chr12:123397062-123617963 | rs11057368 | kgp12274490 |
| NEUROD1 | chr2:182540832-182545392 | chr2:182040832-183045392 | chr2:182249438-182253626 | kgp7038037 | rs12612546 |
| NF2 | chr22:29999544-30094589 | chr22:29499544-30594589 | chr22:28329544-28424589 | kgp15024372 | kgp10478391 |
| NFASC | chr1:204797781-204991950 | chr1:204297781-205491950 | chr1:203064445-203258572 | rs12044614 | kgp11817505 |
| NFATC1 | chr18:77155771-77289323 | chr18:76655771-77789323 | chr18:75256759-75390311 | rs12150804 | kgp11226294 |
| NFATC2 | chr20:50007764-50179168 | chr20:49507764-50679168 | chr20:49441171-49612777 | rs761240 | kgp19325060 |
| NFKB2 | chr10:104154228-104162281 | chr10:103654228-104662281 | chr10:104144218-104152271 | kgp11777223 | rs7897654 |
| NFKBIB | chr19:39390339-39399534 | chr19:38890339-39899534 | chr19:44082454-44091374 | kgp21403480 | kgp4374047 |
| NFKBIE | chr6:44225902-44233525 | chr6:43725902-44733525 | chr6:44333880-44341503 | rs866236 | kgp11221406 |
| NGB | chr14:77731833-77737655 | chr14:77231833-78237655 | chr14:76801586-76807408 | kgp4649405 | rs11622713 |
| NHP2L1 | chr22:42069936-42084913 | chr22:41569936-42584913 | chr22:40399882-40414859 | kgp22806642 | kgp282841 |
| NOS1 | chr12:117645946-117799607 | chr12:117145946-118299607 | chr12:116135361-116283965 | rs11068156 | kgp763518 |
| NP | chr14:20937541-20945248 | chr14:20437541-21445248 | chr14:20007381-20015088 | kgp8768601 | kgp19427360 |
| NPHP1 | chr2:110880913-110962639 | chr2:110380913-111462639 | chr2:110238202-110319928 | rs10496434 | kgp3845148 |

*Fig. 3-17*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| NRBP1 | chr2:27650656-27665124 | chr2:27150656-28165124 | chr2:27504160-27518628 | kgp14600002 | kgp14258181 |
| NRGN | chr11:124609828-124617102 | chr11:124109828-125117102 | chr11:124115038-124122312 | kgp483624 | kgp5783287 |
| NUCB1 | chr19:49403306-49426540 | chr19:48903306-49926540 | chr19:54095380-54118339 | kgp282275 | kgp9015400 |
| OBSCN | chr1:228395860-228566575 | chr1:227895860-229066575 | chr1:226462483-226633198 | kgp22809391 | kgp706951 |
| OGG1 | chr3:9791627-9808353 | chr3:9291627-10308353 | chr3:9765704-9783342 | rs17744749 | rs1642974 |
| OPRK1 | chr8:54138275-54164194 | chr8:53638275-54664194 | chr8:54300828-54326747 | kgp11808605 | kgp7186378 |
| OPRM1 | chr6:154360442-154568001 | chr6:153860442-155068001 | chr6:154402135-154609693 | kgp22790919 | kgp7491549 |
| P2RY1 | chr3:152552735-152555843 | chr3:152052735-153055843 | chr3:154035425-154038533 | rs4472028 | kgp1812100 |
| PA2G4 | chr12:56498102-56507694 | chr12:55998102-57007694 | chr12:54784369-54793961 | kgp18842835 | rs12308290 |
| PABPC4 | chr1:40026484-40042521 | chr1:39526484-40542521 | chr1:39799074-39815003 | rs6692557 | rs6681804 |
| PAEP | chr9:138453603-138458622 | chr9:137953603-138958622 | chr9:137593424-137598443 | kgp4360258 | rs11103302 |
| PAFAH1B1 | chr17:2496922-2588909 | chr17:1996922-3088909 | chr17:2443672-2535659 | kgp13951566 | kgp4861640 |
| PAM | chr5:102201526-102366808 | chr5:101701526-102866808 | chr5:102229425-102393316 | rs10075318 | kgp4660412 |
| PARD6A | chr16:67694850-67696681 | chr16:67194850-68196681 | chr16:66252351-66254182 | kgp16268099,rs1106304 | kgp16328412 |
| PARD6B | chr20:49348080-49370278 | chr20:48848080-49870278 | chr20:48781487-48803685 | kgp19335956 | kgp19356310 |
| PARD6G | chr18:77915116-78005397 | chr18:77415116-78505397 | chr18:76016105-76106388 | kgp15973881 | rs12960632 |
| PAWR | chr12:79985744-80084790 | chr12:79485744-80584790 | chr12:78509875-78608921 | rs2950386 | kgp19124809 |
| PCNT | chr21:47744035-47865682 | chr21:47244035-48365682 | chr21:46568463-46690110 | kgp13165624 | rs10483083 |
| PCP4 | chr21:41239346-41301322 | chr21:40739346-41801322 | chr21:40161216-40223192 | kgp5198475 | rs2837624 |
| PDC | chr1:186412697-186430239 | chr1:185912697-186930239 | chr1:184679337-184696862 | kgp15446019 | kgp15206197 |
| PDCD8 | chrX:129263338-129299861 | chrX:128763338-129799861 | chrX:129091019-129127542 | rs3131260 | kgp22747824 |

*Fig. 3-18*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| PDCL | chr9:125580375-125590935 | chr9:125080375-126090935 | chr9:124620443-124630661 | kgp11050939 | rs7341862 |
| PDE1A | chr2:183007182-183387507 | chr2:182507182-183887507 | chr2:182715427-183095498 | kgp205462 | kgp14271078 |
| PDE4DIP | chr1:144676436-145076186 | chr1:144176436-145576186 | chr1:143388229-143787436 | rs7548928 | kgp15506281 |
| PDE6D | chr2:232597146-232645974 | chr2:232097146-233145974 | chr2:232305390-232354218 | kgp448503 | rs11686328 |
| PDIA2 | chr16:330605-337209 | chr16:1-837209 | chr16:270606-277210 | kgp4861413 | rs3817833 |
| PDLIM7 | chr5:176910394-176924602 | chr5:176410394-177424602 | chr5:176843000-176857208 | kgp10474318 | kgp9286031 |
| PDPK1 | chr16:2587969-2653189 | chr16:2087969-3153189 | chr16:2527970-2593190 | rs11876 | rs2741932 |
| PEA15 | chr1:160175124-160185162 | chr1:159675124-160685162 | chr1:158441750-158451786 | kgp15388960 | kgp4800109 |
| PELO | chr5:52083773-52098452 | chr5:51583773-52598452 | chr5:52119530-52134209 | kgp7417119 | kgp22419632 |
| PFDN1 | chr5:139624634-139682689 | chr5:139124634-140182689 | chr5:139604818-139662873 | kgp2976589 | rs3733707 |
| PFDN4 | chr20:52824501-52836492 | chr20:52324501-53336492 | chr20:52257908-52269899 | kgp2671049 | kgp19401284 |
| PFDN5 | chr12:53689234-53693234 | chr12:53189234-54193234 | chr12:51975501-51979501 | kgp9320945 | kgp18934893 |
| PFKFB2 | chr1:207207760-207254368 | chr1:206707760-207754368 | chr1:205293242-205320991 | rs6666087 | kgp15524399 |
| PFN1 | chr17:4848946-4851825 | chr17:4348946-5351825 | chr17:4789691-4792570 | kgp459103 | rs11869909 |
| PGK1 | chrX:77359665-77382324 | chrX:76859665-77882324 | chrX:77246321-77268980 | kgp22784498 | kgp22747606 |
| PHKA1 | chrX:71798663-71934029 | chrX:71298663-72434029 | chrX:71715388-71850754 | kgp22784635 | kgp22830838,rs5982097 |
| PHKA2 | chrX:18910415-19002480 | chrX:18410415-19502480 | chrX:18820336-18912401 | kgp22820040 | kgp22735291 |
| PHKG1 | chr7:56148674-56160689 | chr7:55648674-56660689 | chr7:56116168-56128183 | rs4947514 | kgp13251786 |
| PIAS4 | chr19:4007748-4038067 | chr19:3507748-4538067 | chr19:3958748-3989067 | kgp21496330 | rs966384 |
| PIK3C3 | chr18:39535198-39661446 | chr18:39035198-40161446 | chr18:37789196-37915444 | kgp16093917 | kgp16001617 |
| PIK3CG | chr7:106505722-106547592 | chr7:106005722-107047592 | chr7:106292958-106334828 | kgp13830163 | kgp58259 |

*Fig. 3-19*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| PLCB2 | chr15:40580097-40600174 | chr15:40080097-41100174 | chr15:38367389-38387466 | rs594863 | kgp19835274 |
| PLCD1 | chr3:38048986-38071154 | chr3:37548986-38571154 | chr3:38023990-38046137 | rs155528 | kgp8999289 |
| PLD1 | chr3:171318194-171528504 | chr3:170818194-172028504 | chr3:172801338-173011198 | kgp17613784 | kgp17918658 |
| PLD2 | chr17:4710395-4726727 | chr17:4210395-5226727 | chr17:4657377-4673694 | rs9915202 | kgp10024037 |
| PLEKHA4 | chr19:49340353-49371884 | chr19:48840353-49871884 | chr19:54032166-54063670 | kgp21466232 | kgp7036888 |
| PLK1 | chr16:23690200-23701688 | chr16:23190200-24201688 | chr16:23597701-23609189 | kgp6012631 | kgp22747639 |
| POLA2 | chr11:65029431-65065088 | chr11:64529431-65565088 | chr11:64786007-64821664 | rs637332 | rs12800057 |
| POLB | chr8:42195972-42229331 | chr8:41695972-42729331 | chr8:42315186-42348470 | kgp20057794 | kgp20541648 |
| POLR2C | chr16:57496550-57505921 | chr16:56996550-58005921 | chr16:56054051-56063422 | kgp12245826 | rs3888264 |
| POLR3F | chr20:18448032-18465286 | chr20:17948032-18965286 | chr20:18396032-18413286 | kgp4834782 | kgp4034265 |
| PPARA | chr22:46546498-46639653 | chr22:46046498-47139653 | chr22:44925162-45018317 | kgp1216941 | kgp15069036 |
| PPEF1 | chrX:18709044-18846034 | chrX:18209044-19346034 | chrX:18618965-18755955 | kgp22764965 | kgp22802655 |
| PPEF2 | chr4:76781025-76823681 | chr4:76281025-77323681 | chr4:77000049-77042705 | kgp3982074 | kgp4693685 |
| PPM1A | chr14:60712469-60765805 | chr14:60212469-61265805 | chr14:59782222-59835559 | kgp19716116 | kgp5849461 |
| PPP1R13B | chr14:104200087-104313927 | chr14:103700087-104813927 | chr14:103269840-103383680 | kgp19713395 | kgp19494408 |
| PPP1R14A | chr19:38741876-38747231 | chr19:38241876-39247231 | chr19:43433716-43439012 | kgp7541975 | kgp4659188 |
| PPP3CA | chr4:101944586-102268628 | chr4:101444586-102768628 | chr4:102163609-102487376 | kgp4575683 | kgp7268908 |
| PPYR1 | chr10:47083533-47088320 | chr10:46583533-47588320 | chr10:46503539-46508326 | kgp507194 | rs11259820 |
| PQBP1 | chrX:48755194-48760422 | chrX:48255194-49260422 | chrX:48640138-48645364 | rs28833838 | rs2015487 |
| PREI3 | chr2:198364721-198418423 | chr2:197864721-198918423 | chr2:198072966-198126668 | kgp9884304 | kgp9480848 |
| PRG2 | chr11:57154833-57191532 | chr11:56654833-57691532 | chr19:763517-772952 | kgp13043879 | kgp12981403 |

Fig. 3-20

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| PRKACA | chr19:14202506-14228559 | chr19:13702506-14728559 | chr19:14063506-14089559 | kgp6577295 | kgp559477 |
| PRKCB1 | chr16:23847300-24231932 | chr16:23347300-24731932 | chr16:23754801-24139433 | rs7190829 | rs2343354 |
| PRKCD | chr3:53195222-53226733 | chr3:52695222-53726733 | chr3:53170262-53201773 | rs11715796 | kgp8788109 |
| PRKCG | chr19:54385466-54410901 | chr19:53885466-54910901 | chr19:59077278-59102713 | kgp1393848 | kgp11043930 |
| PRKCI | chr3:169940219-170023770 | chr3:169440219-170523770 | chr3:171422913-171506464 | kgp17942550 | rs12485248 |
| PRKCZ | chr1:1981908-2116834 | chr1:1481908-2616834 | chr1:1971768-2106694 | kgp15756715 | kgp907107 |
| PRKG1 | chr10:52750910-54058110 | chr10:52250910-54558110 | chr10:52420950-53725280 | kgp22035660 | rs7923443 |
| PSCD2 | chr19:48972465-48985571 | chr19:48472465-49485571 | chr19:53664277-53677383 | rs16981057 | rs5464 |
| PSEN2 | chr1:227058272-227083804 | chr1:226558272-227583804 | chr1:225124895-225150427 | rs3219110 | kgp1301981,rs3014274 |
| PSG9 | chr19:43757434-43773682 | chr19:43257434-44273682 | chr19:48449274-48465522 | kgp21418993 | kgp7929858 |
| PSMA2 | chr7:42956461-42971805 | chr7:42456461-43471805 | chr7:42922986-42938330 | kgp13636285 | kgp8523923 |
| PSMD2 | chr3:184017021-184026840 | chr3:183517021-184526840 | chr3:185499715-185509534 | kgp4284536 | rs11711955 |
| PSPC1 | chr13:20277008-20357159 | chr13:19777008-20857159 | chr13:19146895-19255083 | kgp249471 | kgp2992302 |
| PTGIR | chr19:47123724-47128354 | chr19:46623724-47628354 | chr19:51815564-51820194 | kgp21532737 | rs184290 |
| PTMAP7 | chr2:232573235-232578250 | chr2:232073235-233078250 | chr2:232281479-232286494 | kgp6878597 | kgp14464906 |
| PTP4A1 | chr6:64231650-64293489 | chr6:63731650-64793489 | chr6:64289609-64351448 | rs4710239 | kgp357802 |
| PTP4A3 | chr8:142432006-142441620 | chr8:141932006-142941620 | chr8:142501188-142510802 | rs12678285 | kgp3296894 |
| PTPN11 | chr12:112856535-112947717 | chr12:112356535-113447717 | chr12:111340918-111432100 | kgp22816522 | rs1293743 |
| PTPN12 | chr7:77166772-77269388 | chr7:76666772-77769388 | chr7:77004770-77107322 | kgp4690058 | rs3807707 |
| PTPN6 | chr12:7055739-7070479 | chr12:6555739-7570479 | chr12:6926000-6940740 | kgp18831609 | kgp18845056 |
| PTPRA | chr20:2844824-3019315 | chr20:2344824-3519315 | chr20:2792824-2967315 | kgp725112 | rs2853218 |

*Fig. 3-21*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| PTPRJ | chr11:48002109-48192394 | chr11:47502109-48692394 | chr11:47958685-48148970 | kgp11833163 | kgp12755942 |
| PTPRS | chr19:5158505-5340814 | chr19:4658505-5840814 | chr19:5109505-5291814 | kgp6271833 | kgp4407357 |
| PTPRU | chr1:29563027-29653325 | chr1:29063027-30153325 | chr1:29435633-29525903 | rs12068075 | kgp9719744 |
| RAB27A | chr15:55495163-55582013 | chr15:54995163-56082013 | chr15:53283091-53369293 | kgp19829554 | rs11631355 |
| RAB3B | chr1:52373627-52456436 | chr1:51873627-52956436 | chr1:52157422-52228936 | kgp22830492 | rs10493168 |
| RAB5A | chr3:19988571-20026667 | chr3:19488571-20526667 | chr3:19963762-20001647 | rs1348231 | kgp8738867 |
| RAB8B | chr15:63481727-63559973 | chr15:62981727-64059973 | chr15:61268780-61347026 | kgp20037308 | rs17773778 |
| RABAC1 | chr19:42460832-42463528 | chr19:41960832-42963528 | chr19:47152675-47155311 | kgp22776019 | kgp2186225 |
| RAC1 | chr7:6414125-6443598 | chr7:5914125-6943598 | chr7:6380650-6410123 | kgp13594313 | kgp2338008 |
| RACGAP1 | chr12:50382944-50419307 | chr12:49882944-50919307 | chr12:48669211-48705574 | rs12317050 | kgp2525417 |
| RAF1 | chr3:12625099-12705700 | chr3:12125099-13205700 | chr3:12600099-12680700 | kgp17997932 | kgp3531880 |
| RALB | chr2:120997639-121052286 | chr2:120497639-121552286 | chr2:120726883-120768756 | rs17661862 | kgp5177758 |
| RASSF1 | chr3:50367216-50378367 | chr3:49867216-50878367 | chr3:50342220-50353371 | kgp8151957 | kgp7341826 |
| RBM23 | chr14:23369853-23388396 | chr14:22869853-23888396 | chr14:22439693-22458236 | rs3811239 | kgp128686 |
| RBM5 | chr3:50126340-50156397 | chr3:49626340-50656397 | chr3:49952595-50112488 | kgp22823256 | rs375544 |
| RCVRN | chr17:9801026-9808684 | chr17:9301026-10308684 | chr17:9741751-9749409 | rs8082538 | kgp2141837 |
| REL | chr2:61108751-61150178 | chr2:60608751-61650178 | chr2:60962255-61003682 | kgp8245960 | kgp14294452 |
| RELA | chr11:65421066-65430443 | chr11:64921066-65930443 | chr11:65177647-65186951 | kgp6667058 | kgp4478491 |
| RELB | chr19:45504706-45541456 | chr19:45004706-46041456 | chr19:50196551-50233292 | kgp9280266 | kgp9663255 |
| RFC5 | chr12:118454505-118470042 | chr12:117954505-118970042 | chr12:116938892-116954422 | rs11068526 | kgp19024344 |
| RGS10 | chr10:121259338-121302222 | chr10:120759338-121802222 | chr10:121249328-121292212 | kgp21619652 | kgp5105745 |

*Fig. 3-22*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| RGS13 | chr1:192605267-192629440 | chr1:192105267-193129440 | chr1:190871904-190896012 | rs11806786 | kgp1816960 |
| RGS14 | chr5:176784843-176799599 | chr5:176284843-177299599 | chr5:176717449-176732205 | rs1000144 | kgp11311419 |
| RGS16 | chr1:182567757-182573548 | chr1:182067757-183073548 | chr1:180834380-180840171 | kgp15787070 | kgp4798391 |
| RGS18 | chr1:192127591-192154945 | chr1:191627591-192654945 | chr1:190394214-190421568 | rs1338034 | kgp6525246 |
| RGS19 | chr20:62704534-62711324 | chr20:62204534-63211324 | chr20:62174978-62181768 | rs1630157 | kgp19264714 |
| RGS4 | chr1:163038395-163046592 | chr1:162538395-163546592 | chr1:161305019-161313216 | kgp15623644 | kgp15384575 |
| RGS5 | chr1:163112088-163291581 | chr1:162612088-163791581 | chr1:161378720-161439496 | kgp15331781 | kgp2554099 |
| RGS7 | chr1:240938816-241520478 | chr1:240438816-242020478 | chr1:239005439-239587101 | rs16839692 | kgp15345284 |
| RHO | chr3:129247481-129254187 | chr3:128747481-129754187 | chr3:130730171-130736877 | kgp12236862 | kgp11280524 |
| RHOH | chr4:40198526-40246281 | chr4:39698526-40746281 | chr4:39874921-39922676 | rs3912392 | rs17513557 |
| RIC8A | chr11:208529-215110 | chr11:1-715110 | chr11:198529-205110 | kgp9815230 | rs11246286 |
| RIC8B | chr12:107168398-107283094 | chr12:106668398-107783094 | chr12:105692528-105807224 | kgp7665070 | kgp2084662 |
| RIOK3 | chr18:21032786-21063099 | chr18:20532786-21563099 | chr18:19286784-19317097 | kgp4053645 | kgp16177785 |
| RIPK1 | chr6:3064121-3115421 | chr6:2564121-3615421 | chr6:3009120-3060420 | rs17208835 | kgp17120238 |
| RIPK2 | chr8:90769974-90803292 | chr8:90269974-91303292 | chr8:90839109-90872433 | rs7813237 | rs2214416 |
| RIT1 | chr1:155867600-155881177 | chr1:155367600-156381177 | chr1:154134224-154147801 | kgp10974682 | rs12022607 |
| RIT2 | chr18:40323191-40695657 | chr18:39823191-41195657 | chr18:38577189-38949655 | rs6507465 | kgp3440940 |
| RNF10 | chr12:120972131-121015397 | chr12:120472131-121515397 | chr12:119456514-119499780 | kgp19140786 | kgp19017203 |
| RNF11 | chr1:51701944-51739119 | chr1:51201944-52239119 | chr1:51474532-51511707 | kgp4558813 | kgp7772065 |
| RPL10 | chrX:153627678-153632038 | chrX:153127678-154132038 | chrX:153279911-153283874 | rs2071127 | rs4074307 |
| RPL12 | chr9:130209952-130213711 | chr9:129709952-130713711 | chr9:129249775-129253505 | kgp11622632 | rs3802355 |

*Fig. 3-23*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| RPL37A | chr2:217363519-217366188 | chr2:216863519-217866188 | chr2:217071764-217074433 | kgp2247391 | kgp7636371 |
| RRAD | chr16:66955581-66959439 | chr16:66455581-67459439 | chr16:65513082-65516940 | kgp16522328 | kgp16305055 |
| RTN4 | chr2:55199326-55277734 | chr2:54699326-55777734 | chr2:55052830-55131238 | kgp3749465 | rs3748945 |
| S100A8 | chr1:153362507-153363664 | chr1:152862507-153863664 | chr1:151629131-151630173 | rs6587709 | kgp4686042 |
| SAT1 | chrX:23801274-23804327 | chrX:23301274-24304327 | chrX:23711224-23714248 | kgp22758306 | kgp22759648 |
| SCN8A | chr12:51985019-52202299 | chr12:51485019-52702299 | chr12:50271286-50488566 | rs7979705 | kgp7295633 |
| SDC1 | chr2:20400557-20425194 | chr2:19900557-20925194 | chr2:20264038-20288675 | kgp14253812 | kgp8380770 |
| SDC2 | chr8:97505881-97624037 | chr8:97005881-98124037 | chr8:97575057-97693213 | rs1421221 | kgp1305908 |
| SDC4 | chr20:43953928-43977064 | chr20:43453928-44477064 | chr20:43387342-43410478 | rs8116486 | kgp19276986 |
| SDCBP | chr8:59465727-59495419 | chr8:58965727-59995419 | chr8:59628281-59657973 | rs954172 | kgp20217944 |
| SDCBP2 | chr20:1290554-1373816 | chr20:790554-1873816 | chr20:1238620-1257838 | kgp9852208 | kgp10348674 |
| SDPR | chr2:192699031-192712006 | chr2:192199031-193212006 | chr2:192407280-192420226 | kgp6263901 | kgp14266860 |
| SELENBP1 | chr1:151336779-151345164 | chr1:150836779-151845164 | chr1:149603403-149611788 | rs12406660 | rs6684312 |
| SEMG1 | chr20:43835637-43838414 | chr20:43335637-44338414 | chr20:43269087-43271823 | rs6094023 | rs6094202 |
| SEMG2 | chr20:43835637-43853099 | chr20:43335637-44353099 | chr20:43269087-43286513 | rs6094023 | rs6017667 |
| SEPT4 | chr17:56597610-56618179 | chr17:56097610-57118179 | chr17:53952614-53964410 | kgp1250021 | rs34058624 |
| SETDB1 | chr1:150898814-150937220 | chr1:150398814-151437220 | chr1:149165511-149203837 | rs12759551 | kgp1978717 |
| SGOL1 | chr3:20202084-20227724 | chr3:19702084-20727724 | chr3:20177088-20202687 | kgp9539943 | kgp18040639 |
| SGOL2 | chr2:201390864-201448818 | chr2:200890864-201948818 | chr2:201099186-201156750 | kgp9074393 | kgp14634946 |
| SH2B3 | chr12:111843751-111889427 | chr12:111343751-112389427 | chr12:110328134-110373810 | kgp7682395 | kgp10017505 |
| SHC1 | chr1:154934773-154946959 | chr1:154434773-155446959 | chr1:153201397-153213464 | kgp11196367 | kgp15752431 |

*Fig. 3-24*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| SIRT2 | chr19:39369194-39390502 | chr19:38869194-39890502 | chr19:44061039-44082201 | kgp21526327 | kgp9511717 |
| SLC1A1 | chr9:4490426-4587469 | chr9:3990426-5087469 | chr9:4480443-4577469 | kgp7074545 | kgp9946842 |
| SLC6A9 | chr1:44457171-44497134 | chr1:43957171-44997134 | chr1:44234741-44269721 | rs6687571 | rs6672462 |
| SLC9A3R1 | chr17:72744762-72765499 | chr17:72244762-73265499 | chr17:70256378-70277089 | kgp14032523 | kgp14006779 |
| SMAD3 | chr15:67358194-67487533 | chr15:66858194-67987533 | chr15:65145248-65274587 | kgp1676807 | kgp19813377 |
| SMAD5 | chr5:135468535-135518422 | chr5:134968535-136018422 | chr5:135496434-135546321 | kgp5717445 | kgp8569495 |
| SMN2 | chr5:70220767-70248842 | chr5:69720767-70748842 | chr5:70256523-70284594 | rs28591114 | kgp22633148 |
| SMPD3 | chr16:68392229-68482409 | chr16:67892229-68982409 | chr16:66949730-67039905 | kgp2756941 | kgp16310484 |
| SNAP23 | chr15:42787503-42825259 | chr15:42287503-43325259 | chr15:40575126-40612548 | rs1668586 | kgp19741111 |
| SNAP25 | chr20:10199476-10288066 | chr20:9699476-10788066 | chr20:10147476-10236065 | kgp4923784 | kgp19370207 |
| SNAP91 | chr6:84262604-84419127 | chr6:83762604-84919127 | chr6:84319331-84475831 | kgp17413387 | kgp16958869 |
| SNTA1 | chr20:31995762-32031698 | chr20:31495762-32531698 | chr20:31459423-31495359 | kgp994844 | kgp22753335 |
| SNURF | chr15:25200069-25244225 | chr15:24700069-25744225 | chr15:22751162-22795318 | kgp20028287 | kgp5644000 |
| SOX4 | chr6:21593971-21598849 | chr6:21093971-22098849 | chr6:21701950-21706828 | kgp3609791 | rs9466264 |
| SPAG1 | chr8:101170262-101254132 | chr8:100670262-101754132 | chr8:101239438-101323306 | kgp5198147 | kgp20550876 |
| SPG7 | chr16:89574804-89624174 | chr16:89074804-90124174 | chr16:88102305-88151675 | kgp3688149 | rs3809643 |
| SPP1 | chr4:88896801-88904563 | chr4:88396801-89404563 | chr4:89115825-89123587 | kgp20744622 | kgp20764098 |
| SPTBN1 | chr2:54683453-54898583 | chr2:54183453-55398583 | chr2:54536957-54752087 | kgp14832324 | kgp12300457 |
| SQSTM1 | chr5:179233387-179265077 | chr5:178733387-179765077 | chr5:179170503-179197683 | kgp10101186 | kgp2553327 |
| SRGAP3 | chr3:9022277-9291311 | chr3:8522277-9791311 | chr3:8997277-9266311 | kgp5324812 | kgp18088153 |
| STARD13 | chr13:33677271-34250932 | chr13:33177271-34750932 | chr13:32575306-33148932 | kgp1217969 | kgp9105015 |

Fig. 3-25

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| STC2 | chr5:172741725-172756506 | chr5:172241725-173256506 | chr5:172674331-172689112 | kgp22378380 | kgp10706002 |
| STRN | chr2:37064840-37193615 | chr2:36564840-37693615 | chr2:36928975-37047119 | kgp3533593 | kgp9369923 |
| STRN4 | chr19:47222767-47250251 | chr19:46722767-47750251 | chr19:51914607-51941560 | kgp21470253 | rs4804031 |
| STX4 | chr16:31044415-31051485 | chr16:30544415-31551485 | chr16:30951916-30958986 | kgp16259387 | kgp7678241 |
| STX5 | chr11:62574331-62599563 | chr11:62074331-63099563 | chr11:62330944-62356136 | kgp10937693 | kgp568990 |
| STXBP1 | chr9:130374485-130454995 | chr9:129874485-130954995 | chr9:129414388-129494816 | rs1768374 | kgp4399986 |
| STXBP3 | chr1:109289284-109352148 | chr1:108789284-109852148 | chr1:109090807-109153671 | rs6583070 | rs17036360 |
| SULT1E1 | chr4:70706929-70725870 | chr4:70206929-71225870 | chr4:70741518-70760459 | kgp22798798 | kgp5241292 |
| SUMO4 | chr6:149721494-149722182 | chr6:149221494-150222182 | chr6:149763187-149763875 | rs1871921 | kgp17155476 |
| SYT1 | chr12:79257772-79845788 | chr12:78757772-80345788 | chr12:77781903-78367834 | kgp11848377 | kgp18913198 |
| SYT9 | chr11:7273180-7490276 | chr11:6773180-7990276 | chr11:7229756-7446846 | rs7928685 | kgp8567849 |
| TANC1 | chr2:159825145-160089170 | chr2:159325145-160589170 | chr2:159533391-159797416 | rs4664962 | kgp22743229 |
| TANK | chr2:161993465-162092683 | chr2:161493465-162592683 | chr2:161701711-161800928 | kgp7233899 | rs1006427 |
| TAOK2 | chr16:29985187-30003582 | chr16:29485187-30503582 | chr16:29892722-29911082 | rs257868 | kgp2310172 |
| TBCD | chr17:80709939-80901062 | chr17:80209939-81401062 | chr17:78303228-78494351 | rs11653735 | kgp10867492 |
| TBCE | chr1:235530727-235612280 | chr1:235030727-236112280 | chr1:233597350-233678903 | rs2673969 | kgp15284682 |
| TBK1 | chr12:64845839-64895899 | chr12:64345839-65395899 | chr12:63132203-63182158 | kgp18934034 | kgp19122002 |
| TCF1 | chr5:134240810-134298336 | chr5:133740810-134798336 | chr5:134268709-134326235 | kgp22161149 | kgp4823163 |
| TCF3 | chr19:1609288-1652328 | chr19:1109288-2152328 | chr19:1560294-1603328 | rs2302109 | kgp2427498 |
| TCF4 | chr18:52889561-53303188 | chr18:52389561-53803188 | chr18:51040559-51454183 | kgp10409423 | rs1792746 |
| TDGF1 | chr3:46616044-46623952 | chr3:46116044-47123952 | chr3:46594216-46598956 | kgp980076 | kgp18003873 |

*Fig. 3-26*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| TEP1 | chr14:20833825-20881579 | chr14:20333825-21381579 | chr14:19905765-19951420 | rs1780944 | rs12435821 |
| TERT | chr5:1253286-1295162 | chr5:753286-1795162 | chr5:1306286-1348162 | kgp22831882 | rs4975846 |
| TGFA | chr2:70674411-70781147 | chr2:70174411-71281147 | chr2:70527924-70634613 | kgp14279885 | kgp4236793 |
| TIAM1 | chr21:32490735-32931290 | chr21:31990735-33431290 | chr21:31412606-31853161 | rs1702403 | rs1892577 |
| TM4SF1 | chr3:149086804-149095568 | chr3:148586804-149595568 | chr3:150569494-150578258 | kgp18120845 | kgp17746361 |
| TMSB4X | chrX:12993225-12995346 | chrX:12493225-13495346 | chrX:12903145-12905267 | kgp22760889 | kgp22772999 |
| TNFRSF14 | chr1:2487804-2495267 | chr1:1987804-2995267 | chr1:2479150-2486613 | rs2803309 | kgp11439882 |
| TNFRSF1A | chr12:6437922-6451283 | chr12:5937922-6951283 | chr12:6308183-6321522 | kgp6731378,rs4764519 | kgp19158534 |
| TNFRSF1B | chr1:12227059-12269277 | chr1:11727059-12769277 | chr1:12149646-12191864 | kgp15495881 | rs3010872 |
| TNIP2 | chr4:2743386-2758103 | chr4:2243386-3258103 | chr4:2713184-2727859 | kgp20948263 | kgp5432833 |
| TNNI2 | chr11:1860232-1862910 | chr11:1360232-2362910 | chr11:1817480-1819484 | kgp11231095 | rs800123 |
| TNNI3 | chr19:55663135-55669100 | chr19:55163135-56169100 | chr19:60354947-60360912 | rs13382124 | kgp21397937 |
| TNNT2 | chr1:201328141-201346805 | chr1:200828141-201846805 | chr1:199594764-199613428 | rs12733378 | rs10920269 |
| TOMM20 | chr1:235272657-235292256 | chr1:234772657-235792256 | chr1:233339282-233358754 | kgp8358331 | kgp15139309 |
| TOP2A | chr17:38544772-38574202 | chr17:38044772-39074202 | chr17:35798321-35827695 | kgp7375263 | kgp10420460 |
| TP53 | chr17:7571719-7590863 | chr17:7071719-8090863 | chr17:7512444-7531588 | kgp12029669 | kgp11286494 |
| TRADD | chr16:67188088-67193812 | chr16:66688088-67693812 | chr16:65745589-65751313 | kgp16482196 | kgp16510307,rs28521023 |
| TRAF1 | chr9:123664670-123691451 | chr9:123164670-124191451 | chr9:122704492-122731300 | kgp6551598 | rs306777 |
| TRAF6 | chr11:36505316-36531863 | chr11:36005316-37031863 | chr11:36467298-36488398 | kgp12764289 | rs333778 |
| TRBV21-1 | chr7:142344427-142344887 | chr7:141844427-142844887 | chr7:142025416-142025876 | kgp2155197 | kgp9570297 |
| TRIM2 | chr4:154074269-154260474 | chr4:153574269-154760474 | chr4:154293719-154479918 | rs6849505 | rs6843172 |

*Fig. 3-27*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| TRIM29 | chr11:119981993-120008863 | chr11:119481993-120508863 | chr11:119487203-119514073 | kgp12998914 | rs7122702 |
| TRIO | chr5:14143828-14509458 | chr5:13643828-15009458 | chr5:14196828-14562458 | rs1445678 | kgp8041369 |
| TRPC1 | chr3:142443265-142526729 | chr3:141943265-143026729 | chr3:143925955-144009419 | rs9842771 | rs7641069 |
| TRPC3 | chr4:122800182-122872909 | chr4:122300182-123372909 | chr4:123019881-123092359 | kgp21231448 | kgp5789583 |
| TRPC4 | chr13:38210772-38443939 | chr13:37710772-38943939 | chr13:37108794-37341935 | kgp22792521 | rs7338958 |
| TRPV1 | chr17:3468739-3512705 | chr17:2968739-4012705 | chr17:3415489-3459454 | kgp8654960 | rs9890881 |
| TRPV4 | chr12:110220891-110271212 | chr12:109720891-110771212 | chr12:108705276-108755595 | kgp11365980 | kgp19139284 |
| TRPV6 | chr7:142568959-142583490 | chr7:142068959-143083490 | chr7:142279081-142293599 | kgp9647465 | kgp2837315 |
| TSC22D4 | chr7:100064141-100076902 | chr7:99564141-100576902 | chr7:99902077-99914838 | kgp5759639 | kgp10599319 |
| TSHR | chr14:81421868-81612646 | chr14:80921868-82112646 | chr14:80491621-80682399 | kgp19546597 | rs10134565 |
| TSPAN6 | chrX:99883794-99891794 | chrX:99383794-100391794 | chrX:99770450-99778450 | kgp22794008 | rs7059563 |
| TTBK1 | chr6:43211221-43255997 | chr6:42711221-43755997 | chr6:43319199-43363975 | kgp17369454 | kgp17498760 |
| TTC1 | chr5:159436179-159492550 | chr5:158936179-159992550 | chr5:159368757-159425128 | kgp5018309 | kgp22489460 |
| TTK | chr6:80714321-80752244 | chr6:80214321-81252244 | chr6:80771077-80808958 | kgp949561 | kgp12311980 |
| TTN | chr2:179390717-179672150 | chr2:178890717-180172150 | chr2:179098963-179380395 | rs959775 | rs6433773 |
| TUB | chr11:8040790-8127654 | chr11:7540790-8627654 | chr11:8016755-8084228 | kgp12365126 | kgp1066384 |
| TUBA8 | chr22:18593452-18614498 | chr22:18093452-19114498 | chr22:16940685-16994498 | rs1034470 | kgp9877961 |
| UBE2V2 | chr8:48920994-48974454 | chr8:48420994-49474454 | chr8:49083547-49137007 | kgp3293751 | kgp20374954 |
| ULK1 | chr12:132379278-132407707 | chr12:131879278-132907707 | chr12:130945231-130973649 | kgp7696078 | kgp11815104 |
| USP7 | chr16:8985950-9057341 | chr16:8485950-9557341 | chr16:8893451-8964842 | kgp79060 | rs1035944 |
| VAV1 | chr19:6772721-6857371 | chr19:6272721-7357371 | chr19:6723721-6808371 | kgp21410647 | kgp21471951 |

Fig. 3-28

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| VCL | chr10:75754950-75879914 | chr10:75254950-76379914 | chr10:75424956-75549920 | rs7099640 | kgp21840278 |
| VDAC1 | chr5:133307565-133340824 | chr5:132807565-133840824 | chr5:133335505-133368723 | kgp22321002 | kgp9499928 |
| VIL2 | chr6:159186773-159239340 | chr6:158686773-159739340 | chr6:159106761-159159328 | rs9366083 | kgp10633571 |
| VIM | chr10:17270257-17279592 | chr10:16770257-17779592 | chr10:17310475-17319598 | kgp1974218 | kgp8572563 |
| VTN | chr17:26694298-26697373 | chr17:26194298-27197373 | chr17:23718425-23721500 | rs12602762 | kgp2208161 |
| WDR62 | chr19:36545782-36596012 | chr19:36045782-37096012 | chr19:41237622-41287852 | kgp5818871 | kgp7464156 |
| WDR91 | chr7:134868589-134896316 | chr7:134368589-135396316 | chr7:134520524-134546811 | kgp7394785 | kgp4752834 |
| WWC1 | chr5:167719064-167899308 | chr5:167219064-168399308 | chr5:167651669-167829342 | rs10454965 | rs7724207 |
| XK | chrX:37545132-37591383 | chrX:37045132-38091383 | chrX:37430051-37476322 | kgp22781551 | kgp22821350 |
| YWHAB | chr20:43514343-43537161 | chr20:43014343-44037161 | chr20:42947757-42970575 | rs4364072 | rs2247619 |
| YWHAE | chr17:1247833-1303556 | chr17:747833-1803556 | chr17:1194592-1250267 | rs4968122 | kgp1552188 |
| YWHAG | chr7:75956107-75988342 | chr7:75456107-76488342 | chr7:75794051-75826252 | kgp13357645 | kgp7952605 |
| YWHAZ | chr8:101930803-101965623 | chr8:101430803-102465623 | chr8:102000089-102034745 | rs4075553 | kgp4135753 |
| ZNF24 | chr18:32912177-32924426 | chr18:32412177-33424426 | chr18:31166175-31178424 | kgp5227729 | kgp15931312 |

*Fig. 3-29*

NONSELECTIVE METABOTROPIC GLUTAMATE RECEPTOR ACTIVATORS FOR TREATMENT OF ATTENTION DEFICIT DISORDER AND 22Q SYNDROME

CROSS-REFERENCE TO RELATED APPLICATIONS

This application is a continuation of U.S. patent application Ser. No. 15/850,307, filed on Dec. 21, 2017, now U.S. Pat. No. 10,869,861, which is a divisional of U.S. patent application Ser. No. 15/258,828, now U.S. Pat. No. 9,884,057, filed Sep. 7, 2016, which claims priority to the following four United States Provisional Patent Applications, each filed on Sep. 8, 2015: 62/215,628; 62/215,633; 62/215,636; and 62/215,673, each of which is incorporated herein by reference in its entirety.

FIELD

This application relates to treating attention deficit hyperactivity disorder (ADHD) and 22q syndrome with a nonselective activator of metabotropic glutamate receptors, for example, in subjects having a genetic alteration in at least one metabotropic glutamate receptor (mGluR) network gene.

BACKGROUND

Attention deficit hyperactivity disorder (ADHD) is a neurodevelopmental disorder that may cause significant impairment in childhood and later life. Symptoms of ADHD include inattentiveness, hyperactivity, and impulsivity.

We previously conducted a large-scale, genome-wide study comparing copy number variations (CNVs) in about 3500 ADHD cases compared to about 13,000 controls, and found that CNVs in genes coding for metabotropic glutamate receptors (mGluR proteins or GRM genes) as well as CNVs in genes coding for proteins that interact with mGluRs occur significantly more frequently in ADHD cases compared to controls. (See WO 2012/027491 and US 2013/0203814; Elia et al., Nature Genetics, 44(1): 78-84 (2012).) The frequency of each individual genetic alteration appears to be quite rare. But collectively, about 11% or more of ADHD cases compared to about 1% of controls have at least one genetic alteration in a gene coding for an mGluR network protein. Thus, ADHD patients are about 10 times more likely than control individuals to have a genetic alteration affecting one or more mGluR network genes. Furthermore, a network analysis of the mGluR pathway in the European American population of approximately 1000 cases and 4000 controls showed that copy number variations (CNVs) in genes coding for proteins involved in mGluR signaling pathways and their interacting proteins impact about 20% of ADHD cases compared to controls.

There is no cure for ADHD, but the symptoms can be managed by combinations of behavior therapy and medications. Currently approved therapeutics for ADHD include several stimulant and non-stimulant drugs. Current medications are not ideal, especially stimulants, because they have a number of possibly harmful side effects and have short half-lives of activity. Moreover, stimulants are often misused and abused by qualifying and non-qualifying patients alike. Hence, additional ADHD medications are needed. In addition, given the genetic heterogeneity of ADHD patients, tailoring certain medication schemes to patients based on their underlying genetic profile may also improve ADHD treatment.

The inventors have conducted a clinical trial testing a nonselective activator of mGluR proteins called NFC-1 or fasoracetam monohydrate in pediatric ADHD patients who have at least one genetic alteration in a gene coding for an mGluR network protein.

This trial also included ADHD patients who have 22q syndromes, which are characterized by either a deletion (22q deletion syndrome) or duplication (22q duplication syndrome) in the 22q11.2 region of chromosome 22. Those syndromes may occur in at least about 1 out of every 2000-4000 children and may involve disruptions in as many as 30-40 genes. Among the genes that may be affected is RANBP1, an mGluR network gene. Children with a deletion or duplication at 22q11.2 have a higher than average rate of psychiatric disorders including ADHD, autism spectrum (ASD), and anxiety disorder, and a significant percentage may develop psychoses such as schizophrenia later in life. Children with a deletion or duplication of that region may also suffer from various intellectual disabilities.

Treatment of psychiatric symptoms in 22q syndrome patients may be complicated due to the physical abnormalities of these patients, including cardiac anomalies. For example, it may be necessary to avoid use of otherwise widely-prescribed stimulant drugs due to their negative side effects in the 22q syndrome population. Thus, improved therapeutic treatments are particularly needed for patients with ADHD, ASD, anxiety disorder or other conditions who have an underlying 22q genetic syndrome.

SUMMARY

Provided herein are methods of treating attention deficit hyperactivity disorder (ADHD) in a subject comprising administering a therapeutically effective amount of a nonselective metabotropic glutamate receptor (mGluR) activator to a subject, thereby treating ADHD.

Also provided are methods of treating attention deficit hyperactivity disorder (ADHD) in a subject comprising administering a therapeutically effective amount of a nonselective metabotropic glutamate receptor (mGluR) activator to a subject having at least one genetic alteration in an mGluR network gene, thereby treating ADHD.

Further provided herein are methods of treating ADHD in a subject comprising administering a nonselective mGluR activator to a subject with ADHD in an amount or dosage regime shown to be effective to result in a clinical general impression—improvement (CGI-I) score of 1 or 2 after at least four weeks of treatment and/or an improvement of at least 25%, such as at least 30%, at least 35%, or at least 40%, in an ADHD rating scale score after at least four weeks of treatment in a majority of subjects of at least one clinical trial.

In some embodiments, the subject has genetic alterations in at least one mGluR network gene. In some embodiments, the subject has genetic alterations in at least two mGluR network genes.

In some embodiments, the subject is a pediatric or adolescent subject, such as a subject between the ages of 5 and 17, 8 and 17, 5 and 12, 5 and 8, 8 and 12, 12 and 18, 13 and 18, or 12 and 17. In other embodiments, the subject is an adult.

In some embodiments, the nonselective mGluR activator is fasoracetam, such as fasoracetam monohydrate (NFC-1).

In some embodiments where the activator is fasoracetam, the fasoracetam is administered at a dose of 50-400 mg, such as 100-400 mg, or 100-200 mg, or 200-400 mg, or 100 mg, or 200 mg, or 300 mg, or 400 mg, and the dose is administered once, twice, or three times daily. In some embodiments, the fasoracetam is administered at a dose of 100 mg, 200 mg, 300 mg, or 400 mg twice daily, such as 100-200 mg twice daily.

In some embodiments, of the ADHD treatment methods above, the activator is administered in combination with a stimulant, such as methylphenidate, dexmethylphenidate, amphetamine, dextroamphetamine, or lisdexamphetamine; and/or in combination with a nonstimulant, such as atomoxetine, clonidine, or guanfacine; and/or in combination with an antidepressant, such as fluoxetine, escitalopram, bupropion, mirtazapine, amitriptyline, imipramine, venlafaxine, sertraline, paroxetine, tricyclic antidepressants, selective serotonin reuptake inhibitors, serotonin and norepinephrine reuptake inhibitors, norepinephrine and dopamine reuptake inhibitors, or monoamine oxidase inhibitors; and/or in combination with an anxiolytic, such as barbiturates, pregabalin, or benzodiazepines, including chlordiazepoxide, clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam; and/or in combination with an anti-psychotic, such as aripiprazole or risperidone; and/or in combination with a beta blocker, such as acebutolol, atenolol, betaxolol, bisoprolol, esmolol, nebivolol, metoprolol, cartelol, penbutolol, pindolol, carvedilol, labetalol, levobunolol, metipranolol, nadolol, propranolol, sotalol, or timolol.

In some embodiments, the activator is administered in combination with non-pharmaceutical therapy, such as brain stimulation, for example vagus nerve stimulation, repetitive transcranial magnetic stimulation, magnetic seizure therapy, and/or deep brain stimulation.

In some embodiments, the ADHD subject has at least one co-morbid phenotype or condition such as oppositional defiant disorder (ODD), anxiety disorder, conduct disorder, Tourette's syndrome, autism, difficulty controlling anger, disruptive behavior, obsessive compulsive disorder (OCD), dermatillomania, a developmental disorder, or a movement disorder. In some embodiments, the ADHD subject has 22q deletion or duplication syndrome. In some embodiments, the subject does not have at least one or does not have any of ODD, anxiety disorder, conduct disorder, Tourette's syndrome, autism, 22q deletion or duplication syndrome, difficulty controlling anger, disruptive behavior, obsessive compulsive disorder (OCD), dermatillomania, a developmental disorder, or a movement disorder. In some embodiments, the subject has ODD. In some such embodiments, the method treats ODD in the subject, for example by reducing symptoms of argumentativeness and defiance, vindictiveness, and/or anger and irritability. In some embodiments, the ADHD subject has a co-morbid phenotype such as a mood disorder or sleep disorder such as insomnia. In some cases, the method treats the mood or sleep disorder, such as by reducing its symptoms. In some embodiments, the subject has a co-morbid symptom such as difficultly controlling anger and/or disruptive behavior. In some cases, the method reduces one or both of those symptoms. In some embodiments, the subject has co-morbid symptoms of anxiety and in some cases, the method reduces anxiety symptoms. In some embodiments, the subject has OCD and in some cases, the method reduces OCD symptoms. In some cases, the subject has co-morbid symptoms of dermatillomania, such as excessive skin picking, and the method reduces those symptoms. In some embodiments, the subject has one or more co-morbid developmental disorders, and in some cases, the method reduces the severity of symptoms related to the developmental disorders.

In some embodiments, the methods may reduce behavioral symptoms of ADHD such as inattentiveness, hyperactivity, and/or impulsiveness. In some embodiments, the methods also comprise assessing symptoms such as inattentiveness, hyperactivity, and/or impulsiveness during or after administration, for example, to determine if one or more of those symptoms have been reduced in the subject. In some methods, such assessment may be performed based on an ADHD rating scale or based on a clinical global impression (CGI) scale, e.g. a CGI-severity or CGI-improvement scale. For example, in some embodiments, the methods further comprise obtaining a clinical global impression of severity or improvement for the subject during or after administration. In some embodiments, the methods may improve clinical global improvement scores and/or ADHD rating scale scores in the subject. In some cases, symptoms may be reduced after at least 1 week, at least 2 weeks, at least 3 weeks, or at least 4 weeks of treatment with the activator.

In some embodiments of the above ADHD treatment methods, the subject has at least one genetic alteration in an mGluR network gene, such as a point mutation, insertion, deletion, or copy number variation (CNV). In some embodiments, the subject has a genetic alteration in two or more mGluR network genes. In some embodiments, the genetic alteration is detected by a process comprising a genetic test comprising obtaining a sample from the subject, optionally isolating nucleic acid from the sample, optionally amplifying the nucleic acid, and analyzing the nucleic acid for a genetic alteration in at least one mGluR network gene.

In some embodiments, the treatment method further comprises obtaining results of the genetic test prior to initial administration of the activator. In some embodiments, the genetic test comprises analyzing the nucleic acid for a CNV or SNV in at least 5, 6, 7, 8, 9, 10, 15, 20, 30, 40, 50, 60, 70, or all Tier 1 mGluR network genes (FIG. 1 herein).

In some embodiments, the genetic test comprises analyzing the nucleic acid for a CNV or SNV in at least 5, 10, 20, 30, 50, 100, 150, 175, or all Tier 2 mGluR network genes (FIG. 2). In some embodiments, the method comprises analyzing the nucleic acid for a CNV or SNV in at least 5, 10, 20, 50, 100, 200 300, 400, 500, or all Tier 3 mGluR network genes (FIG. 3). In some embodiments, the genetic test does not assess CNVs or SNVs in one or more of GRM1, GRM2, GRM3, GRM4, GRM5, GRM6, GRM7 or GRM8. In some embodiments, the subject does not have a CNV or SNV in one or more of GRM1, GRM2, GRM3, GRM4, GRM5, GRM6, GRM7 or GRM8.

Further provided herein is a method of treating ADHD in a subject comprising administering fasoracetam to the subject at a dose of 50-400 mg, such as 100-400 mg, or 100-200 mg, or 200-400 mg, or 100 mg, or 200 mg, or 300 mg, or 400 mg, wherein the dose is administered once, twice, or three times daily, thereby treating ADHD. In some such embodiments, the fasoracetam is administered at a dose of 100 mg, 200 mg, 300 mg, or 400 mg twice daily, such as 100-200 mg twice daily.

In some embodiments of the above ADHD treatment methods, the subject has at least one genetic alteration in an mGluR network gene, such as a point mutation, insertion, deletion, single nucleotide variation (SNV) or copy number variation (CNV). In some embodiments, the subject has a genetic alteration in two or more mGluR network genes. In some embodiments, the genetic alteration is detected by a process comprising a genetic test comprising obtaining a sample from the subject, optionally isolating nucleic acid from the sample, optionally amplifying the nucleic acid, and analyzing the nucleic acid for a genetic alteration in at least one mGluR network gene.

In some embodiments, the treatment method further comprises obtaining results of the genetic test prior to initial administration of the activator. In some embodiments, the genetic test comprises analyzing the nucleic acid for a CNV or SNV in at least 5, 6, 7, 8, 9, 10, 15, 20, 30, 40, 50, 60, 70, or all Tier 1 mGluR network genes (FIG. 1 herein). In some embodiments, the genetic test comprises analyzing the nucleic acid for a CNV or SNV in at least 5, 10, 20, 30, 50, 100, 150, 175, or all Tier 2 mGluR network genes (FIG. 2).

In some embodiments, the method comprises analyzing the nucleic acid for a CNV or SNV in at least 5, 10, 20, 50, 100, 200 300, 400, 500, or all Tier 3 mGluR network genes (FIG. 3). In some embodiments, the genetic test does not assess CNVs or SNVs in one or more of GRM1, GRM2, GRM3, GRM4, GRM5, GRM6, GRM7 or GRM8.

In some embodiments, the ADHD subject has a genetic alteration, such as a CNV, in a Tier 1 or Tier 2 mGluR network gene but does not have a genetic alteration, such as a CNV, in a Tier 3 mGluR network gene. In some embodiments, the test utilizes a solid support, microarray, or chip containing appropriate probes to detect the presence of CNVs and/or SNVs in the genes.

In some embodiments, the subject is a pediatric or adolescent subject, such as a subject between the ages of 5 and 17, 8 and 17, 5 and 12, 5 and 8, 8 and 12, 12 and 18, 13 and 18, or 12 and 17. In other embodiments, the subject is an adult.

In some embodiments, the fasoracetam is administered in combination with a stimulant, such as methylphenidate, dexmethylphenidate, amphetamine, dextroamphetamine, or lisdexamphetamine; and/or in combination with a nonstimulant, such as atomoxetine, clonidine, or guanfacine; and/or in combination with an antidepressant, such as fluoxetine, escitalopram, bupropion, mirtazapine, amitriptyline, imipramine, venlafaxine, sertraline, paroxetine, tricyclic antidepressants, selective serotonin reuptake inhibitors, serotonin and norepinephrine reuptake inhibitors, norepinephrine and dopamine reuptake inhibitors, or monoamine oxidase inhibitors; and/or in combination with an anxiolytic, such as barbiturates, pregabalin, or benzodiazepines, including chlordiazepoxide, clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam; and/or in combination with an anti-psychotic, such as aripiprazole or risperidone; and/or in combination with a beta blocker, such as acebutolol, atenolol, betaxolol, bisoprolol, esmolol, nebivolol, metoprolol, cartelol, penbutolol, pindolol, carvedilol, labetalol, levobunolol, metipranolol, nadolol, propranolol, sotalol, or timolol.

In some embodiments, the fasoracetam is administered in combination with non-pharmaceutical therapy, such as brain stimulation, for example vagus nerve stimulation, repetitive transcranial magnetic stimulation, magnetic seizure therapy, and/or deep brain stimulation.

In some embodiments, the ADHD subject has at least one co-morbid phenotype or condition such as oppositional defiant disorder (ODD), anxiety disorder, conduct disorder, Tourette's syndrome, autism, difficulty controlling anger, disruptive behavior, 22q deletion or duplication syndrome, difficulty controlling anger, disruptive behavior, obsessive compulsive disorder (OCD), dermatillomania, a developmental disorder, or a movement disorder. In some embodiments, the subject does not have at least one or does not have any co-morbid phenotype such as ODD, anxiety disorder, conduct disorder, Tourette's syndrome, autism, difficulty controlling anger, disruptive behavior, 22q deletion or duplication syndrome, difficulty controlling anger, disruptive behavior, obsessive compulsive disorder (OCD), dermatillomania, a developmental disorder, or a movement disorder.

In some embodiments, the subject has ODD. In some such embodiments, the method treats ODD in the subject, for example by reducing symptoms of argumentativeness and defiance, vindictiveness, and/or anger and irritability. In some embodiments, the subject has ODD and ADHD.

In some embodiments, the ADHD subject has a co-morbid phenotype such as a mood disorder or sleep disorder such as insomnia. In some cases, the method treats the mood or sleep disorder, such as by reducing its symptoms. In some embodiments, the subject has co-morbid symptoms of anxiety and in some cases, the method reduces anxiety symptoms. In some embodiments, the subject has OCD and in some cases, the method reduces OCD symptoms. In some cases, the subject has co-morbid symptoms of dermatillomania, such as excessive skin picking, and the method reduces those symptoms. In some embodiments, the subject has one or more co-morbid developmental disorders, and in some cases, the method reduces the severity of symptoms related to the developmental disorders.

For example, in some embodiments, the methods may reduce behavioral symptoms of ADHD such as inattentiveness, hyperactivity, and/or impulsiveness. In some embodiments, the methods also comprise assessing symptoms such as inattentiveness, hyperactivity, and/or impulsiveness during or after administration, for example, to determine if one or more of those symptoms have been reduced in the subject. In some methods, such assessment may be performed based on an ADHD rating scale or based on a clinical global impression (CGI) scale, e.g. a CGI-severity or CGI-improvement scale. For example, in some embodiments, the methods further comprise obtaining a clinical global impression of severity or improvement for the subject during or after administration. In some cases, symptoms may be reduced after at least 1 week, at least 2 weeks, at least 3 weeks, or at least 4 weeks of treatment with the activator.

In some embodiments, the methods may improve clinical global improvement scores and/or ADHD rating scale scores in the subject. For example, in any of the above ADHD treatment methods, the subject may have one or more of the following changes in symptoms after at least one, two, three, or four weeks of treatment with the activator: (a) the subject has symptoms of anger control and the anger control symptoms are reduced; (b) the subject has symptoms of disruptive behavior and the disruptive behavior symptoms are reduced; (c) the subject's CGI-I is reduced by at least 1 or by at least 2; (d) the subject's CGI-I score after one, two, three, or four weeks of treatment is 1 or 2; (e) the subject's CGI-S score after one, two, three, or four weeks of treatment is 1; (f) the subject's ADHD Rating Scale score is reduced by at least 25%, such as at least 30%, at least 35%, or at least 40%; (g) the subject has symptoms of inattentiveness and the inattentiveness symptoms are reduced; (h) the subject has symptoms of hyperactivity and the hyperactivity symptoms are reduced; (i) the subject has symptoms of impulsiveness and the impulsiveness symptoms are reduced; (j) the subject has symptoms of ODD such as anger and irritability, argumentation and defiance, and/or vindictiveness and the ODD symptoms are reduced; (k) the subject has symptoms of conduct disorder and the conduct disorder symptoms are reduced; (l) the subject has symptoms of anxiety and the anxiety symptoms are reduced; (m) the subject has symptoms of Tourette's syndrome, and the Tourette's syndrome symptoms are reduced; (n) the subject has symptoms of autism, and the autism symptoms are reduced; and (o) the subject has symptoms of movement disorder and the movement disorder symptoms are reduced.

In some embodiments where the ADHD subject has at least one genetic alteration in an mGluR network gene, the genetic alteration is detected by a process comprising a genetic test comprising obtaining a sample from the subject, optionally isolating nucleic acid from the sample, optionally amplifying the nucleic acid, and analyzing the nucleic acid for a genetic alteration in at least one mGluR network gene.

In some embodiments, the treatment method further comprises obtaining results of the genetic test prior to initial administration of the activator. In some embodiments, the genetic test comprises analyzing the nucleic acid for a CNV or SNV in at least 5, 6, 7, 8, 9, 10, 15, 20, 30, 40, 50, 60, 70, or all Tier 1 mGluR network genes (FIG. 1 herein).

In some embodiments, the genetic test comprises analyzing the nucleic acid for a CNV or SNV in at least 5, 10, 20, 30, 50, 100, 150, 175, or all Tier 2 mGluR network genes (FIG. 2). In some embodiments, the method comprises analyzing the nucleic acid for a CNV or SNV in at least 5, 10, 20, 50, 100, 200 300, 400, 500, or all Tier 3 mGluR network genes (FIG. 3).

In some embodiments, the genetic test does not assess CNVs or SNVs in one or more of GRM1, GRM2, GRM3, GRM4, GRM5, GRM6, GRM7 or GRM8. In some embodiments, the subject does not have a CNV or SNV in one or more of GRM1, GRM2, GRM3, GRM4, GRM5, GRM6, GRM7 or GRM8. In some embodiments, the ADHD subject has a genetic alteration, such as a CNV, in a Tier 1 or Tier 2 mGluR network gene but does not have a genetic alteration, such as a CNV, in a Tier 3 mGluR network gene.

Also provided herein are methods of treating 22q syndrome in a subject comprising administering an effective amount of a nonselective metabotropic glutamate receptor (mGluR) activator to a subject with 22q syndrome, thereby treating 22q syndrome. In some embodiments, the subject has a genetic alteration, such as a point mutation, insertion, deletion, or copy number variation (CNV) in the gene RANBP1. For example, the subject may have a deletion or a duplication at 22q11.2, i.e. a 22q deletion or 22q duplication syndrome. In some embodiments, provided methods comprise treating 22q deletion syndrome in a subject comprising administering an effective amount of a nonselective metabotropic glutamate receptor (mGluR) activator to a subject with 22q deletion syndrome, thereby treating 22q deletion syndrome.

In some embodiments, provided methods comprise treating 22q duplication syndrome in a subject comprising administering an effective amount of a nonselective metabotropic glutamate receptor (mGluR) activator to a subject with 22q duplication syndrome, thereby treating 22q deletion syndrome. In some embodiments, the subject has a genetic alteration in RANBP1 and in at least one further mGluR network gene, such as a Tier 1, Tier 2, or Tier 3 gene as disclosed herein in FIGS. 1-3. In some embodiments, the subject does not have a CNV or a single nucleotide variation (SNV) in one or more of GRM1, GRM2, GRM3, GRM4, GRM5, GRM6, GRM7 or GRM8.

In some embodiments, the 22q syndrome subject has attention deficit hyperactivity disorder (ADHD), and treating the subject may comprise treating the ADHD, such as alleviating at least one ADHD symptom in the subject, including include inattentiveness, hyperactivity, and impulsivity. In some embodiments, the subject is a pediatric or adolescent subject, such as a subject between the ages of 5 and 17, 8 and 17, 5 and 12, 5 and 8, 8 and 12, 12 and 18, 13 and 18, or 12 and 17. In other embodiments, the subject is an adult.

In some embodiments, the nonselective mGluR activator is fasoracetam, such as fasoracetam monohydrate (NFC-1).

In some embodiments where the activator is fasoracetam, the fasoracetam is administered at a dose of 50-400 mg, such as 100-400 mg, or 100-200 mg, or 200-400 mg, or 100 mg, or 200 mg, or 300 mg, or 400 mg, and is administered once, twice, or three times daily. In some embodiments, the fasoracetam is administered at a dose of 100 mg, 200 mg, 300 mg, or 400 mg twice daily, such as 100-200 mg twice daily.

In some embodiments, the activator is administered in combination with another pharmaceutical agent, such as a stimulant, such as methylphenidate, dexmethylphenidate, amphetamine, dextroamphetamine, or lisdexamphetamine; and/or in combination with a nonstimulant, such as atomoxetine, clonidine, or guanfacine; and/or in combination with an antidepressant, such as fluoxetine, escitalopram, bupropion, mirtazapine, amitriptyline, imipramine, venlafaxine, sertraline, paroxetine, tricyclic antidepressants, selective serotonin reuptake inhibitors, serotonin and norepinephrine reuptake inhibitors, norepinephrine and dopamine reuptake inhibitors, or monoamine oxidase inhibitors; and/or in combination with an anxiolytic, such as barbiturates, pregabalin, or benzodiazepines, including chlordiazepoxide, clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam; and/or in combination with an anti-psychotic, such as aripiprazole or risperidone; and/or in combination with a beta blocker, such as acebutolol, atenolol, betaxolol, bisoprolol, esmolol, nebivolol, metoprolol, cartelol, penbutolol, pindolol, carvedilol, labetalol, levobunolol, metipranolol, nadolol, propranolol, sotalol, or timolol.

In some embodiments, the activator is administered in combination with non-pharmaceutical therapy, such as brain stimulation, for example vagus nerve stimulation, repetitive transcranial magnetic stimulation, magnetic seizure therapy, and/or deep brain stimulation.

In some embodiments, the 22q deletion and/or duplication syndrome subject may have at least one co-morbid phenotype or condition such as oppositional defiant disorder (ODD), anxiety disorder, conduct disorder, Tourette's syndrome, autism, difficulty controlling anger, disruptive behavior, obsessive compulsive disorder (OCD), dermatillomania, a developmental disorder, or a movement disorder. In some embodiments, the subject does not have at least one of oppositional defiant disorder (ODD), anxiety disorder, conduct disorder, Tourette's syndrome, autism, difficulty controlling anger, disruptive behavior, obsessive compulsive disorder (OCD), dermatillomania, a developmental disorder, or a movement disorder, or in some embodiments, does not have any of those co-morbid conditions.

In some embodiments, wherein the 22q deletion and/or duplication subject has ADHD, the subject does not have at least one of ODD, conduct disorder, anxiety disorder, Tourette's syndrome, autism, difficulty controlling anger, disruptive behavior, obsessive compulsive disorder (OCD), dermatillomania, a developmental disorder, or a movement disorder. In some embodiments, the subject does not have any of ODD, conduct disorder, anxiety disorder, Tourette's syndrome, autism, difficulty controlling anger, disruptive behavior, obsessive compulsive disorder (OCD), dermatillomania, a developmental disorder, or a movement disorder. In some embodiments, the 22q deletion and/or duplication subject also has a mood disorder or a sleep disorder such as insomnia. In some such embodiments, the method treats the mood disorder or sleep disorder by, for example, reducing its symptoms. In some embodiments, the subject has ODD. In some such embodiments, the method treats ODD in the subject, for example by reducing symptoms of argumentativeness and defiance, vindictiveness, and/or anger and irritability. In some embodiments, the subject has co-morbid symptoms of anxiety and in some cases, the method reduces anxiety symptoms. In some embodiments, the subject has OCD and in some cases, the method reduces OCD symptoms. In some cases, the subject has co-morbid symptoms of dermatillomania, such as excessive skin picking, and the method reduces those symptoms. In some embodiments, the subject has one or more co-morbid developmental disorders, and in some cases, the method reduces the severity of symptoms related to the developmental disorders.

The 22q syndrome may be diagnosed in the subject by tests currently used to determine the presence of a 22q deletion or duplication. In some embodiments, a subject is diagnosed by a process comprising a genetic test to detect the presence or absence of a deletion or duplication at 22q11.2 and/or for the presence or absence of a genetic alteration in RANBP1 in a sample from the subject. In some embodiments, the method of treatment comprises obtaining results of a genetic test for 22q (such as for presence or absence of a deletion or duplication at 22q11.2 and/or for the presence or absence of a genetic alteration in RANBP1 in a sample from the subject) prior to initial administration of the activator. In some embodiments, the activator is administered in an amount or dosage regime shown to be effective to result in a clinical general impression—improvement (CGI-I) score of 1 or 2 after four weeks of treatment and/or an improvement of at least 25%, such as at least 30%, at least 35%, or at least 40%, in an ADHD rating scale score after four weeks of treatment in a majority of subjects of at least one clinical trial. In any of the above embodiments, the 22q syndrome may in some cases be deemed treated if neurobehavioral, neuropsychiatric and neurodevelopmental symptoms associated with 22q deletion and/or duplication syndrome are alleviated. Such symptoms include but are not limited to, improvements in memory, attention, cognition, anxiety, and stabilization or reversal of mood disorder, autism spectrum disorder, psychosis and hyperactivity. In any of the above embodiments, the 22q deletion and/or duplication syndrome may in some cases be deemed treated if at least one symptom of ADHD is improved in the subject. For example, in some embodiments, the methods may reduce behavioral symptoms such as inattentiveness, hyperactivity, and/or impulsiveness. In some embodiments, the methods also comprise assessing symptoms such as inattentiveness, hyperactivity, and/or impulsiveness as well as anger control and/or disruptive behaviors during or after administration, for example, to determine if one or more of those symptoms have been reduced in the subject. In some methods, such assessment may be performed based on an ADHD rating scale or based on a clinical global impression (CGI) scale, e.g. a CGI-severity or CGI-improvement scale.

For example, in some embodiments, the methods further comprise obtaining a clinical global impression of severity or improvement for the subject during or after administration. In some embodiments, the methods may improve clinical global improvement scores and/or ADHD rating scale scores in the subject. For example, in any of the above 22q deletion and/or duplication syndrome treatment methods, the subject may have one or more of the following changes in symptoms after at least one, two, three, or four weeks of treatment with the activator: (a) the subject has symptoms of anger control and the anger control symptoms are reduced; (b) the subject has symptoms of disruptive behavior and the disruptive behavior symptoms are reduced; (c) the subject's CGI-I is reduced by at least 1 or by at least 2; (d) the subject's CGI-I score after one, two, three, or four weeks of treatment is 1 or 2; (e) the subject's CGI-S score after one, two, three, or four weeks of treatment is 1; (f) the subject's ADHD Rating Scale score is reduced by at least 25%, such as at least 30%, at least 35%, or at least 40%; (g) the subject has symptoms of inattentiveness and the inattentiveness symptoms are reduced; (h) the subject has symptoms of hyperactivity and the hyperactivity symptoms are reduced; (i) the subject has symptoms of impulsiveness and the impulsiveness symptoms are reduced; (j) the subject has symptoms of ODD such as anger and irritability, argumentation and defiance, and/or vindictiveness and the ODD symptoms are reduced; (k) the subject has symptoms of conduct disorder and the conduct disorder symptoms are reduced; (l) the subject has symptoms of anxiety and the anxiety symptoms are reduced; (m) the subject has symptoms of Tourette's syndrome, and the Tourette's syndrome symptoms are reduced; (n) the subject has symptoms of autism, and the autism symptoms are reduced; and (o) the subject has symptoms of movement disorder and the movement disorder symptoms are reduced.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIGS. 1-1 to 1-4 show the mGluR network genes included in the Tier 1 gene set. These genes have 2 degrees of protein-protein interaction with mGluR genes (GRM1-8) based on the Cytoscape Human Interactome, which is software for integrating biomolecular interaction networks with high-throughput data (as described in Shannon P (2003) Genome Research 13:2498-2504). The Tier 1 gene set includes 76 genes. The exact location for each gene in Tier 1 is listed in both the Human Genome version 18 (hg18) and Human Genome version 19 (hg19). In addition, the exact gene location plus 500 kilobase (i.e., the range from 500 kilobase before and 500 kilobase after the gene of interest) is listed for hg19. The start single nucleotide polymorphism (StartSNP) (i.e., the SNP located 500 kilobases before the gene of interest) and the EndSNP (i.e., the SNP located 500 kilobases after the gene of interest) are also listed. Genes of the mGluRs themselves are noted as "GRM." The expanded regions (i.e., 500 kg up and down stream) frequently harbor regulatory elements and if impacted by a CNV, can have the same impact on the gene expression and function as a CNV residing in the gene sequence itself.

Figure 4:
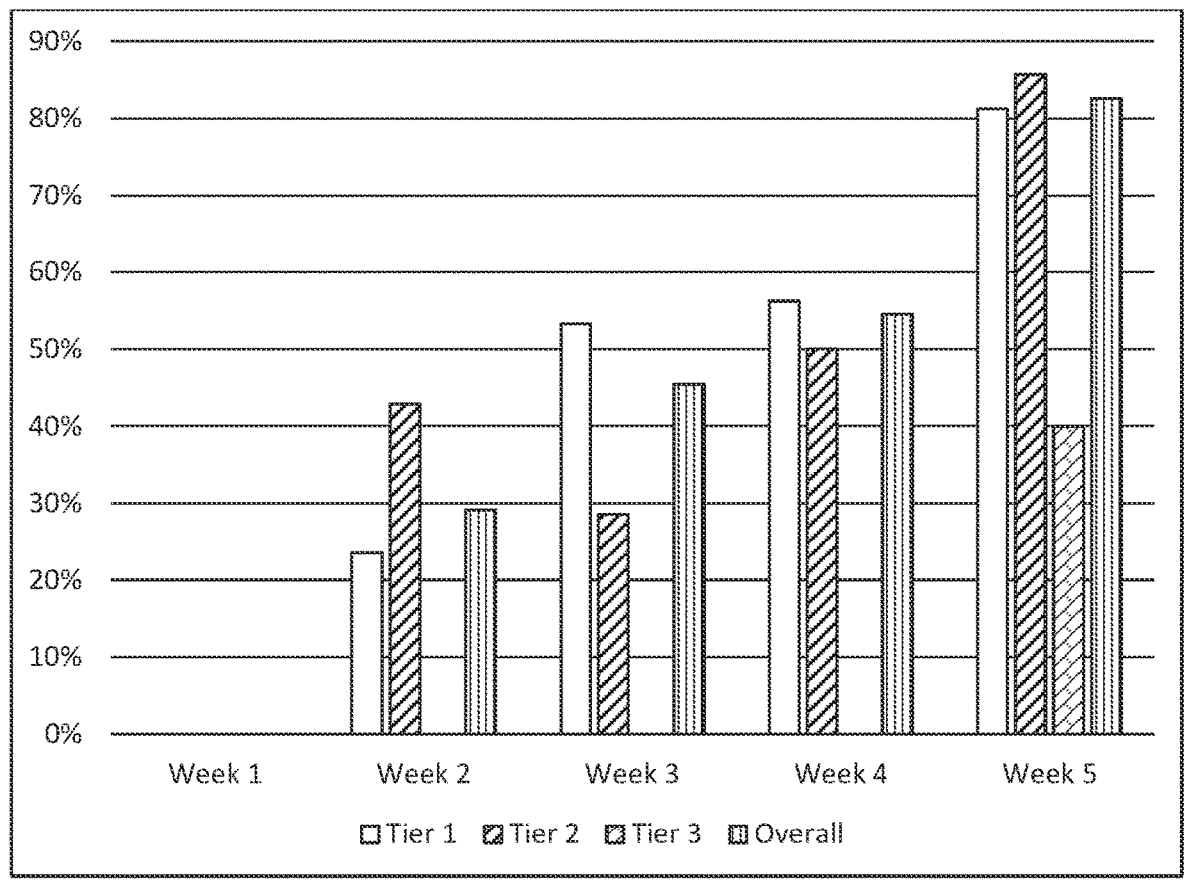

FIGS. 2-1 to 2-10 show the mGluR network genes included in the Tier 2 gene set. These genes have 2 degrees of protein-protein interaction with mGluR genes (GRM1-8) based on the Cytoscape Human Interactome but exclude genes from Tier 1. The Tier 2 gene set includes 197 genes. The exact location for each gene in Tier 2 is listed in both the Human Genome version 18 (hg18) and Human Genome version 19 (hg19). In addition, the exact gene location plus 500 kilobase (i.e., the range from 500 kilobase before and 500 kilobase after the gene of interest) is listed for hg19. The start single nucleotide polymorphism (StartSNP) (i.e., the SNP located 500 kilobases before the gene of interest) and the EndSNP (i.e., the SNP located 500 kilobases after the gene of interest) in hg19 are also listed.

FIGS. 3-1 to 3-29 show genes within the Tier 3 gene set. Genes with reciprocal gene querying with 2 degrees of protein-protein interaction with mGluR genes based on Cytoscape Human Interactome are included. Genes contained within Tiers 1 and 2 are excluded from Tier 3. The Tier 3 gene set includes 599 genes. The exact location for each gene in Tier 3 is listed in both the Human Genome version 18 (hg18) and Human Genome version 19 (hg19). In addition, the exact gene location plus 500 kilobase (i.e., the range from 500 kilobase before and 500 kilobase after the gene of interest) is listed for hg19. The StartSNP (i.e., the SNP located 500 kilobases before the gene of interest) and the EndSNP (i.e., the SNP located 500 kilobases after the gene of interest) in hg19 are also listed.

FIG. 4 shows the percentages of subjects the Phase Ib clinical trial described in Example 1 considered to be responders to NFC-1 based on having a clinical global impression—improvement (CGI-I) score of 1 or 2 (much improved or very much improved) at each week of the dose escalation phase of the clinical trial from week 1 (placebo baseline) to week 5, both based on the overall study population and based on genetic Tier (1, 2, or 3).

Figure 5A:
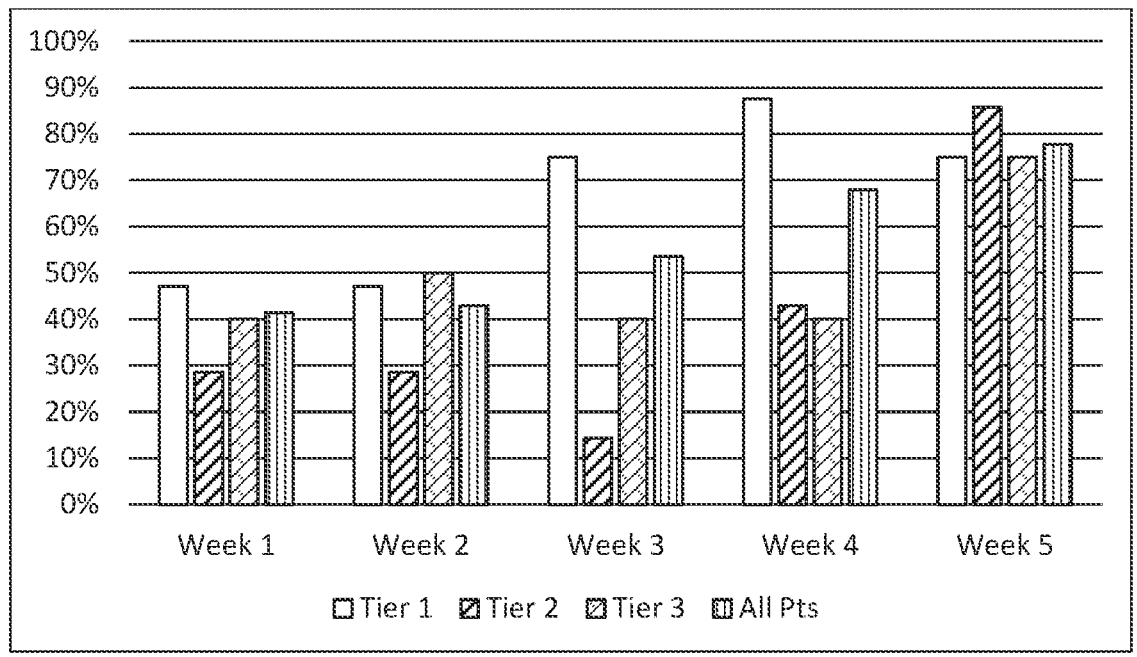
Figure 5B:
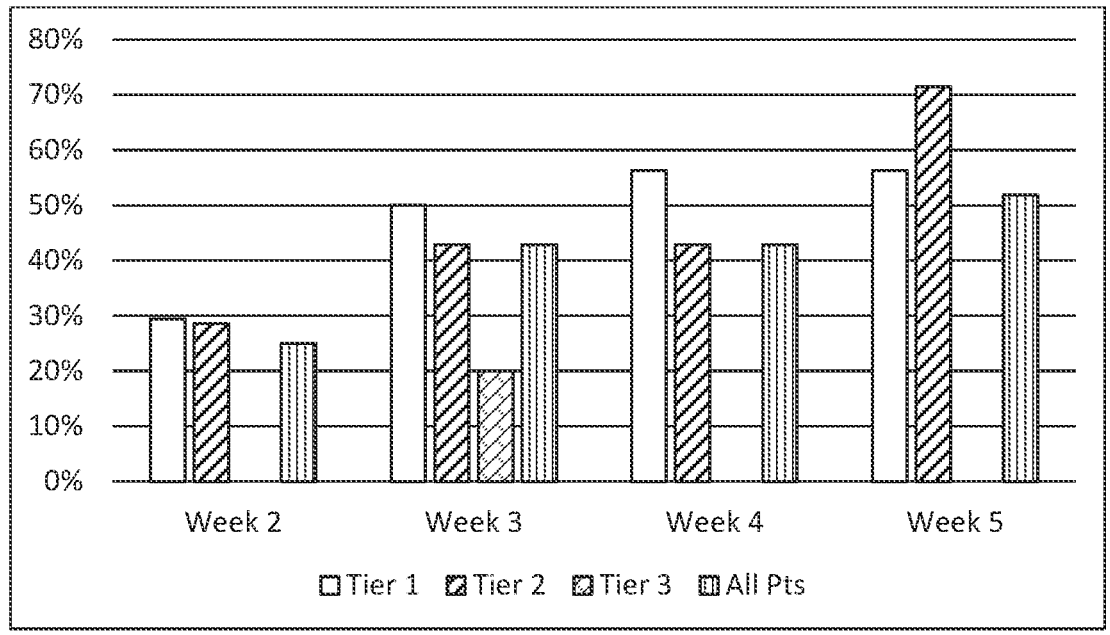

FIGS. 5a and 5b show the percent of clinical trial subjects showing improvement in Vanderbilt ADHD scores each week compared to either pre-study baseline (FIG. 5a) or placebo baseline (week 1) (FIG. 5b) both by genetic Tier and by the overall study population. An at least 25% decrease in Vanderbilt ADHD score is considered responsive and an improvement.

Figure 6A:
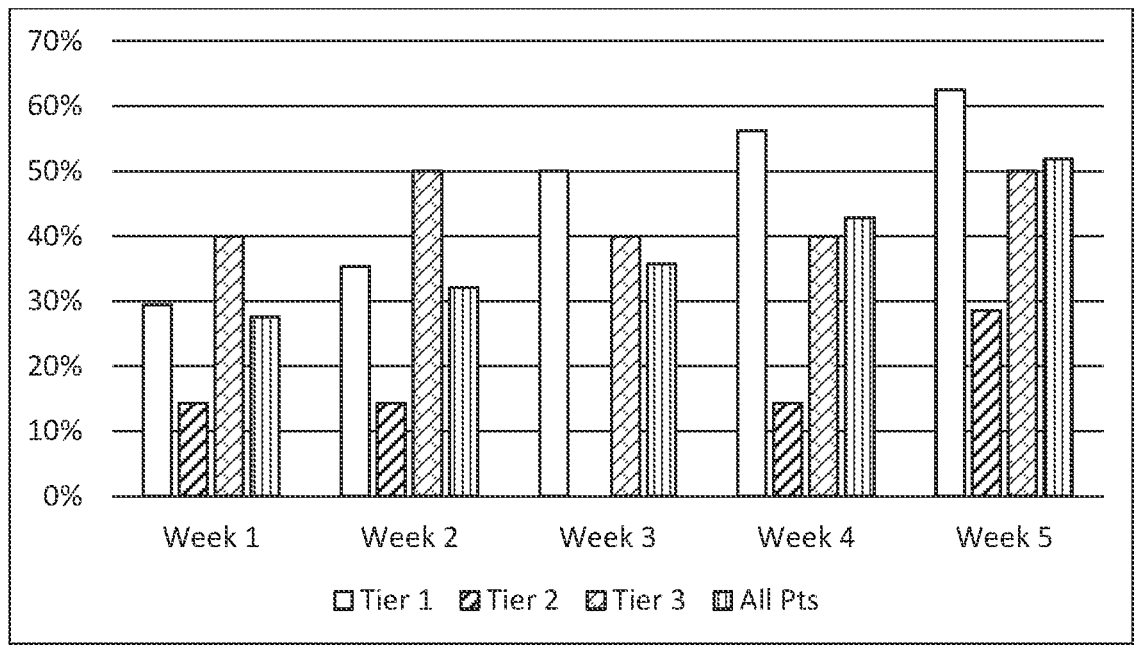
Figure 6B:
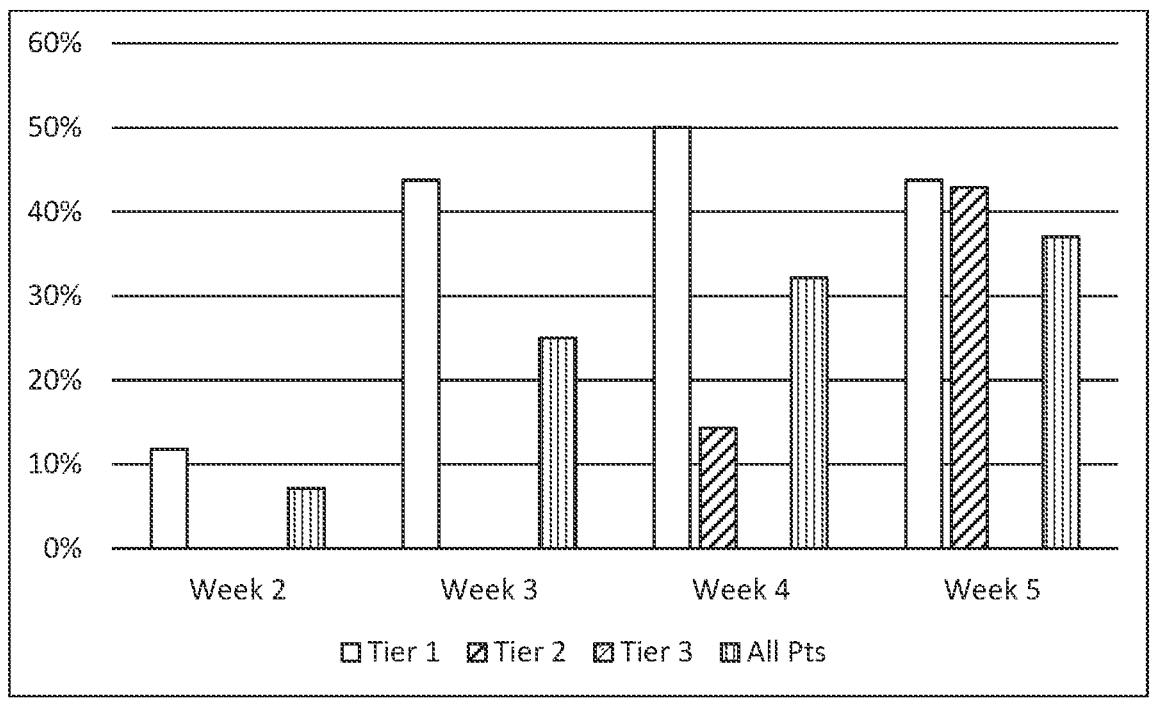

FIGS. 6a and 6b show the percent of clinical trial subjects showing robust improvement in Vanderbilt ADHD scores each week compared to either pre-study baseline (FIG. 6a) or placebo baseline (week 1) (FIG. 6b) both by genetic tier and by the overall study population. An at least 40% decrease in Vanderbilt ADHD score is considered a robust improvement.

Figure 7A:
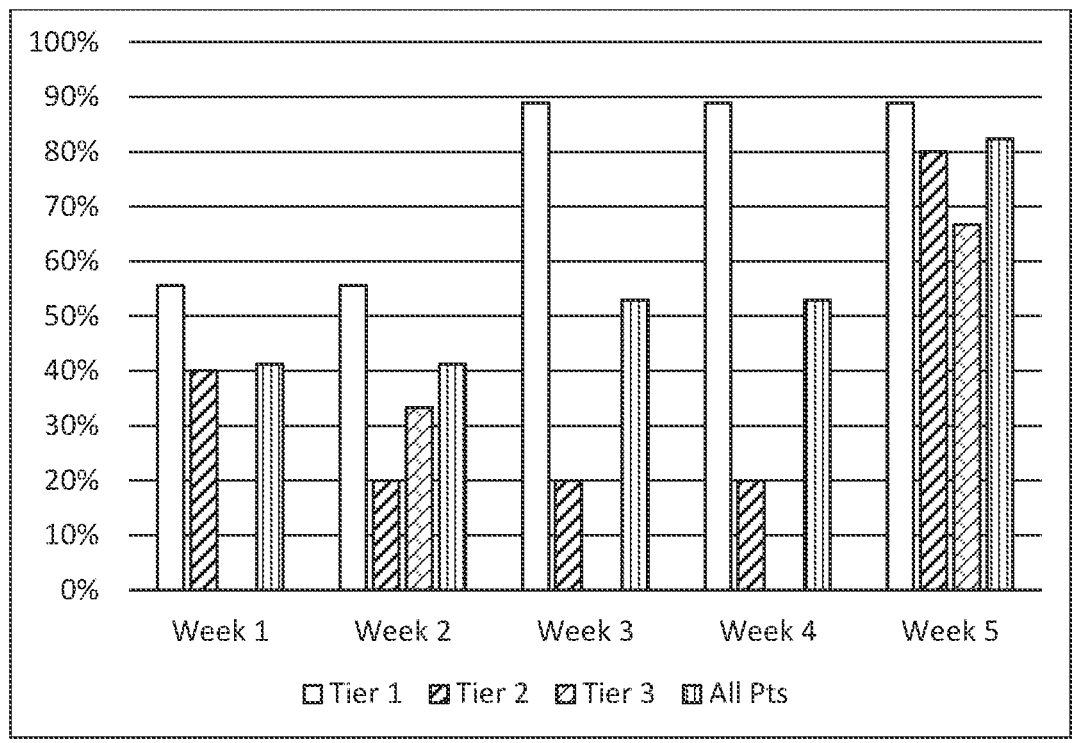
Figure 7B:
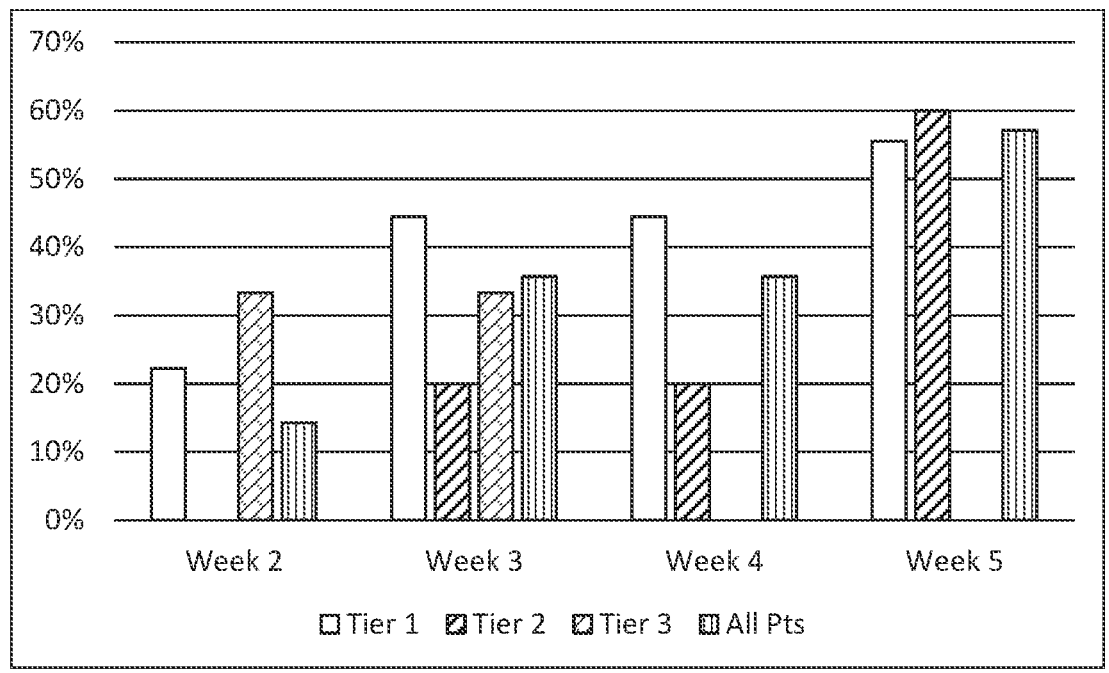

FIGS. 7a and 7b show the percent of clinical trial subjects who completed the full dose escalation to 400 mg twice daily NFC-1 at week 5 that showed improvement in Vanderbilt ADHD scores each week compared to either pre-study baseline (FIG. 7a) or placebo baseline (week 1) (FIG. 7b) both by genetic tier and by the overall study population. An at least 25% decrease in Vanderbilt ADHD score is considered an improvement.

Figure 8A:
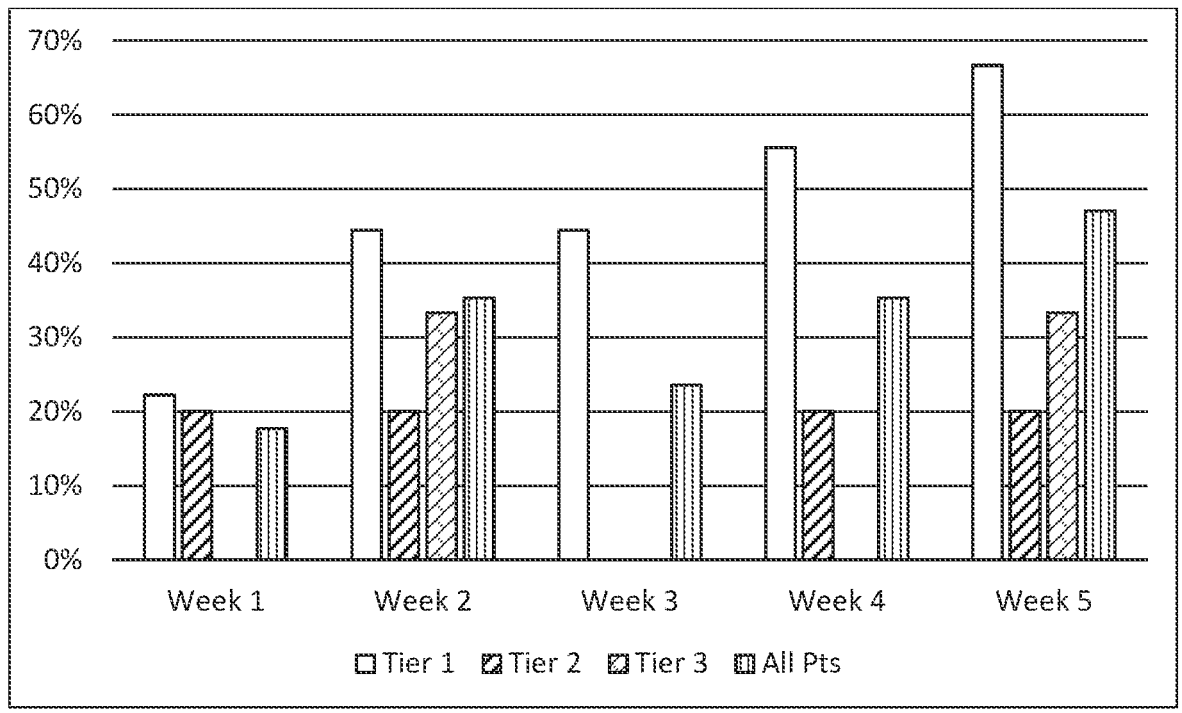
Figure 8B:
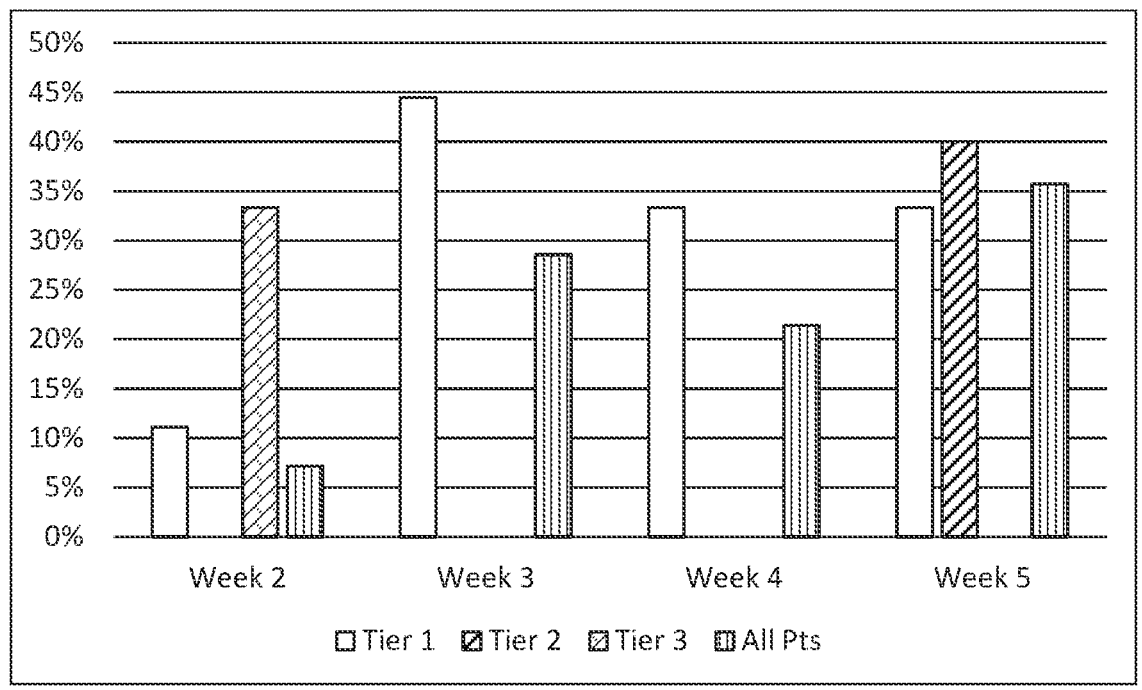

FIGS. 8a and 8b show the percent of clinical trial subjects who completed the full dose escalation to 400 mg twice daily NFC-1 at week 5 that showed robust improvement in Vanderbilt ADHD scores each week compared to either pre-study baseline (FIG. 8a) or placebo baseline (week 1) (FIG. 8b) both by genetic tier and by the overall study population. An at least 40% decrease in Vanderbilt ADHD score is considered a robust improvement.

Figure 9A:
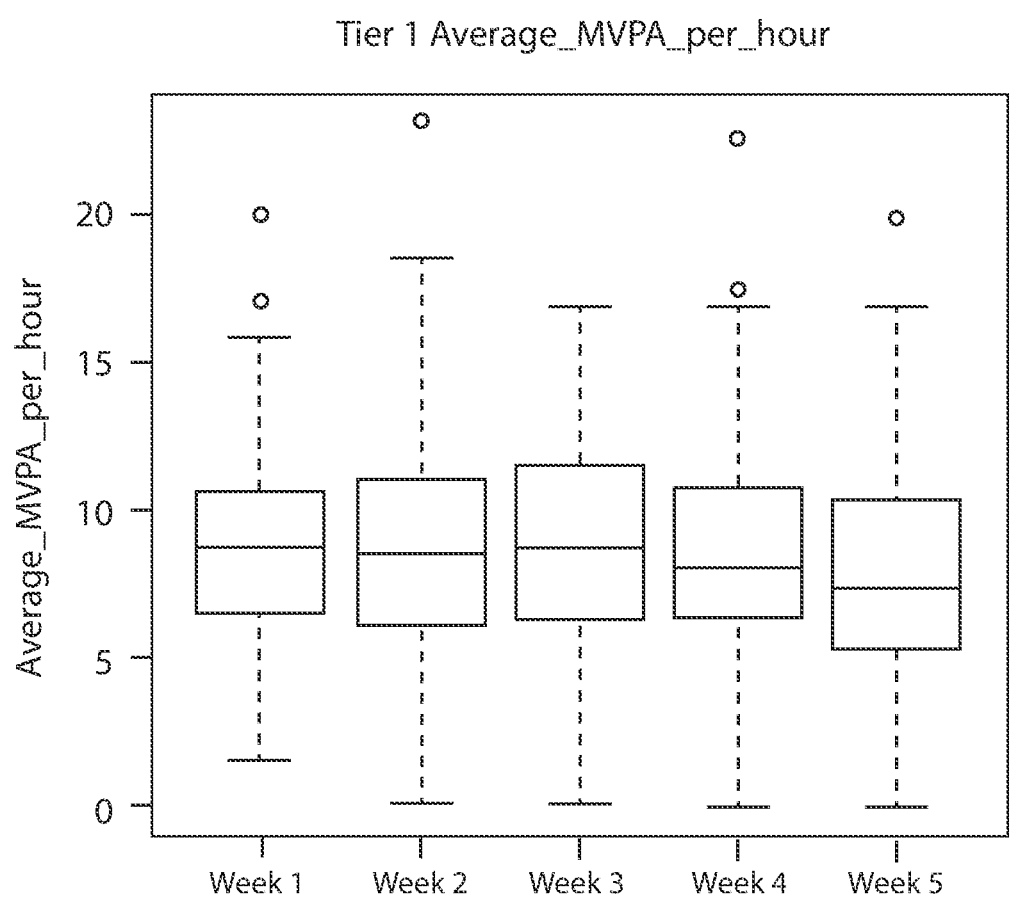
Figure 9B:
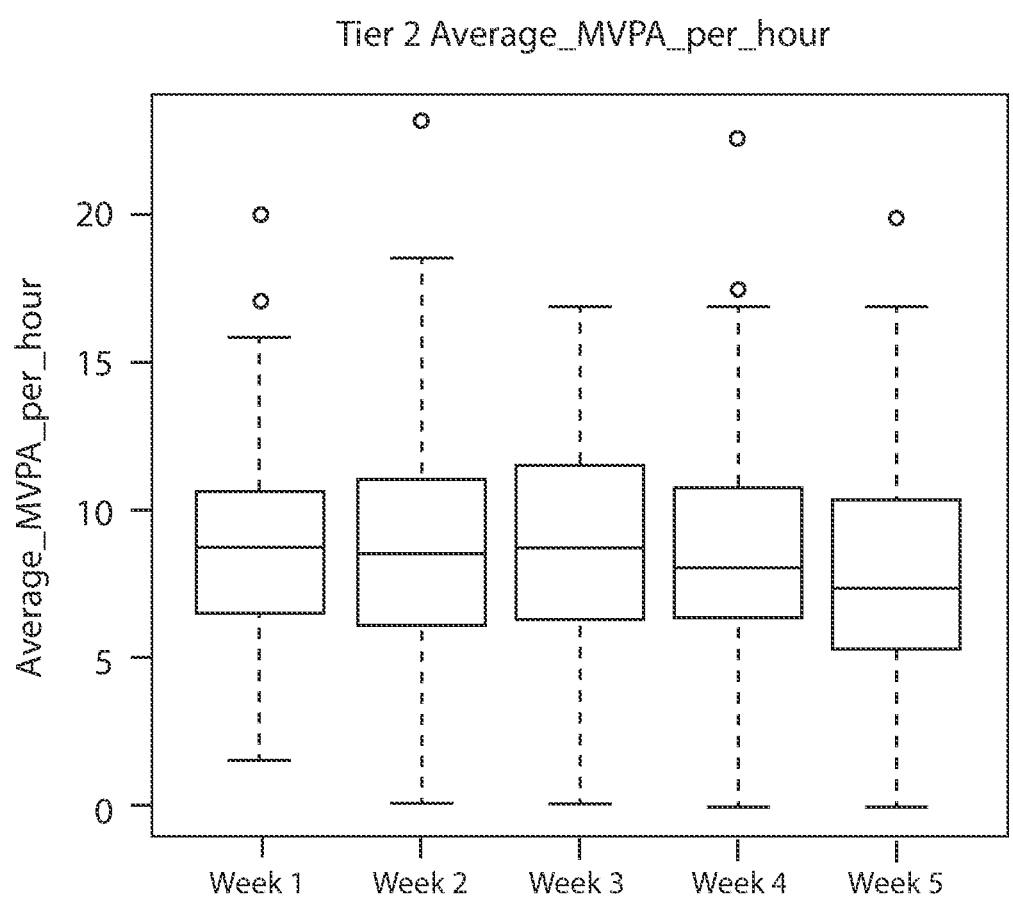
Figure 9C:
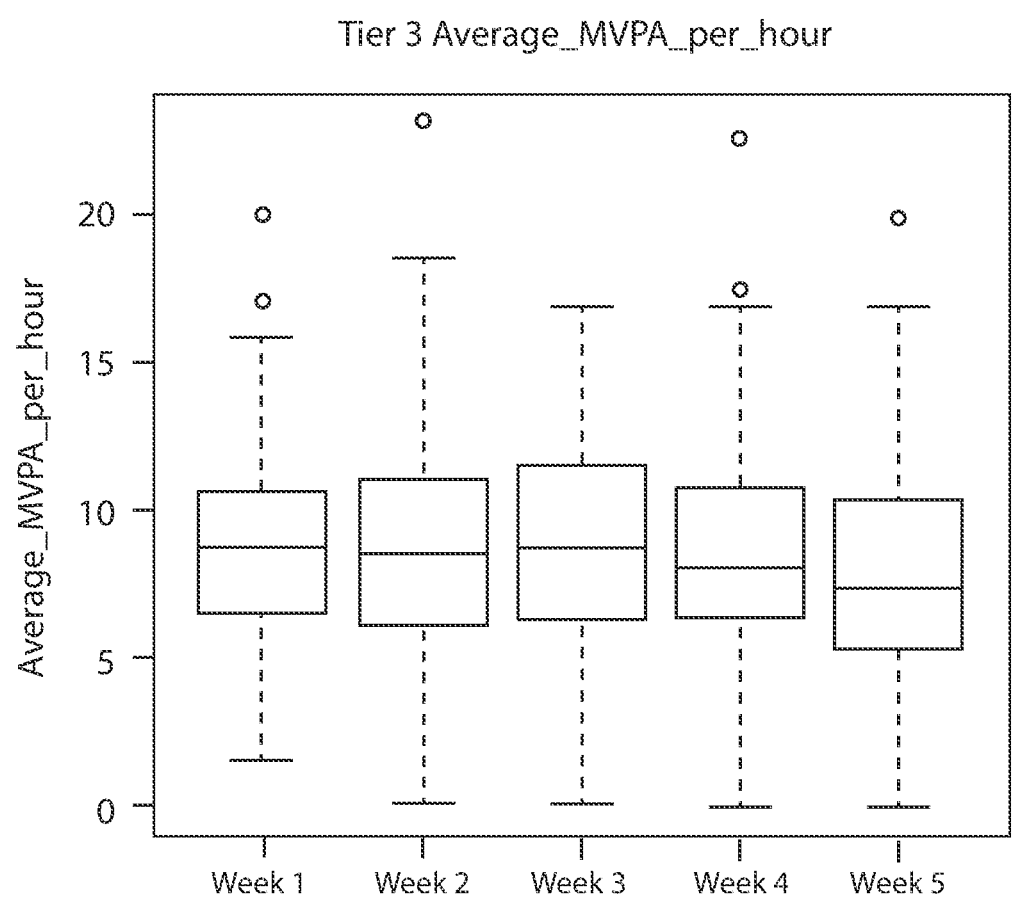

FIGS. 9a, 9b, and 9c show results from actigraphy tests in the subjects of the clinical trial by genetic tier group. The observed reduction in moderate to vigorous physical activity (MVPA) from week 1 (placebo) to week 5 for genetic Tier-1 (FIG. 9a); genetic Tier-2 (FIG. 9b); and genetic Tier-3 (FIG. 9c) was most prominent in 400 mg bid dose group.

Figure 10:
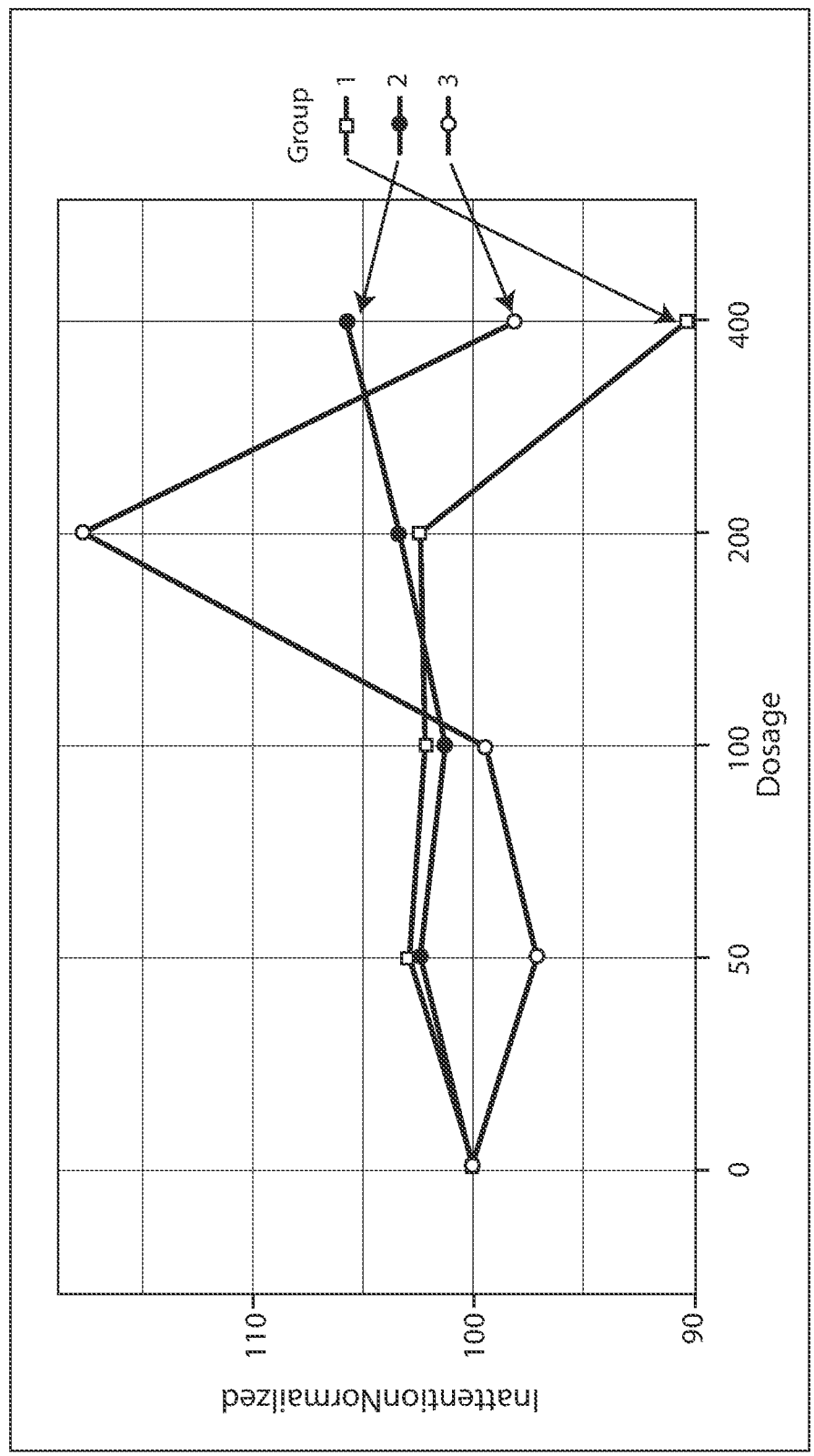

FIG. 10 shows that clinical trial subjects in the Tier-1 genetic group had significant improvement in the QUOTIENT® ADHD test's measure of inattention between week 1 (placebo) and week 5 (400 mg twice daily) as shown by reduction in inattention in the Tier-1 group (P<0.05) from a normalized inattention value of just over 100 to about 90 between weeks 4 (200 mg twice daily) and 5 (400 mg twice daily) of the dose escalation.

DESCRIPTION OF THE EMBODIMENTS

I. Definitions

In addition to definitions included in this sub-section, further definitions of terms are interspersed throughout the text.

In this invention, "a" or "an" means "at least one" or "one or more," etc., unless clearly indicated otherwise by context. The term "or" means "and/or" unless stated otherwise. In the case of a multiple-dependent claim, however, use of the term "or" refers back to more than one preceding claim in the alternative only.

An "mGluR" or metabotropic glutamate receptor refers to one of eight glutamate receptors expressed in neural tissue named mGluR1, mGluR2, mGluR3, mGluR4, mGluR5, mGluR6, mGluR7, and mGluR8. Their genes are abbreviated GRM1 to GRM8. The mGluR proteins are G-protein-coupled receptors. They are typically placed into three sub-groups, Group I receptors including mGluR1 and mGluR5 are classed as slow excitatory receptors. Group II includes mGluR2 and mGluR3. Group III includes mGluR4, mGluR6, mGluR7, and mGluR8. Groups II and III are classed as slow inhibitory receptors. The mGluRs are distinguished from the ionotropic GluRs or iGluRs, which are ion channel-associated glutamate receptors and are classed as fast excitatory receptors.

An "mGluR network gene," for purposes of this invention, comprises not only the mGluR genes GRM1, GRM2, GRM3, GRM4, GRM5, GRM6, GRM7, and GRM8, but also each of the other genes listed herein in FIGS. 1-3 as well as the regions of DNA that regulate the genes listed in FIGS. 1-3. In addition, "mGluR network proteins" are the proteins encoded by the mGluR network genes.

The mGluR network genes are grouped into three subsets: Tier 1, Tier 2, and Tier 3. (See FIGS. 1-3.) Tier 1 mGluR network genes, shown in FIG. 1, comprise 76 genes, including some GRM genes themselves as well as a number of other genes. The Tier 2 mGluR network genes, shown in FIG. 2, comprise 197 genes, and exclude the Tier 1 genes.

Tiers 1 and 2 together are included in the "primary mGluR network." The "primary network" of mGluR genes also includes the genes 4-Sep, LOC642393, and LOC653098, for a total of 276 genes. There are presently technical difficulties in assessing the 4-Sep, LOC642393, and LOC653098 genes. Thus, they are not included in Tiers 1 and 2, although they are included in the primary network of genes of the present invention. The genes of Tier 1 and Tier 2 differ in that alterations in Tier 1 genes had been documented in previous genotyping studies of subjects suffering from mental disorders.

Tier 3 mGluR network genes, shown in FIG. 3, comprise 599 genes that are in the distal part of the mGluR network based on the merged human interactome provided by the Cytoscape Software (Shannon P et al. (2003) Genome Research 13:2498-2504), and exclude the Tier 1 and Tier 2 genes. The Tier 3 genes are thus part of the "distal mGluR network." In addition to the Tier 3 genes, the genes LOC285147, LOC147004, and LOC93444 are included in the "distal mGluR network," although they were not assessed in the present study and are not included in Tier 3 due to technical difficulties.

A "genetic alteration" as used herein means any alteration in the DNA of a gene, or in the DNA regulating a gene, that, for example, may result in a gene product that is functionally changed as compared to a gene product produced from a non-altered DNA. A function change may be differing expression levels (up-regulation or down-regulation) or loss or change in one or more biological activities, for example. A genetic alteration includes without limitation, copy number variations (CNVs), single nucleotide variations (SNVs) (also called single nucleotide polymorphisms (SNPs) herein), frame shift mutations, or any other base pair substitutions, insertions, and deletions.

A "copy number variation" or "CNV" is a duplication or deletion of a DNA segment encompassing a gene, genes, segment of a gene, or DNA region regulating a gene, as compared to a reference genome. In some embodiments, a CNV is determined based on variation from a normal diploid state. In some embodiments, a CNV represents a copy number change involving a DNA fragment that is 1 kilobase (kb) or larger. CNVs described herein do not include those variants that arise from the insertion/deletion of transposable elements (e.g., 6-kb KpnI repeats). The term CNV therefore encompasses terms such as large-scale copy number variants (LCVs; Iafrate et al. 2004), copy number polymorphisms (CNPs; Sebat et al. 2004), and intermediate-sized variants (ISVs; Tuzun et al. 2005), but not retrotransposon insertions.

A "CNV deletion" or "deletion CNV" or similar terms refer to a CNV in which a gene or gene segment is deleted. A "CNV duplication" or "duplication CNV" or similar terms refer to a CNV in which a gene or gene segment is present in at least two, and possibly more than two, copies in comparison with the single copy found in a normal reference genome.

A "sample" refers to a sample from a subject that may be tested, for example, for presence of a CNV in one or more mGluR network proteins, as described herein. The sample may comprise cells, and it may comprise body fluids, such as blood, serum, plasma, cerebral spinal fluid, urine, saliva, tears, pleural fluid, and the like.

As used herein "22q syndrome" and "22q11.2 syndrome" are used interchangeably.

The terms "pediatric subject" or "pediatric patient" are used interchangeably to refer to a human less than 18 years of age. An "adult patient" or "adult subject" refers to a human 18 years of age or older. An "adolescent patient" or "adolescent subject" is typically about 12 to 18, such as 12 to 17 or 13 to 18, years old.

II. Attention Deficit Hyperactivity Disorder (ADHD)

The term "attention deficit hyperactivity disorder" or ADHD refers to a heterogeneous disorder that may be characterized at least in part by inattentiveness, hyperactivity, and impulsiveness. Symptoms of ADHD include difficulty staying focused and paying attention, difficulty controlling behavior, and hyperactivity. According to the Diagnostic and Statistical Manual of Mental Disorders, 5th Ed., (DSM-5), a physician may diagnose ADHD when a subject shows a persistent pattern of inattentiveness or hyperactivity-impulsiveness that interferes with the subject's functioning or development. ADHD may occur in at least 5% of the population and may be diagnosed in both adult and pediatric subjects.

There are three classes of ADHD: predominantly hyperactive-impulsive, predominantly inattentive, and combined hyperactive-impulsive and inattentive. Predominantly hyperactive-impulsive patients have more pronounced hyperactivity-impulsivity than inattention. Predominantly inattentive patients lack attention, but they have fewer symptoms of hyperactivity-impulsivity; these patients may be able to sit quietly in classroom setting but are not paying attention to the task that they are supposed to be performing. Combined hyperactive-impulsive and inattentive patients have significant symptoms of both inattention and hyperactivity-impulsivity. Combined ADHD is the most common type in children. Each of the methods described herein encompass treatment of all classes of ADHD.

ADHD is a heterogeneous condition and may result from a combination of factors, such as genes, environmental factors, and/or brain injuries. In addition, ADHD patients are significantly more likely than normal individuals to have a genetic alteration such as a CNV in at least one mGluR network gene. (See WO 2012/027491 and US 2013/0203814; Elia et al., Nature Genetics, 44(1): 78-84 (2012).)

Currently approved therapeutics for ADHD include stimulant drugs, such as methylphenidate and amphetamines, as well as non-stimulant drugs, such as atomoxetine. Antidepressants may also be given in some cases, such as serotonin selective uptake inhibitors, e.g. fluoxetine, sertraline, and citalopram, as well as clonidine and guanfacine. These medications, however, may have a number of possible side effects and some also have short half-lives of activity.

Some subjects with ADHD may have one or more co-morbid disorders such as oppositional defiant disorder (ODD), anxiety disorder, a mood disorder, a phobia, obsessive compulsive disorder (OCD), depression, conduct disorder, Tourette's syndrome, autism, or a movement disorder. In other cases, an ADHD subject does not have any of ODD, anxiety disorder, a mood disorder, a phobia, obsessive compulsive disorder (OCD), depression, conduct disorder, Tourette's syndrome, autism, or a movement disorder. Some subjects with ADHD may also show mood disorders or sleep disorders such as insomnia.

About 40% of pediatric ADHD patients, for example, also have ODD, and some ADHD medications are believed to improve ODD symptoms as part of treating ADHD. According to the DSM-5, a subject may be diagnosed with ODD if the subject shows at least four symptoms indicative of an angry and irritable mood, argumentative and defiant behavior, or vindictiveness that occur with at least one non-sibling individual, that cause significant problems at work, school, or at home, and that persist for at least six months. Symptoms indicative of an angry and irritable mood include: often loses temper, is often touchy or easily annoyed by others, is often angry and resentful. Symptoms indicative of argumentative and defiant behavior include: often argues with adults or people in authority, often actively defies or refuses to comply with adults' requests or rules, often deliberately annoys people, and often blames others for his/her own mistakes or misbehavior. Symptoms indicative of vindictiveness include: is often spiteful or vindictive, and has shown spiteful or vindictive behavior at least twice within the past six months. The symptoms must occur on their own and not as part of the course of another mental health problem such as substance abuse, depression, or bi-polar disorder. Individuals 5 years and older may be diagnosed with ODD if the symptoms occur at least once per week for at least six months. Accordingly, a subject with "ODD" is defined herein as one who has been diagnosed as having ODD based on the above DSM-5 criteria.

Subjects with ADHD may also show a variety of additional behavioral phenotypes such as difficulty controlling anger and disruptive behaviors whether or not the subjects have been diagnosed with a co-morbid disorder.

Other co-morbid disorders that an ADHD subject may suffer from include obsessive compulsive disorder (OCD), a developmental disorder, or dermatillomania. "Developmental disorders" herein include, for example, those classified under the International Classification of Diseases 9$^{th}$ Ed. (World Health Organization) under codes 299.80, 299.90, 315.2, 315.39, 315.4, 315.5, 315.8, and 315.9, and may affect behaviors such as learning, coordination, and speech. "Dermatillomania" is also called skin picking disorder or excoriation, and is a disorder involving excessive picking at one's own skin to the extent of causing damage, and includes picking at normal skin as well as at real or imagined skin defects such as moles, freckles, or acne.

III. 22q Syndromes

The terms "22q syndrome" or "22q11 syndrome" or "22q11.2 syndrome" are used interchangeably herein to refer to subjects whose genomes have a CNV in the q11.2 region of chromosome 22 that includes the RANBP1 mGluR network gene locus. RANBP1 encodes a protein that interacts with mGluR3. A subject with "22q deletion syndrome" or "22qDS" or "22q11.2DS" has a deletion in that region of the chromosome while a subject with "22q duplication syndrome" or "22qDupS" or "22q11.2DupS" has a duplication in that region.

Deletion of a small piece of chromosome 22 at q11.2 that includes the RANBP1 mGluR network gene locus is called "22q deletion syndrome" or "22q11.2DS." A 22q deletion frequently involves loss of approximately 30 to 40 genes including RANBP1 and may be characterized by heart defects, cleft palate, and distinctive facial features, as well as a low intellectual level. About 37% of children with 22q11.2DS are also diagnosed with ADHD. Children with 22q11.2DS also have high rates of autism spectrum (ASD) and anxiety disorder, and a significant percentage may develop psychoses such as schizophrenia later in life. 22q11.2DS occurs in about 1 out of every 2000-4000 people, although this may be an under-estimate as mild cases may not always be diagnosed. Before the genetic basis of 22q11.2DS was understood, different groupings of symptoms of 22q11.2DS were previously called DiGeorge syndrome, velocardiofacial syndrome, and conotruncal anomaly face syndrome.

Duplication at position q11.2 on chromosome 22, including the RANBP1 locus, is called "22q duplication syndrome," "22q11.2 duplication syndrome" or "22q11.2DupS," and may be characterized by intellectual/learning disability, delayed psychomotor development, growth retardation, and muscular hypotonia. The piece of chromosome 22 that is duplicated in 22q.11.2DupS if often the same one that is frequently deleted in 22q11.2DS, involving 30-40 genes. The incidence of 22q11.2DupS in patients referred for genomic microarray analysis to investigate developmental delays or intellectual disability is about 1 in 300-700.

Available diagnostic tests for 22q11.2DS include targeted variant analysis (which looks for variants in a panel of targets), fluorescence in situ hybridization (FISH), and sequence coding of the entire coding region. Available diagnostic tests for 22q11.2DupS include chromosomal microarray and FISH methodology

IV. The mGluR Network Genes

In some embodiments herein, ADHD patients may be evaluated prior to treatment for a genetic alteration in one or more of the Tier 1, 2, and/or 3 mGluR network genes, such as single gene or a panel of such genes. In some embodiments, the genetic alteration is a copy number variation (CNV), resulting from a duplication or other multiplication of one or both copies of the gene or a deletion of one or both copies of the gene. A CNV deletion or duplication can alter the expression of a resulting gene product contained within the CNV because of the change in copy number of this gene, and may therefore contribute to a disease phenotype. However, a CNV deletion or duplication may also have no effect on relative expression of gene products in any tissue (see Henrichsen C N et al. (2009) Human Molecular Genetics, 2009, Vol. 18(1):R1-R8). A CNV deletion or duplication may also affect the expression of genes located in the vicinity of the CNV, such that expression of genes outside of the actual CNV may also be affected. A CNV can also influence gene expression through perturbation of transcript structure; for example, a duplication CNV may lead to an increase in copy number but may actually lead to a decrease in gene product due to interference with normal transcription.

In some embodiments, ADHD patients are treated who have at least one genetic alteration, such as at least one CNV in an mGluR network gene, such as in a Tier1, Tier2, and/or Tier3 gene as shown in FIGS. 1-3. In some embodiments, the patient has a genetic alteration, such as a CNV, such as a deletion or duplication that includes the gene RANBP1, a gene that may be deleted or duplicated in 22q syndromes.

In some embodiments, gene sets or panels of mGluR network genes are used for analyzing samples from patients with suspected ADHD or 22q deletion and/or duplication syndromes. In some embodiments, the presence of genetic alterations such as CNV duplications or deletions within these gene sets or panels is determined. In some embodiments, genetic alterations such as CNVs in the Tier 1 genes shown in FIG. 1 are determined. In some embodiments a panel of at least 1, 2, 3, 4, 5, 6, 7, 8, 9, 10, 20, 30, 40, 50, 60, 70, or all of the Tier 1 genes is evaluated for the presence of genetic alterations such as CNVs. Within those embodiments, in some embodiments the panel includes specific genes such as RANBP1 or GRM1-8. Within any such panel of genes, any individual, specific Tier 1 genes may also be excluded from the panel. For instance, in some embodiments, one or more of the GRM1-8 genes are not included in the panel.

In some embodiments, the Tier 2 genes as shown in FIG. 2 are analyzed for the presence of genetic alterations such as CNVs, optionally in addition to evaluation of the above Tier 1 evaluations or in addition to evaluations of subsets of the Tier 1 genes as described above. In some embodiments, at least 50 Tier 2 genes are evaluated, while in some embodiments, at least 10, 20, 30, 50, 100, 150, or all of the Tier 2 genes are evaluated. Individual, specific Tier 2 genes may be excluded from the gene set for evaluation in some embodiments.

In some embodiments, the 599 Tier 3 genes shown in FIG. 3 are evaluated for genetic alterations such as CNVs, optionally in addition to evaluation of the above Tier 1 and/or Tier 2 evaluations or in addition to evaluations of subsets of the Tier 1 and/or Tier 2 genes as described above. Tier 3 genes are considered a wide range of potential interactors with the mGluR network, and genes contained within Tier 3 are not contained in Tier 1 and Tier 2. In some embodiments, at least 10, 20, 50, 100, 200, 300, 400, 500 or all of the Tier 3 genes are included in a panel to evaluate genetic alterations.

V, Evaluation of Genetic Alterations in mGluR Network Genes

Any biological sample may be used to determine the presence or absence of mGluR network gene alterations, including, but not limited to, blood, urine, serum, gastric lavage, CNS fluid, any type of cell (such as brain cells, white blood cells, mononuclear cells) or body tissue. Any biological source material whereby DNA can be extracted may be used to determine the presence or absence of mGluR network gene alterations. Samples may be freshly collected, or samples may have been previously collected for any use/purpose and stored until the time of testing for genetic alterations. DNA that was previously purified for a different purpose may also be used.

Various methods for determining genetic alterations are known, including the following:

A. Single Nucleotide Variation (SNV)/Single Nucleotide Polymorphism (SNP) Genotyping Determining whether a patient has a genetic alteration, such as a CNV, in a mGluR network gene may be done by SNV/SNP Genotyping, using a SNV/SNP genotyping array such as those commercially available from Illumina or Affymetrix. A "single nucleotide variation (SNV)," also interchangeably referred to as a "single nucleotide polymorphism (SNP)" herein, refers to a change in which a single base in the DNA differs from the usual base at that position. Millions of SNVs have been cataloged in the human genome. Some SNVs are normal variations in the genome, while others are associated with disease. While specific SNVs may be associated with disease states or susceptibility, high-density SNV genotyping can also be undertaken, whereby sequencing information on SNVs is used to determine the unique genetic makeup of an individual.

In SNV genotyping, SNVs can be determined by hybridizing complementary DNA probes to the SNV site. A wide range of platforms can be used with SNV genotyping tools to accommodate varying sample throughputs, multiplexing capabilities, and chemistries. In high-density SNV arrays, hundreds of thousands of probes are arrayed on a small chip, such that many SNVs can be interrogated simultaneously when target DNA is processed on the chip. By determining the amount of hybridization of target DNA in a sample to a probe (or redundant probes) on the array, specific SNV alleles can be determined. Use of arrays for SNV genotyping allows the large-scale interrogation of SNVs.

When analyzing CNVs, after SNVs have been analyzed, a computer program can be used to manipulate the SNV data to arrive at CNV data. PennCNV or a similar program, can then be used to detect signal patterns across the genome and identify consecutive genetic markers with copy number changes. (See Wang K, et al. (June 2008) Cold Spring Harb Protoc). PennCNV allows for kilobase-resolution detection of CNVs. (See Wang K, et al. (November 2007) Genome Res. 17(11):1665-74).

In CNV analysis, the SNV genotyping data is compared with the behavior of normal diploid DNA. The software uses SNV genotyping data to determine the signal intensity data and SNV allelic ratio distribution and to then use these data to determine when there is deviation from the normal diploid condition of DNA that indicates a CNV. This is done in part by using the log R Ratio (LRR), which is a normalized measure of the total signal intensity for the two alleles of the SNV (Wang 2008). If the software detects regions of contiguous SNVs with intensity (LRR) trending below 0, this indicates a CNV deletion. If the software instead detects regions of contiguous SNVs with intensity (LRR) trending above 0, this indicates a CNV duplication. If no change in LRR is observed compared to the behavior of diploid DNA, the sequence is in the normal diploid state with no CNV present. The software also uses B allele frequency (BAF), a normalized measure of the allelic intensity ratio of two alleles that changes when alleles are lost or gained as with a CNV deletion or duplication. For example, a CNV deletion is indicated by both a decrease in LRR values and a lack of heterozygotes in BAF values. In contrast, a CNV duplication is indicated by both an increase in LRR values and a splitting of the heterozygous genotype BAF clusters into two distinct clusters. The software automates the calculation of LRR and BAF to detect CNV deletions and duplications for whole-genome SNV data. The simultaneous analysis of intensity and genotype data accurately defines the normal diploid state and determines CNVs.

Array platforms such as those from Illumina, Affymetrix, and Agilent may be used in SNV Genotyping. Custom arrays may also be designed and used based on the data described herein.

B. Comparative Genomic Hybridization

Comparative genomic hybridization (CGH) is another method that may be used to evaluate genetic alterations such as CNVs. CGH is a molecular cytogenetic method for analyzing genetic alterations such as CNVs in comparison to a reference sample using competitive fluorescence in situ hybridization (FISH). DNA is isolated from a patient and a reference source and independently labeled with fluorescent molecules (i.e., fluorophores) after denaturation of the DNA. Hybridization of the fluorophores to the resultant samples are compared along the length of each chromosome to identify chromosomal differences between the two sources. A mismatch of colors indicates a gain or loss of material in the test sample in a specific region, while a match of the colors indicates no difference in genetic alterations such as copy number between the test and reference samples at a particular region. In certain embodiments, the fluorophores are not naturally occurring.

C. Whole Genome Sequencing, Whole Exome Sequencing, and Targeted Sequencing

Whole genome sequencing, whole exome sequencing, or targeted sequencing may also be used to analyze genetic alterations such as CNVs. Whole genome sequencing (also known as full genome sequencing, complete genome sequencing, or entire genome sequencing) involves sequencing of the full genome of a species, including genes that do or do not code for proteins. Whole exome sequencing, in contrast, is sequencing of only the protein-coding genes in the genome (approximately 1% of the genome). Targeted sequencing involves sequencing of only selected parts of the genome.

A wide range of techniques would be known to those skilled in the art to perform whole genome, whole exome, or targeted sequencing with DNA purified from a subject. Similar techniques could be used for different types of sequencing. Techniques used for whole genome sequencing include nanopore technology, fluorophore technology, DNA nanoball technology, and pyrosequencing (i.e., sequencing by synthesis). In particular, next-generation sequencing (NGS) involves sequencing of millions of small fragments of DNA in parallel followed by use of bioinformatics analyses to piece together sequencing data from the fragments.

As whole exome sequencing does not need to sequence as large an amount of DNA as whole genome sequencing, a wider range of techniques are may be used. Methods for whole exome sequencing include polymerase chain reaction methods, NGS methods, molecular inversion probes, hybrid capture using microarrays, in-solution capture, and classical Sanger sequencing. Targeted sequencing allows for providing sequence data for specific genes rather than whole genomes and can use any of the techniques used for other types of sequencing, including specialized microarrays containing materials for sequencing genes of interest.

D. Other Methods for Determining Genetic Alterations

Proprietary methodologies, such as those from BioNano or OpGen, using genome mapping technology can also be used to evaluate genetic alterations such as CNVs.

Standard molecular biology methodologies such as quantitative polymerase chain reaction (PCR), droplet PCR, and TaqMan probes (i.e., hydrolysis probes designed to increase the specificity of quantitative PCR) can be used to assess genetic alterations such as CNVs. Fluorescent in situ hybridization (FISH) probes may also be used to evaluate genetic alterations such as CNVs. The analysis of genetic alterations such as CNVs present in patients is not limited by the precise methods whereby the genetic alterations such as CNVs are determined VI. Treatment of ADHD and 22q Syndromes with Nonselective mGluR Activators In some embodiments, a subject with ADHD is treated with a nonselective mGluR activator. In other embodiments, a subject with 22q deletion and/or duplication syndrome is treated with a nonselective mGluR activator. In still other embodiments, a subject with ADHD and a 22q deletion and/or duplication syndrome is treated with a nonselective mGluR activator. The terms "subject" and "patient" are used interchangeably to refer to a human. The terms "pediatric subject" or "pediatric patient" are used interchangeably to refer to a human less than 18 years of age. In some embodiments, the subject may be between 6 and 17 years old, such as between 12 and 17 years old or between 6 and 12 years old. The terms "adult subject" or "adult patient" refer to a human of at least 18 years of age. An "adolescent" subject, for example, may be between 12 and 18, such as 12-17, 13-17, or 13-18 years old.

The term "treatment," as used herein, covers any administration or application of a therapeutic for disease in a subject, and includes inhibiting the disease, arresting its development, relieving one or more symptoms of the disease, or preventing reoccurrence of one or more symptoms of the disease. For example, treatment of 22q deletion and/or duplication syndrome subjects may comprise alleviating neurobehavioral, neuropsychiatric and neurodevelopmental symptoms associated with 22q deletion and/or duplication syndrome. Such symptoms include but are not limited to, improvements in memory, attention, cognition, anxiety, and stabilization or reversal of mood disorder, autism spectrum disorder, psychosis and hyperactivity. Treating an ADHD or 22q deletion and/or duplication subject may comprise alleviating symptoms of inattentiveness, hyperactivity, and/or impulsiveness associated with ADHD, as well as improving associated phenotypes such as mood disorders and sleep disorders, anger control, and disruptive behaviors.

The mGluR proteins are typically placed into three subgroups, group I receptors including mGluR1 and mGluR5 are classed as slow excitatory receptors. Group II includes mGluR2 and mGluR3. Group III includes mGluR4, mGluR6, mGluR7, and mGluR8. Groups II and III are classed as slow inhibitory receptors. The mGluRs are distinguished from the ionotropic GluRs or iGluRs, which are ion channel-associated glutamate receptors and are classed as fast excitatory receptors.

A "nonselective activator of mGluRs" refers to a molecule that activates mGluRs from more than one of the group I, II, and III categories. Thus, a nonselective activator of mGluRs may provide for a general stimulation of the mGluR networks. This is in contrast to specific mGluR activators that may only significantly activate a single mGluR, such as mGluR5, for example. Nonselective mGluR activators include, for example, nonselective mGluR agonists.

In some embodiments the nonselective mGluR activator is "fasoracetam." Fasoracetam is a nootropic (i.e., cognitive-enhancing) drug that can stimulate both group I and group II/III mGluRs in in vitro studies. (See Hirouchi M, et al. (2000) European Journal of Pharmacology 387:9-17.) Fasoracetam may stimulate adenylate cyclase activity through activation of group I mGluRs, while it may also inhibit adenylate cyclase activity by stimulating group II and III mGluRs. (Oka M, et al (1997) Brain Research 754:121-130.) Fasoracetam has been observed to be highly bioavailable (79%-97%) with a half-life of 5-6.5 hours in prior human studies (see Malykh A G, et al. (2010) Drugs 70(3): 287-312). Fasoracetam is a member of the racetam family of chemicals that share a five-carbon oxopyrrolidone ring.

The structure of fasoracetam is:

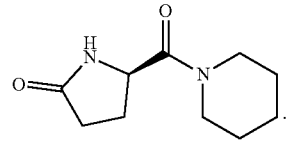 [SMILES: O=C1CC[C@H](C(=O)N2CCCCC2)N1]

The term "fasoracetam" as used herein encompasses pharmaceutically acceptable hydrates and any solid state, amorphous, or crystalline forms of the fasoracetam molecule. For example, the term fasoracetam herein includes forms such as NFC-1: fasoracetam monohydrate. In addition to NFC-1, fasoracetam is also known as C-NS-105, NS105, NS-105, and LAM-105.

NFC-1 has been previously studied in Phase I-III clinical trials in dementia-related cognitive impairment but did not show sufficient efficacy in dementia in Phase III trials. These trials demonstrated that NFC-1 was generally safe and well tolerated for those indications. Phase III data indicated that NFC-1 showed beneficial effects on psychiatric symptoms in cerebral infarct patients and adult dementia patients with cerebrovascular diseases. Fasoracetam is a member of the racetam family of compounds. Another racetam compound, piracetam, has been tested in pediatric ADHD subjects and found to actually increase ADHD symptoms in those subjects compared to a placebo control. (See Akhundian, J., Iranian J. Pediatrics 2001, 11(2): 32-36.)

In each of the method of treatment embodiments, a metabotropic glutamate receptor positive allosteric modulator, a metabotropic glutamate receptor negative allosteric modulator, or a tachykinin-3/neurokinin-3 receptor (TACR-3/NK3R) antagonist may be administered alone or in combination with a nonselective activator of mGluRs, for example, to subjects having an alteration in a mGluR network gene. In some embodiments, the treatment agent comprises ADX63365, ADX50938, ADX71149, AMN082, a 1-(hetero)aryl-3-amino-pyrrolidine derivative, LY341495, ADX48621, GSK1144814, or SB 223412.

VII. Methods of Administration and Dosage

In some embodiments, fasoracetam may be administered as fasoracetam monohydrate (NFC-1). In some embodiments, fasoracetam may be administered by mouth (i.e., per os). In some embodiments, fasoracetam may be administered as capsules, tablets, caplets, oral solutions, and oral suspensions. In some embodiments, fasoracetam capsules or tablets or the like may contain 50 mg, 100 mg, 150 mg, 200 mg, 250 mg, 300 mg, 350 mg, 400 mg, 600 mg, or 800 mg of fasoracetam, or any range bounded by two of the above numbers.

In some embodiments, fasoracetam at any of the 50 mg, 100 mg, 150 mg, 200 mg, 250 mg, 300 mg, 350 mg, or 400 mg dosages above may be administered once daily, twice, or three times daily. In some embodiments, the total daily dose of fasoracetam may be 50 mg, 100 mg, 150 mg, 200 mg, 250 mg, 300 mg, 350 mg, or 400 mg given once-daily or 50 mg, 100 mg, 150 mg, 200 mg, 250 mg, 300 mg, 350 mg, or 400 mg given twice-daily. In some embodiments, fasoracetam dosing may be adjusted using a series of dose escalations. In some embodiments, pharmacokinetic data on drug level or clinical response are used to determine changes in dosing. In some embodiments, dose escalation of fasoracetam is not used. In some embodiments, subjects are treated at a dose of fasoracetam expected to be clinically efficacious without a dose-escalation protocol.

VII. Therapeutic Combinations

In some embodiments, the nonselective activator of mGluR network proteins, such as fasoracetam, is used in combination with other agents for the treatment of ADHD and 22q deletion and/or duplication syndromes. In some embodiments, it is used in combination with current ADHD medications such as stimulant and/or nonstimulant drugs. "Stimulant" drugs used for treatment of ADHD are drugs that increase the levels of dopamine or other neurotransmitters in the brain. They are available in a variety of release forms from short to extended-release. Stimulants tend to improve attention span and focus and to regulate impulsive behaviors. Currently used stimulants include methylphenidates (e.g. Concerta®; Ritalin®; Daytrana® patch; Methylin®; Metadate®), dexmethylphenidates (e.g., Focalin®), and amphetamines such as Adderall XR® (amphetamine mixed salts), Dexedrine® (dextroamphetamine), and Vyvanse® (lisdexamphetamine dimesylate).

"Nonstimulant" (also referred to herein as "non-stimulant") drugs for ADHD are drugs that may affect neurotransmitters but do not raise dopamine levels in the brain. Nonstimulants encompass a variety of drug classes. Currently used nonstimulant drugs include atomoxetine (Strattera®), which may prolong the action of norepinephrine in the brain, as well as the blood-pressure medications clonidine (Kapvay®) and guanfacine (Intuniv®), which may also improve mental functioning in ADHD patients.

In some embodiments, the activator may be used in combination with an anxiolytic (such as barbiturates, pregabalin, or benzodiazepines, including chlordiazepoxide, clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam). It may also be used in combination with antidepressants such as serotonin selective uptake inhibitors, e.g. fluoxetine, sertraline, and citalopram. Antidepressants include, for example, fluoxetine, escitalopram, bupropion, mirtazapine, amitriptyline, imipramine, venlafaxine, sertraline, paroxetine, or other compounds in the classes of tricyclic antidepressants, selective serotonin reuptake inhibitors, serotonin and norepinephrine reuptake inhibitors, norepinephrine and dopamine reuptake inhibitors, monoamine oxidase inhibitors, or other drugs approved for the use of depression). In some embodiments, the other agent may be a beta-blocker (such as acebutolol, atenolol, betaxolol, bisoprolol, esmolol, nebivolol, metoprolol, cartelol, penbutolol, pindolol, carvedilol, labetalol, levobunolol, metipranolol, nadolol, propranolol, sotalol, timolol, or other selective or nonselective blockers of beta-adrenergic receptors). In some embodiments, the other agent may be an anti-psychotic drug such as aripiprazole or risperidone.

In some embodiments, fasoracetam may be used in combination with a non-pharmacologic treatment, such as psychotherapy or brain stimulation therapies. For example, in some embodiments the patient is further treated with brain stimulation, which may be vagus nerve stimulation, repetitive transcranial magnetic stimulation, magnetic seizure therapy, deep brain stimulation, or any other therapies involving modulation of brain function by electricity, magnets, or implants.

IX Efficacy Measures for Determining Responsiveness to Treatment

A number of different outcome measures or rating scales are validated for determining the efficacy of a treatment for ADHD, for example, in clinical trials. These can include measures of attention, tasks, and global measures of the severity or improvement of patients. Rating scales currently used in ADHD clinical trials in pediatric patients include the ADHD Rating Scale IV, Vanderbilt scale, actigraphy, Quotient ADHD test scale, and the PERMP-Math test scale. A Clinical global impressions severity/improvement (CGI-S and CGI-I) score is also frequently used as a secondary efficacy measurement as it may correspond well to the judgments of global well-being that clinicians make in their normal clinical practice of treating ADHD patients.

The ADHD Rating Scale IV is based on 18 inattentive and hyperactive/impulsive diagnostic criteria for ADHD provided in the Fourth Edition of the Diagnostic and Statistical Manual of Mental Disorders, 1994, (DSM-4) or the Fifth Edition, 2016, (DSM-V), published by the American Psychiatric Association. [Are the DSM-IV and DSM-V questions essentially the same?] Each of the 18 items is scored on a 4-point scale of 0, 1, 2, or 3, with 0 indicating no symptoms to 3 indicating severe symptoms. Accordingly, the Scale results in possible scores ranging from 0 to 54 with a higher score reflecting a more severe disease condition. There are a few versions of the ADHD Rating Scale IV depending upon who is recording the information, a parent/ teacher or a clinician, and depending upon whether the patient is a pediatric or adult patient. But all versions are designed to assess the same set of 18 items.

The Vanderbilt Rating Scale is a measure that can be completed by parents or teachers (separate forms, see Vanderbilt Rating Scale Parents and Vanderbilt Rating Scale Teachers). The Vanderbilt scale rates the child's behavior on items such as attention, finishing tasks, hyperactivity, difficulty waiting, and measures of conduct or oppositional defiant disorders—as well as measures of overall school performance and interactions with others. The first 18 items on the Vanderbilt scale correspond to those of the ADHD Rating Scale IV above while the Vanderbilt scale also includes items 19-47 related to other mental disorders including ODD (items 19-26), conduct disorder (items 27-40), anxiety (items 41, 42, and 47), and depression (items 43-46). Each of the behavioral assessment items on the Vanderbilt Scale are rated 0, 1, 2, or 3, with 0=never occurring; 1=occasionally, 2=often, and 3=very often. Thus, the ADHD Rating Scale IV, ADHD Rating Scale V, and items 1-18 of the Vanderbilt Rating Scale are equivalent scales, while additional items on the Vanderbilt Scale assess co-morbid phenotypes and disorders.

The first 18 items of the Vanderbilt Rating Scale Parents are in the form of a questionnaire and include items such as: (3) does not seem to listen when spoken to directly; (4) does not follow through when given directions and fails to finish activities (not due to refusal or failure to understand); (9) is forgetful in daily activities; (10) fidgets with hands or feet or squirms in seat; (16) blurts out answers before questions have been completed; (17) has difficulty waiting his or her turn. Each of the items are rated on a scale of 0, 1, 2, or 3, with 0=never; 1=occasionally, 2=often, and 3=very often. A total score of 0 to 54 is computed based on the answers to the 18 questions.

As used herein an "ADHD rating scale score," "ADHD score" or "Vanderbilt ADHD score" are used interchangeably to refer to the computed score of the 18 items of the ADHD Rating Scale IV or V or the first 18 items of the Vanderbilt Rating Scale in any of their associated versions, e.g., for parent, teacher, or clinician to complete, and for a pediatric subject or adult subject. Clinical trials may assess the impact of drug or placebo on the ADHD score or Vanderbilt ADHD score (i.e. the score of 0 to 54 based on the first 18 items in the ADHD or Vanderbilt rating scale). In some cases, results of a clinical trial population may be analyzed by comparing the average score or a percentage change in score over time of administration of drug. Patients may be considered "improved," for example, if their Vanderbilt ADHD score is reduced by at least 25% compared to a placebo or pre-study baseline, and "robustly improved," for example, if their score is reduced by at least 40% compared to a pre-study or placebo baseline.

Some embodiments of methods of treatment herein refer to administering to a subject an amount of a nonselective mGluR network activator effective to reduce an ADHD rating scale score or Vanderbilt ADHD score by at least 25%, such as at least 30% or at least 35% or at least 40%, after a certain period of treatment, such as 1, 2, 3, 4 or 5 weeks, in a majority of clinical trial subjects. In such embodiments, the amount for administration may, for example, be selected based on clinical results showing that the amount led to such a result in a majority of previously assessed clinical patients. For example, if a subject to be treated is a pediatric subject, the treatment amount may be selected on the basis of achieving such results in a majority of patients in a clinical trial of pediatric subjects.

The Clinical Global Impression Scale (CGI) is a widely-used assessment instrument in psychiatry and is a common secondary efficacy measure for ADHD clinical trials. The CGI scale generally asks the clinician to provide a global assessment of the patient's function, symptoms, and adverse events based on the clinician's experience with ADHD patients. The CGI scale has two component measurements, CGI-S (clinical global impression—severity; a measure of disease severity) and CGI-I (clinical global impression—improvement; a measure of improvement in symptoms). Both scales range from 1 to 7. The CGI-S scale ranges from 1 (normal) to 3 (mildly ill), 4 (moderately ill), 5 (markedly ill), 6 (severely ill) and 7 (among the most extremely impaired). The CGI-I scale ranges from 1 (very much improved), 2 (much improved), 3 (minimally improved), 4 (no change), 5 (minimally worse), 6 (much worse), to 7 (very much worse). In general, subjects with a CGI-I score of 1 or 2 compared to a base-line or placebo level are considered responders to a treatment regimen. For example, in some cases a responder to a drug regimen may show a reduction in ADHD score or Vanderbilt ADHD score of at least 25%, such as at least 30%, at least 35%, or at least 40%, as well as a CGI-I score of either 1 or 2 after a certain period of treatment, such as 1, 2, 3, 4, or 5 weeks. In some cases, a responder may show a change in CGI-I score after 1, 2, 3, 4, or 5 weeks, for example, of 1 to 2 points. In some cases, a responder may show a CGI-S score of 1 or 2 or 3 after 1, 2, 3, 4, or 5 weeks In some embodiments of the methods herein, the amount of nonselective mGluR activator administered to a subject is chosen based on that amount's ability to give a CGI-I score of 1 or 2 in a majority of subjects in a clinical trial, for example a clinical trial of similar subjects. Thus, for example, if a pediatric clinical trial shows that a particular amount of activator gives a CGI-I score of 1 or 2 in a majority of patients in the trial after a particular period of time, that amount may be chosen to give to another pediatric subject as a treatment dose. Similarly, in some embodiments, the amount of nonselective mGluR activator administered to a subject is chosen based on an amount that gave a reduction of at least 25%, such as at least 35%, at least 35%, or at least 40% in Vanderbilt ADHD score in a clinical trial of similar subjects. In some embodiments, an amount is chosen for administration based on the amount that achieved a CGI-S score of 1-3, such as 1-2 in subjects after a period of treatment. In some cases, an amount is chosen for administration that gave a combination of these effects in a majority of clinical trial subjects.

The Permanent Product Measure of Performance (PERMP)-Math is an individualized mathematics test that can be performed by a patient periodically when on and off medication for ADHD. It is used, for example, to monitor classroom performance in an experimental laboratory setting.

In general, the PERMP test comprises 5 pages of 400 problems that subjects are directed to attempt over a 10-minute period. Subjects may be given a pre-test first to determine their mathematical skill level. Subjects are directed to answer as many questions as they can in the 10-minute period and the test is generally scored on a 0-800-point scale based on the number of questions attempted and the number of questions answered correctly within the time limit. Subjects receive a different version of the test at each setting.

Quotient ADHD scores use a medical device to measure hyperactivity, attention, and impulsivity in patients with ADHD. The Quotient ADHD tool uses motion tracking technology to track a patient's micro-movements while they complete a 15-20-minute computerized test. Following the patient's completion of the test, patterns of motions, the accuracy of responses, and fluctuations in attention state can be analyzed.

Actigraphy is non-invasive monitoring of human rest/activity cycles, using an actigraph worn by the patient to document body movements. Actigraphs can be worn during school, for example, to measure activity levels. Actigraphy analysis can measure changes in sleep and hyperactivity that may be seen with treatment for ADHD.

Additional questionnaires may also be used by clinicians to assess co-morbid symptoms such as anger control and disruptive behaviors as well as to assess co-morbid disease conditions.

X. Articles of Manufacture

In some embodiments, the invention comprises articles of manufacture that may be used in the methods and treatments described herein. In one embodiment, the manufacture is a solid support or microarray for use in detecting genetic alterations in some, or all, of the mGluR network genes listed in FIGS. 1-3 (i.e., Tiers 1-3). In some embodiments, genes contained in multiple Tiers are assessed within the same solid support or microarray. In some embodiments, certain mGluR network genes are excluded. In some embodiments, the GRM genes are excluded.

Thus, for example, in some embodiments in which mGluR network genes are assayed to determine if there is a genetic alteration in one or more of the genes, such as a CNV, a solid support or microarray, such as on a chip, is used that contains appropriate probes for determining the presence of genetic alterations in 10, 20, 30, 40, 50, 60, 70 or all of the Tier 1 genes. In some embodiments, the solid support or microarray may also include appropriate probes for determining the presence of genetic alterations in at least 10, 20, 30, 50, 100, 150, or all of the Tier 2 genes. In some embodiments, it may further include appropriate probes for determining the presence of genetic alterations in at least 10, 20, 50, 100, 200, 300, 400, 500 or all of the Tier 3 genes. For example, such a solid support, microarray, or chip may be used to determine the presence of genetic alterations such as CNVs or SNVs in the Tier 1, Tier 1+2, or Tier 1+2+3 mGluR gene networks as part of a method of treating an ADHD or 22q deletion and/or duplication patient.

In some embodiments, the manufacture is a set of probes for mGluR network genes of interest from Tiers 1, 2, and/or 3. In some embodiments the probes are labelled. In certain embodiments, the labels are non-naturally occurring. Similarly, sets of probes may be manufactured for determining the presence of genetic alterations in 10, 20, 30, 40, 50, 60, 70 or all of the Tier 1 genes. In some embodiments, probes may be manufactured for determining the presence of genetic alterations in at least 10, 20, 30, 50, 100, 150, or all of the Tier 2 genes. In some embodiments, probes may further include those for determining the presence of genetic alterations in at least 10, 20, 50, 100, 200, 300, 400, 500 or all of the Tier 3 genes. These various probe sets may be used in methods of determining the presence of genetic alterations, such as CNVs and SNVs in the Tier 1, Tier 1+2, or Tier 1+2+3 mGluR gene networks as part of a method of treating an ADHD or 22q deletion and/or duplication patient
EXAMPLES Example 1: Treatment of ADHD Patients with CNVs in mGluR Network Genes with NFC-1 (Fasoracetam Monohydrate)

An open-label Phase Ib clinical trial was initiated to investigate the safety, pharmacokinetics and efficacy of NFC-1 (fasoracetam monohydrate) in adolescent subjects between the ages of 12 and 17 previously diagnosed with ADHD who also had at least one genetic alteration in an mGluR network gene.

The study included 30 subjects who were between ages 12 and 17, of any ancestry or race, and of weight within the 5th to 95th percentile for their age, and otherwise judged to be in good medical health. The subjects suffered from ADHD as defined by the Diagnostic and Statistical Manual of Mental Disorders, 5th Ed (DSM-5) and a Vanderbilt ADHD score of greater than or equal to 16 (as determined by parent or teacher) at baseline either with or without conventional ADHD therapy. Subjects were genotyped and included in the trial if they possess at least one genetic alteration in the form of at least one copy number variation (deletion or duplication) in an mGluR network gene that potentially disrupts the function of the gene. Seventeen of the 30 subjects have a CNV in a Tier 1 mGluR network gene, while 7 subjects have a CNV in a Tier 2 gene and 6 in a Tier 3 gene. Two of the 30 ADHD subjects of the trial also suffered from 22q syndrome, one with 22q deletion syndrome and one with 22q duplication syndrome. Several trial subjects showed evidence of co-morbid phenotypes such as anxiety, mood disorders, sleep disturbance such as insomnia, depression, ODD, or conduct disorder in addition to ADHD at enrollment, based on the results of items 19-47 of the Vanderbilt Scale.

Exclusion criteria comprised subjects suffering from a clinically significant illness, either mental or physical, that, in the investigator's opinion, might confound the results of the study or that might prevent them from completing the study, subjects that are pregnant or nursing, subjects that test positive for illicit drugs of that have a history of drug abuse, subjects that consume alcoholic beverages, or subjects for which the investigator is otherwise concerned regarding their compliance or suitability.

NFC-1 capsules of either 50 mg or 200 mg comprising fasoracetam monohydrate as active ingredient and placebo capsules comprising microcellulose were used for the study. The design of the trial was a phone screening (1 day), enrollment phase (1 to 2 days), a wash-out phase for subjects currently on ADHD medications (1-14 days), pharmacokinetic (PK) assessment (2 days), followed by a dose-escalation phase (35 days) and a follow-up phone visit approximately four weeks after the last dose, for a maximum of 127 days. All ADHD medications were discontinued during the wash-out phase prior to the study. The wash-out period for stimulants was 2-3 days and that for atomoxetine or noradrenergic agonists was 10-12 days. No new ADHD medications were started during the study.

All subjects participated in the PK assessment. For the PK portion of the trial, subjects received a one-time dose of 50 to 800 mg NFC-1 and blood samples were taken just prior to dosing and at 0.5. 1, 1.5, 2, 3, 4, 6, 8, 12, and 24 hours after dosing. The 30 subjects were placed into 5 groups of 6 subjects for PK and initial safety assessment, each group receiving a different dose ranging of 50, 100, 200, 400, or 800 mg. The PK parameters Cmax, Tmax, and AUCO-24 h were calculated based on NFC-1 levels in serum.

Dose-escalation phase of the trial followed the PK and initial safety assessment and ran over a 5-week period. During week 1, all subjects were administered placebo capsules twice daily. After one week of placebo treatment, patients were started on 50 mg bid NFC-1 for 1 week. If safety and responsiveness data from prior dose level of fasoracetam indicated it was appropriate, subjects were then escalated to the next higher dose (100, 200, or 400 mg).

Subjects who showed tolerance to the 50 mg bid dose as well as response to the drug were to be maintained at that level for the remaining 3 weeks of the trial. Subjects who showed tolerance but lack of response or partial response to the 50 mg bid dose were to be moved up to the next higher dose of 100 mg during the following week. Subjects who showed tolerance at 100 mg but lack of response or partial response were to be moved up to the 200 mg dose the following week while those who showed both tolerance and response at 100 mg were to be kept at 100 mg bid for the remainder of the trial. Similarly, subjects moved up to the 200 mg dose who showed both tolerance and response were to be kept at 200 mg for the final week of the trial while those showing tolerance but lack of response or partial response were moved to a 400 mg dose for the final week. Of the 30 trial subjects, 3 received a maximum dose of 100 mg, 9 received a maximum dose of 200 mg, and the remaining 18 received a maximum dose of 400 mg.

All efficacy assessments, except actigraphy, were made at study enrollment ("enrollment baseline") and again, including actigraphy, once-per-week for the placebo week ("week 1" or "placebo baseline") and at each of the 4 weeks of NFC-1 treatment. These efficacy measures include items 1-18 of the Vanderbilt scale assessing symptoms related to inattentiveness and hyperactivity-impulsiveness as well as additional questions 19-47 of the Vanderbilt scale assessing other behavioral symptoms (conducted by parent), actigraphy for quantitative measurement of activity, Quotient® ADHD test for objective measurement of micro-motion and shifts in attention state, PERMP-Math test, and CGI-I and CGI-S for assessment of global functioning. Prior to receiving the PK assessment dose, subjects returned to the clinic to be administered the PERMP-Math tests, subjected to actigraphy (set to activate at the time of first placebo dose 2 days later), and to be given a general physical examination including vital signs and weight, blood and urine sampling, and a pregnancy test for female subjects. During the 5-week placebo and dose-escalation phases of the study, subjects visited the clinic again at the end of each week to be administered the Quotient® and PERMP-Math tests, subjected to actigraphy, Vanderbilt and BRIEF measurements (conducted by parent), and to be given a general physical examination including vital signs and weight, blood and urine sampling, and a pregnancy test for female subjects.

For data analysis, subjects were considered as a whole as well as by genetic tier (1, 2, or 3) or by genetic tier group (1 and 2 vs. 3). The subject number, maximum dose administered, age, genetic tier, and the placebo baseline (i.e. week 1) and final (i.e. week 5) CGI-I, Vanderbilt, and PERMP results for all of the 30 subjects are shown in Table 1 below. Subjects 110 and 127 suffer from both ADHD and 22q deletion and/or duplication syndromes. Thirteen subjects had a diagnosis of ODD, and one of these subjects did not complete the trial. Thus, twelve subjects, numbers 102, 103, 108, 111, 112, 114, 117, 122, 125, 126, 128, and 130 suffer from both ADHD and ODD and completed the trial.

See, Table 1 on next page (remainder of page intentionally left blank).

TABLE 1

Overall Study Placebo Baseline to Final Results

| Subject Number | Max Dose | Age | Genetic Tier | Genetic Tier Group | Baseline CGI = I | Baseline Vanderbilt | Baseline PERMP | Final CGI = I | Final Vanderbilt | Final PERMP | Change in CGI = I | Change in Vanderbilt | Change in PERMP |
|---|---|---|---|---|---|---|---|---|---|---|---|---|---|
| 101 | 200 | 14 | 2 | 1/2 | 4 | 47 | 73 | 2 | 12 | 71 | -2 | -35 | -2 |
| 102 | 200 | 12 | 1 | 1/2 | 5 | 41 | 104 | 3 | 39 | 80 | -2 | -2 | -24 |
| 103 | 200 | 17 | 1 | 1/2 | 3 | 38 | 85 | 2 | 30 | 74 | -1 | -8 | -11 |
| 104 | 200 | 14 | 2 | 1/2 | 5 | 37 | 121 | 2 | 23 | 103 | -3 | -14 | -18 |
| 105 | 200 | 15 | 3 | 3 | 4 | 6 | 92 | 2 | 3 | 111 | -2 | -3 | 19 |
| 106 | 100 | 17 | 3 | 3 | 3 | 8 | 78 | 2 | 0 | 101 | -1 | -8 | 23 |
| 107 | 200 | 12 | 1 | 1/2 | 4 | 9 | 72 | 2 | 0 | 76 | -2 | -9 | 4 |
| 108 | 200 | 17 | 1 | 1/2 | 4 | 50 | 129 | 2 | 18 | 160 | -2 | -32 | 31 |
| 109 | 400 | 16 | 1 | 1/2 | 3 | 10 | 130 | 1 | 6 | 87 | -2 | -4 | -43 |
| 110 | 400 | 13 | 1 | 1/2 | 4 | 22 | 45 | 2 | 17 | 71 | -2 | -5 | 26 |
| 111 | 400 | 13 | 1 | 1/2 | 3 | 30 | 97 | 2 | 34 | 88 | -1 | 4 | -9 |
| 112 | 400 | 14 | 2 | 1/2 | 3 | 49 | 70 | 2 | 36 | 93 | -1 | -13 | 23 |
| 113 | 100 | 12 | 1 | 1/2 | 3 | 32 | 125 | 3 | 22 | 125 | 0 | -10 | 0 |
| 114 | 100 | 14 | 1 | 1/2 | 5 | 49 | 133 | 4 | 17 | 135 | -1 | -32 | 2 |
| 115 | 400 | 13 | 2 | 1/2 | 3 | 25 | 59 | 3 | 46 | 48 | 0 | 21 | -11 |
| 117 | 400 | 16 | 1 | 1/2 | 0 | 28 | 56 | 2 | 12 | 68 | 2 | -16 | 12 |
| 118 | 400 | 14 | 1 | 1/2 | 4 | 13 | 78 | 2 | 0 | 92 | -2 | -13 | 14 |
| 119 | 400 | 12 | 2 | 1/2 | 3 | 16 | 76 | 2 | 17 | 64 | -1 | 1 | -12 |
| 120 | 400 | 12 | 1 | 1/2 | 4 | 15 | 99 | 2 | 15 | 99 | -2 | 0 | 0 |
| 121 | 200 | 17 | 1 | 1/2 | 5 | 36 | 125 | 2 | 31 | 55 | -3 | -5 | -70 |
| 122 | 400 | 16 | 1 | 1/2 | 3 | 33 | 96 | 3 | 24 | 80 | 0 | -9 | -16 |
| 123 | 400 | 14 | 2 | 1/2 | 4 | 24 | 75 | 2 | 14 | 71 | -2 | -10 | -4 |
| 124 | 400 | 14 | 3 | 3 | 4 | 33 | 71 | 2 | 12 | 34 | -2 | -21 | -37 |
| 125 | 400 | 17 | 2 | 1/2 | 3 | 39 | 95 | 2 | 23 | 104 | -1 | -16 | 9 |
| 126 | 400 | 17 | 3 | 3 | 4 | 35 | 92 | 3 | 29 | 64 | -1 | -6 | -28 |
| 127 | 400 | 12 | 1 | 1/2 | 6 | 44 | 78 | 2 | 33 | 64 | -4 | -11 | -14 |
| 128 | 400 | 13 | 1 | 1/2 | 3 | 36 | 48 | 1 | 16 | 46 | -2 | -20 | -2 |
| 129 | 400 | 17 | 3 | 3 | 4 |  | 60 | 3 |  | 75 | -1 |  | 15 |
| 130 | 400 | 16 | 3 | 3 | 3 | 36 | 191 | 3 | 35 | 168 | 0 | -1 | -23 |
| 216 | 200 | 17 | 1 | 1/2 | 4 | 2 | 109 | 3 | 1 | 152 | -1 | -1 | 43 |

Based on Table 1, the mean starting and ending CGI-I scores for the 30 subjects are 3.67 at week 1 (placebo baseline) and 2.27 at week 5, for a mean improvement of 1.4. This indicates, in general, that the subjects were "much improved" or "very much improved" on average (CGI-I of 1 or 2) by the end of the dose escalation phase of treatment. The change in CGI-I scores from enrollment baseline to week 5 for the 30 trial subjects are summarized in Tables 2(a)-(c) below. As shown below, the mean improvement in CGI-I score for all subjects is 1.57, which corresponds to a "much improved" to "very much improved" state. Subjects in genetic Tiers 1 and 2 were more improved than those in Tier 3, with P=0.0402.

Tables 2(a), (b), (c): CGI-I at week 5 compared to that at the pre-study enrollment baseline for all subjects, by genetic tier, and by tier group TABLE 2a a) All Subjects

| N | Mean | Std Dev | Median | N missing | $25^{th}$ percentile | $75^{th}$ percentile |
|---|------|---------|--------|-----------|----------------------|----------------------|
| 30 | 1.57 | 1.01 | 2 | 1 | 1 | 2 |

TABLE 2b b) By Genetic Tier

| Genetic Tier | N | Mean | Std Dev | Median | N missing | $25^{th}$ percentile | $75^{th}$ percentile |
|--------------|---|------|---------|--------|-----------|----------------------|----------------------|
| 1 | 16 | 1.81 | 0.91 | 2 | 1 | 1 | 2 |
| 2 | 7 | 1.57 | 1.13 | 1 | 0 | 1 | 3 |
| 3 | 6 | 0.86 | 0.90 | 1 | 0 | 0 | 2 |

TABLE 2c c) By Tier Group

| Genetic Tier | N | Mean | Std Dev | Median | N missing | $25^{th}$ percentile | $75^{th}$ percentile |
|--------------|---|------|---------|--------|-----------|----------------------|----------------------|
| 1 or 2 | 23 | 1.74 | 0.96 | 2 | 1 | 1 | 2 |
| 3 | 7 | 0.86 | 0.90 | 1 | 0 | 0 | 2 |

CGI-S scores declined from an average of about 4 to an average of about 3 from enrollment to week 5. The change in CGI-S score from enrollment baseline to week 5 is shown in Tables 2(d)-(f) below and the mean change was approximately 1 over all subjects.

Table 2(d)-(f): Changes in CGI-S scores from pre-study enrollment baseline to week 5 in all subjects, by genetic tier, and by tier group.

TABLE 2d d) All subjects

| N | Mean | Std Dev | Median | N missing | $25^{th}$ percentile | $75^{th}$ percentile |
|---|------|---------|--------|-----------|----------------------|----------------------|
| 30 | 0.93 | 0.74 | 1 | 1 | 0 | 2 |

TABLE 2e e) By genetic tier

| Genetic Tier | N | Mean | Std Dev | Median | N missing | $25^{th}$ percentile | $75^{th}$ percentile |
|--------------|---|------|---------|--------|-----------|----------------------|----------------------|
| 1 | 16 | 1.125 | 0.87 | 1 | 1 | 1 | 2 |
| 2 | 7 | 1.0 | 0.58 | 1 | 0 | 1 | 1 |
| 3 | 6 | 0.5 | 0.55 | 0.5 | 0 | 0 | 1 |

TABLE 2f f) By tier group

| Genetic Tier | N | Mean | Std Dev | Median | N missing | $25^{th}$ percentile | $75^{th}$ percentile |
|--------------|---|------|---------|--------|-----------|----------------------|----------------------|
| 1 or 2 | 23 | 1.09 | 0.73 | 1 | 1 | 1 | 1 |
| 3 | 7 | 0.43 | 0.53 | 0 | 0 | 0 | 1 |

Table 3 provides an analysis of the percentages of subjects in the total study population and genetic tiers considered responders, i.e. having a CGI-I score of 1 or 2 in each week of the dose escalation phase of the trial. These data are also depicted graphically in FIG. 4. As shown in both Table 3 and FIG. 4, at week 4, about 55% of the subjects were considered responders based on CGI-I score, including 56% in Tier 1 and 50% in Tier 2, while none of the 6 Tier 3 subjects were significant responders. By week 5 of the dose escalation, 83% of the trial subjects were considered responders based on CGI-I score, including 81% and 86% in genetic Tiers 1 and 2 and 40% in genetic Tier 3. In the table below, "N" represents the number of subjects for which a CGI-I score was measured and "%" indicates the percentage of subjects showing a CGI-I score of 1 or 2 compared to the genetic tier group or compared to the total study population (in the "overall" row of the table).

TABLE 3

CGI-I Scores: Proportions of Subjects Responding at Each Study Visit

| Tier | Week1 N | % | Week2 N | % | Week3 N | % | Week4 N | % | Week5 N | % |
|------|---------|---|---------|---|---------|---|---------|---|---------|---|
| 1 | 16 | 0 | 17 | 24 | 15 | 53 | 16 | 56 | 16 | 81 |
| 2 | 7 | 0 | 7 | 43 | 7 | 29 | 6 | 50 | 7 | 86 |
| 3 | 6 | 0 | 6 | 0 | 6 | 0 | 6 | 0 | 5 | 40 |
| Overall | 29 | 0 | 30 | 29 | 28 | 45 | 28 | 55 | 28 | 83 |

Mean Vanderbilt ADHD scores (with standard error) at each week of the study are shown in Table 4 below. These values are calculated using Repeated Measures Analysis of Variance (RMANOVA). This analysis adjusts for within-subject changes in the repeated efficacy measures in order to more readily detect changes attributable to experimental effects. Note that the standard error is identical for each weekly value in Table 4 below because it was estimated from the RMANOVA statistical model. As Table 4 shows, the mean Vanderbilt ADHD score decreased each week from the placebo baseline (week 1) to week 5. The change in within-patient means is also statistically significant (p<0.001), which supports the conclusion that Vanderbilt scores in this population decreased with the time-course of participation in this study.

TABLE 4

Mean Vanderbilt ADHD Scores at each week of the study based on Repeated Measures Analysis for the overall study population

| | Week 1 | Week 2 | Week 3 | Week 4 | Week 5 |
|---|---|---|---|---|---|
| Mean (SEM) | 29.1 (8.1) | 26.4 (8.1) | 24.0 (8.1) | 23.3 (8.1) | 22.5 (8.1) |

Table 5 below presents the number and percent of subjects showing improvement in Vanderbilt ADHD scores each week compared to either pre-study baseline or placebo baseline (week 1) both by genetic tier and by the overall study population. These results are also shown graphically in FIGS. 5a and 5b. An at least 25% decrease in Vanderbilt ADHD score is considered responsive and improved, while an at least 40% decrease in score is considered a robust improvement.

TABLE 5

Number and Percent of Subjects with Improvement in Vanderbilt ADHD Score

| | Week 1 | | Week 2 | | Week 3 | | Week 4 | | Week 5 | |
|---|---|---|---|---|---|---|---|---|---|---|
| Tier | N | % | N | % | N | % | N | % | N | % |
| Relative to Pre-Study (Enrollment) Baseline | | | | | | | | | | |
| 1 | 17 | 47 | 17 | 47 | 16 | 75 | 16 | 88 | 16 | 75 |
| 2 | 7 | 29 | 7 | 29 | 7 | 14 | 7 | 43 | 7 | 86 |
| 3 | 5 | 40 | 4 | 50 | 5 | 40 | 5 | 40 | 4 | 75 |
| Overall | 29 | 41 | 28 | 43 | 28 | 54 | 28 | 68 | 27 | 78 |
| Relative to Placebo (Week 1) Baseline | | | | | | | | | | |
| 1 | — | — | 17 | 29 | 16 | 50 | 16 | 56 | 16 | 56 |
| 2 | — | — | 7 | 29 | 7 | 43 | 7 | 43 | 7 | 71 |
| 3 | — | — | 4 | 0 | 5 | 20 | 5 | 0 | 4 | 0 |
| Overall | — | — | 28 | 25 | 28 | 43 | 28 | 43 | 27 | 52 |

As shown in Table 5 and FIG. 5, 78% of subjects were responsive to treatment based on the Vanderbilt ADHD score at week 5 compared to baseline while 52% were responsive at week 5 compared to placebo baseline. A higher percentage of subjects in genetic Tiers 1 and 2 were responsive compared to subjects in Tier 3. The proportions of patients who were robustly improved at week 5 compared to study baseline and placebo baseline are shown graphically in FIGS. 7a and 7b and are further shown in Table 6. As can be seen from the figures and table, 52% of subjects were robustly improved compared to baseline while 37% were robustly improved compared to placebo baseline and all of those were in the genetic Tiers 1 and 2.

TABLE 6

Number of Subjects Demonstrating Robust Improvement at Each Week

| | Week 1 | | Week 2 | | Week 3 | | Week 4 | | Week 5 | |
|---|---|---|---|---|---|---|---|---|---|---|
| Tier | N | % | N | % | N | % | N | % | N | % |
| Relative to Pre-Study (Enrollment) Baseline | | | | | | | | | | |
| 1 | 17 | 29 | 3 | 35 | 16 | 50 | 16 | 56 | 16 | 63 |
| 2 | 7 | 14 | 7 | 14 | 7 | 0 | 7 | 14 | 7 | 29 |
| 3 | 5 | 40 | 4 | 50 | 5 | 40 | 5 | 40 | 4 | 50 |
| Overall | 29 | 28 | 28 | 32 | 28 | 36 | 28 | 43 | 27 | 52 |
| Relative to Placebo (Week 1) Baseline | | | | | | | | | | |
| 1 | — | — | 17 | 12 | 16 | 44 | 16 | 50 | 16 | 44 |
| 2 | — | — | 7 | 0 | 7 | 0 | 7 | 14 | 7 | 43 |
| 3 | — | — | 4 | 0 | 5 | 0 | 5 | 0 | 4 | 0 |
| Overall | — | — | 28 | 7 | 28 | 25 | 28 | 32 | 27 | 37 |

As shown in Table 1, 18 of the 30 subjects in the study completed the dose escalation to 400 mg bid at week 5. The proportion of those 18 subjects who show improvement (i.e. response) and robust improvement in Vanderbilt ADHD scores at week 5 compared to the pre-study baseline or to the week 1 placebo baseline is shown in Tables 7 and 8 and FIGS. 7 and 8, respectively.

TABLE 7

Number and Percent of Subjects Completing the Dose Escalation to 400 mg bid that Show Improvement in Vanderbilt ADHD Scores Compared to Pre-Study Baseline and Week 1 Placebo Baseline

| | Week 1 | | Week 2 | | Week 3 | | Week 4 | | Week 5 | |
|---|---|---|---|---|---|---|---|---|---|---|
| Tier | N | % | N | % | N | % | N | % | N | % |
| Relative to Pre-Study (Enrollment) Baseline | | | | | | | | | | |
| 1 | 9 | 56 | 9 | 56 | 9 | 89 | 9 | 89 | 9 | 89 |
| 2 | 5 | 40 | 5 | 20 | 5 | 20 | 5 | 20 | 5 | 80 |
| 3 | 3 | 0 | 3 | 33 | 3 | 0 | 3 | 0 | 3 | 67 |
| Overall | 17 | 41 | 17 | 41 | 17 | 53 | 17 | 53 | 17 | 82 |
| Relative to Placebo (Week 1) Baseline | | | | | | | | | | |
| 1 | — | — | 9 | 22 | 9 | 44 | 9 | 44 | 9 | 56 |
| 2 | — | — | 5 | 0 | 5 | 20 | 5 | 20 | 5 | 60 |
| 3 | — | — | 3 | 33 | 3 | 33 | 3 | 0 | 3 | 0 |
| Overall | — | — | 17 | 14 | 17 | 36 | 17 | 36 | 17 | 57 |

TABLE 8

Number and Percent of Subjects Completing the Dose Escalation to 400 mg bid that Show Robust Improvement in Vanderbilt ADHD Scores Compared to Pre-Study Baseline and Week 1 Placebo Baseline

| | Week 1 | | Week 2 | | Week 3 | | Week 4 | | Week 5 | |
|---|---|---|---|---|---|---|---|---|---|---|
| Tier | N | % | N | % | N | % | N | % | N | % |
| Relative to Pre-Study (Enrollment) Baseline | | | | | | | | | | |
| 1 | 9 | 22 | 9 | 44 | 9 | 44 | 9 | 56 | 9 | 67 |
| 2 | 5 | 20 | 5 | 20 | 5 | 0 | 5 | 20 | 5 | 20 |
| 3 | 3 | 0 | 3 | 33 | 3 | 0 | 3 | 0 | 3 | 33 |
| Overall | 17 | 18 | 17 | 35 | 17 | 24 | 17 | 35 | 17 | 47 |

TABLE 8-continued

Number and Percent of Subjects Completing
the Dose Escalation to 400 mg bid
that Show Robust Improvement in Vanderbilt
ADHD Scores Compared to Pre-Study
Baseline and Week 1 Placebo Baseline

| Tier | Week 1 | | Week 2 | | Week 3 | | Week 4 | | Week 5 | |
|---|---|---|---|---|---|---|---|---|---|---|
| | N | % | N | % | N | % | N | % | N | % |
| Relative to Placebo (Week 1) Baseline | | | | | | | | | | |
| 1 | — | — | 9 | 11 | 9 | 44 | 9 | 33 | 9 | 33 |
| 2 | — | — | 5 | 0 | 5 | 0 | 5 | 0 | 5 | 40 |
| 3 | — | — | 3 | 33 | 3 | 0 | 3 | 0 | 3 | 0 |
| Overall | — | — | 17 | 7 | 17 | 29 | 17 | 21 | 17 | 36 |

Based on the data in Table 1, the mean change in PERMP score from pre-study baseline to week 5 was negative 3.43. When analyzed based on genetic tier, there were no significant differences from the overall mean change. Those in Tiers 1 and 2 had a mean change in PERMP of negative 3.0 (mean of negative 3.35 for Tier 1 and negative 2.14 for Tier 2) while those in Tier 3 had a mean change of negative 5.17. While the PERMP scores showed little change, this may be due at least in part to uncontrolled environmental factors due to the way in which the PERMP test was conducted. The test was conducted at the time of clinic visits and thus, for each subject, was not necessarily given at the same time post dose or same time of day from one week to the next. The test was also conducted during a clinic visit and not in a classroom setting. Thus, clinic waiting room distractions, for example, could have varied from one visit to the next and were not controlled.

Overall, the parent-assessed Vanderbilt ADHD scores show that about 75-80% of the subjects had at least a 25% reduction in score at the end of the dose escalation phase of the study (i.e., the end of week 5) compared to pre-study baseline. About 63% of subjects showed a robust improvement, i.e., a change in Vanderbilt ADHD score of at least 40%. In addition, about 80-85% of subjects showed a CGI-I score of 1 or 2 at week 5, indicating that they were much improved or very much improved by week 5 of the study compared to pre-study baseline. PERMP results did not show significant change over the course of the study.

The results from actigraphy demonstrated significant reduction in bursts of medium/high intensity movements at the highest dose of NFC-1 (400 mg bid) in comparison with placebo (P<0.001). As shown in FIGS. 9a-9c, the observed reduction in moderate to vigorous physical activity (MVPA) from week 1 (placebo) to week 5 for genetic Tier-1 (FIG. 9a); genetic Tier-2 (FIG. 9b); and genetic Tier-3 (FIG. 9c) was most prominent in 400 mg bid dose group.

The results from the QUOTIENT® ADHD test demonstrated a high level of noise. Nonetheless, as shown in FIG. 10, clinical trial subjects in the Tier-1 genetic group had significant improvement in the test's measure of inattention between week 1 (placebo) and week 5 (400 mg twice daily) as can be seen by the reduction in inattention in the Tier-1 group (P<0.05) from a normalized inattention value of just over 100 to about 90 between weeks 4 and 5 of the dose escalation.

Subjects 110 and 127 of the study, both in genetic Tier 1, have either a deletion or a duplication at 22q that comprises the RANBP1 gene, an interactor of mGluR3, and thus have a 22q syndrome in addition to a diagnosis of ADHD. Both subjects completed the entire dose escalation to 400 mg bid by week 5 of the study. Subject 110 had a measured IQ of 91 prior to the study, showed a 1-point improvement in CGI-S by week 5 compared to week 1 indicating a change from moderately to mildly ill, and a CGI-I of 2 indicating much improvement. Subject 110 also showed a change in Vanderbilt ADHD score of 5 points from 22 to 17 by week 5 compared to week 1. Subject 127 had a measured IQ of 65 prior to the study, had a CGI-S of 6 at week 1 indicating a severe disease and improved 2 points in CGI-S to 4, denoting moderate disease by week 3 and maintained that improvement through to week 5. Subject 127, like subject 110, also had a CGI-I of 2, indicating that the subject was much improved in the clinician's opinion by end of the dose escalation. Subject 127 also showed a robust decrease in Vanderbilt ADHD score at week 3 from 44 to 25, although no Vanderbilt ADHD score was provided at week 4, and the score at week 5 was 33. The overall CGI, Vanderbilt ADHD and PERMP results for subjects 110 and 127 are shown in the table below. Both of these 22Q subjects had improvement in 22Q symptoms while taking NFC-1, including improvements in abnormal social skills/interactions, lack of engagement, anxiety, mood swings, depression, inattention, hyperactivity and reduced performance at school (in life in general). Thus, NFC-1 is useful in 22q syndrome patients.

TABLE 9

Weekly Data for 22q Syndrome Subjects 110 and 127

| Test | Enrollment | Week 1 | Week 2 | Week 3 | Week 4 | Week 5 |
|---|---|---|---|---|---|---|
| Subject 110 | | | | | | |
| CGI-S | 4 | 4 | 4 | 4 | 4 | 3 |
| CGI-I | — | 4 | 3 | 2 | 2 | 2 |
| Vanderbilt | 33 | 22 | 20 | 17 | 16 | 17 |
| PERMP | 36.5 | 45 | 55 | 51 | 75 | 71 |
| Subject 127 | | | | | | |
| CGI-S | 5 | 6 | 6 | 4 | 4 | 4 |
| CGI-I | — | 6 | 3 | 2 | 2 | 2 |
| Vanderbilt | 41 | 44 | 45 | 25 | nd | 33 |
| PERMP | 60.5 | 78 | 167 | 68 | 72 | 64 |

"nd" indicates no data submitted and "—" indicates measurement not taken.

Thirteen out of the thirty subjects enrolled in the trial demonstrated symptoms of ODD as well as ADHD. Subjects were identified as ODD from the K-SADS-P V6 performed at screening and Vanderbilt scores for ODD at screening and at week 1(scores of 2 or 3 on at least 4 of the 8 Vanderbilt items that assess ODD, i.e., items 19 to 26). By the end of the dose escalation phase of the trial at week 5, four of the twelve subjects (nos. 108, 117, 125, and 128) no longer met the screening criteria for ODD. Of the remaining eight, four showed improvements of 2 or more points from week 1 to week 5.

Subject 108, whose enrollment and week 1 placebo baseline scores on items 19-26 ("Vanderbilt ODD scores") were 23 and 19, respectively, out of a maximum score of 24, by the end of week 5 had a score of 7 out of 24 with no individual scores above 2. Subject 117 had a placebo baseline Vanderbilt ODD score of 19 and a week 5 score of 8 with only one question with a score of 2. Subject 128 had enrollment and placebo Vanderbilt ODD baseline scores of 23 and 24, respectively that fell to 8/24 by week 5 with no individual score above 1. In addition, by the end of week 5, the Vanderbilt ODD scores for all 13 of the subjects were improved from week 1 to week 5. Eleven out of the 13 subjects showed improvement of at least 3 points while 6 out of the 13 showed improvement of at least 8 points from week 1 to week 5.

In addition, 3 out of the 13 subjects screening positive for ODD at enrollment were on anti-psychotic medications both at enrollment and throughout the study. Subjects 111 and 126 were on Abilify® (aripiprazole) while subject 122 was on Risperdal® (risperidone). The Vanderbilt ODD scores for each of those 3 subjects nonetheless improved between weeks 1 and 5.

One subject screening positive for ODD (no. 130) also screened positive for conduct disorder (CD), based on scores of 2 or 3 for 3 out of the 15 behaviors assessed by items 27-40 of the Vanderbilt Scale at enrollment and again at week 1. By week 5, that individual's Vanderbilt ODD score improved by 3 points from 24/24 at week 1 to 21/24 and Vanderbilt CD score improved by 4 points from 16/16 at week 1 to 12/16 at week 5.

Certain subjects in the study also displayed other co-morbid phenotypes such as anxiety, depression, mood disorders, and sleep disturbances such as insomnia, according to the information recorded in the enrollment and week 1. Two subjects had maximum scores of 3 on 2 of the 3 Vanderbilt items 41, 42, and 47 that are related to anxiety at enrollment. At week 5, these subjects scored 3 on all 3 items. One of those subjects also scored 3 on 3 of the 4 Vanderbilt items related to depression (items 43-46) at enrollment and scored 3 on all 4 items at week 1. By week 5, this subject scored either 1 or 2 on all 4 items, indicating improvement in depression symptoms.

Results of the BRIEF scale were also analyzed for changes in anxiety/mood scores in all 30 subjects. The BRIEF scale, performed by parents, includes a set of items that relate to anxiety and mood, specifically the following:
1. Over-reacts to small problems;
6. Upset with new situations;
7. Explosive-angry outbursts;
12. Upset by changes in plans;
13. Disturbed by change of teacher/class;
20. Easily tearful;
23. Resists change of routine, foods, plans;
25. Outbursts for little reason;
26. Mood changes frequently;
30. Trouble getting used to new situations;
45. Reacts more strongly to situations than other children;
50. Mood easily influenced by situation;
62. Angry or tearful outbursts are intense but end suddenly;
64. Small events trigger big reactions; and
70. Becomes upset too easily.

The answers to these questions are scored as "never," "sometimes," or "often." The BRIEF test was administered at enrollment and again after each week of the dose escalation treatment from placebo week to week 5. All scores for all 30 subjects for each question above were added up for enrollment and week 5, giving 1 point for each "never" or "often" score. It was found that the total "never" score for all questions for all subjects at enrollment was 125 and at week 5 was 191, showing a trend toward improvement. Similarly, the total "often" score at enrollment was 154 while the total "often" score at week 5 was 77, again showing a trend toward improvement in anxiety and mood symptoms.

Example 2: Phase 2 Study of Treatment of ADHD Patients with CNVs in mGluR Network Genes with NFC-1 (Fasoracetam Monohydrate)

A randomized, double-blind, placebo-controlled, parallel-group phase 2 study of ADHD subjects 12-17 years old is conducted to compare the safety and efficacy of NFC-1 with that of placebo. Approximately 90 male and female subjects will receive randomized treatment with NFC-1 or placebo to obtain 80 subjects that complete the study as planned. Subjects have ADHD as defined by the Diagnostic and Statistical Manual of Mental Disorders, 5th edition (DSM-5) and Version 5 of the Attention Deficit Hyperactivity Disorder Rating Scale (ADHD RS-5)>28 at Baseline with or without conventional ADHD therapy. About 45 subjects will be in each treatment group.

Subjects will be randomly assigned to receive either NFC-1 or placebo on Day-1 and will start taking the product at a dose of 100 mg twice daily on Day 1. Dosing will be optimized to 100 mg, 200 mg, or 400 mg twice daily, as appropriate, over the 4 weeks of treatment (dose optimization phase), based on clinical response and tolerability. If the subject tolerates a dose well, the dose will be maintained for an additional 2 weeks (dose maintenance phase) when the primary assessments of efficacy and tolerability will be performed. Efficacy will be assessed by the ADHD rating scale score, CGI-I, CGI-S, the Adolescent Sleep Hygiene Scale (ASHS), and the Screen for Childhood Anxiety-related Emotional Disorders (SCARED). The ASHS is a self-report questionnaire assessing sleep practices theoretically important for optimal sleep in adolescents aged ≥12 years of age. It assesses physiological (e.g., evening caffeine consumption), cognitive (e.g., thinking about things that need to be done at bedtime), emotional (e.g., going to bed feeling upset), sleep environment (e.g., falling asleep with the lights on), sleep stability (e.g., different bedtime/wake time pattern on weekdays and at weekends), substance use (e.g., evening alcohol use), daytime sleep (e.g., napping), and having a bedtime routine. The SCARED is a child self-report instrument for ages 8-18 years used to screen for childhood anxiety disorders including general anxiety disorder, separation anxiety disorder, panic disorder, and social phobia. In addition, it assesses symptoms related to school phobias. The SCARED consists of 41 items and 5 factors that parallel the DSM-IV classification of anxiety disorders. The scale has good internal consistency, test-retest reliability, and discriminant validity, and it is sensitive to treatment response. Safety and adverse events will also be assessed during the study.

Example 3: A 12-Week, Double-Blind, Placebo-Controlled, Randomized Withdrawal Study of NFC-1 (Fasoracetam Monohydrate) in Subjects with 22q11.2 Deletion Syndrome A 12-week Phase I trial will be conducted to assess safety and tolerability of twice-daily oral doses of NFC-1 in subjects 12-17 years with 22q11.2 deletion syndrome (22q11DS) with concomitant neuropsychiatric disease: ADHD and/or autism spectrum disorder (ASD). Five weeks of open-label dose optimization will be followed by 7 weeks of double-blind, placebo-controlled, randomized withdrawal assessment in subjects 12-17 years old. About 40 subjects will be initiated, dose optimized, and maintained on NFC-1 over a period of 5 weeks.

Doses will be administered orally twice daily and will be optimized to 50. 100, 200 or 400 mg twice daily as appropriate over the initial 5 weeks. Response to treatment is defined as achieving significant improvement in symptoms as indicated by a CGI-I score of <3 and a CGI-S score of <4 after 5 weeks of dose optimization.

At the end of Week 5, subjects will be randomized to NFC-1 or placebo if they have a CGI-I score of <3 and a CGI-S score of <4 (responders) in order to conduct the 7-week withdrawal phase of the trial. Subjects in the withdrawal phase will then be assessed for maintenance of efficacy or treatment failure (defined as a 2 or more-point increase in CGI-S compared to scores at the end of Week 5) over the subsequent 7 weeks. Subjects experiencing a relapse (defined as an increase of at least 2 points on the CGI-S score at the end of Week 5) will discontinue treatment.

Efficacy and the effect of NFC-1 on individual symptoms will be assessed using CGI-I, CGI-S, ADHD rating scale score, the Pediatric Anxiety Rating Scale (PARS), Aberrant Behavior Checklist (ABC), and the Childhood Autism Rating Scale 2 (CARSTM-2). The ABC test is a symptom checklist for assessing problem behaviors in individuals with mental retardation. It involves clinical assessment of the person's degree of mental retardation, medical status, and current medical condition and involves assessment of 58 specific symptoms to be conducted by parents, educators, psychologists, nurses or physicians with knowledge of the subject. Among the behaviors assessed are irritability/agitation, lethargy/social withdrawal, stereotypic behavior, hyperactivity/noncompliance, and inappropriate speech. PARS is a clinician-rated scale of anxiety symptoms in pediatric subjects consisting of a list of 50 anxiety related symptoms. Each of the 50 items is scored on a scale of 0 to 5 with 0 indicating no symptoms and 5 indicating severe symptoms. The CARSTM-2 rating scale is a question-based scale that helps to assess symptoms of childhood autism. The scale is given in points of 1 for normal, 2 for mildly abnormal, 3 for moderately abnormal, and 4 for severely abnormal. The questionnaire assesses 15 items such as relating to people, imitation, emotional response, adaptation to change, visual response, listening response, fear/nervousness, verbal and non-verbal communication, and activity level. Scores range from 15 to 60, depending on the score for each item (1-4).

Example 4: Blind Screen of Biorepository Samples for mGluR Network CNVs and Link to ADHD Diagnosis A total of 3445 biorepository samples from the biorepository at the Center for Applied Genomics at Children's Hospital of Philadelphia having records of psychiatric evaluation were studied to determine how many of the samples have one or more CNVs in a Tier 1 or 2 mGluR network gene. The genotype tester/analyzer was not aware of the subject's psychiatric diagnosis while performing the CNV analysis. A goal of the study was to estimate the predictive value of CNVs in mGluR network genes by analyzing how many of the CNV positive samples had been previously confirmed from the accompanying psychiatric evaluation data to have ADHD. Of the 3445 samples, 155 were confirmed to have at least one CNV in a Tier 1 or Tier 2 mGluR network gene, or about 4.5%. Of the 155 having a CNV in a Tier 1 or 2 mGluR network gene, 138 were previously confirmed to have ADHD, whereas there were no such records for the remaining 17 subjects. In addition, about 60% of the 138 ADHD subjects also had co-morbid anxiety symptoms.

Of the 17 subjects for whom there were no records, 14 families were successfully contacted and questioned as to whether the subject had been diagnosed with ADHD. 13 of the 14 families confirmed that the subject indeed had been diagnosed with ADHD. Note that one of the 13 had Down Syndrome, and was considered negative for ADHD for purposes of this study. Thus, overall, of the 155 subjects with at least on CNV in an mGluR network gene, 138+12 subjects (150), or about 97%, also had been diagnosed with ADHD, while there was no data for 3 of the remaining 5 subjects. These data indicate that presence of a CNV in a Tier 1 or 2 mGluR network gene may be a powerful indicator of ADHD in pediatric subjects.

Example 5: Study of Phenotypes Associated with mGluR Network CNVs

A total of 1,000 ADHD patients aged 6-17 years were enrolled in a trial to consider phenotypes that may be associated with CNVs in Tier 1 or 2 mGluR network genes. Study sites collected saliva for a DNA sample. Each DNA sample was then subjected to DNA extraction, genetic sequencing, and biobanking of DNA.

Genetic sequencing results together with medical history were used to evaluate genotype (based on genetic sequencing) and phenotype (based on interviews conducted by a clinician with the subject's parent(s)/guardian(s)). Subjects had ADHD as defined by the Diagnostic and Statistical Manual of Mental Disorders, 5th Edition (DSM-V).

A single clinician, blinded to the genotype data, provided a series of questions related to potential behavioral or health phenotypes to the parent(s) or legal guardian(s) of the subjects. For each individual phenotype, the parent/guardian was asked: "Is this a current concern" and a Yes or No answer was collected. The clinician determined the frequency of Yes and No responses to generate phenotype data.

The study found that prevalence of anger control as a current concern was 58.9% in ADHD subjects with a Tier 1 or 2 mGluR network gene CNV but only 47.4% in ADHD subjects without such an mGluR network gene CNV. This difference was statistically significant (odds ratio of 1.59, P=0.003). This odds ratio of greater than 1 implies a higher prevalence of current anger control concerns in ADHD subjects who had a Tier 1 or 2 mGluR network gene CNV versus those without such a CNV.

The prevalence of disruptive behavior as a current concern for parents was 57.1% in ADHD subjects with a Tier 1 or 2 mGluR network gene CNV and 43.9% in ADHD subjects without such an mGluR network gene CNV. This difference was also statistically significant (odds ratio of 1.70, P<0.001), indicating a higher prevalence of current disruptive behavior concerns in ADHD subjects who also had an mGluR network gene mutation versus those without a mutation.

Example 6: Copy Number Variation in mGluR Network Genes in ADHD Subjects with Co-Morbid Disorders Samples from 2707 known ADHD pediatric subjects (mean age of about 10-10.5 years) were genotyped on 550/610 Illumina chips to determine if they have one or more CNVs in Tier 1 or Tier 2 genes. The 2707 subjects included 759 females and 1778 males of African American or white ethnicity (1063 and 1483, respectively). 430 of the 2707 subjects (16.9%) had at least one CNV in an mGluR Tier 1 or Tier 2 gene.

The 2707 subjects' records were also checked to determine if they had co-morbid diagnoses according to the World Health Organization International Classification of Diseases 9th Edition (ICD-9). Of the 2707 subjects, 1902 (about 70%) had comorbidities while 805 did not. Of those 1902 subjects with comorbidities, about 30% had more than one comorbidity, and about 20% had two or more, while smaller percentages had larger numbers of comorbidities.

The most prevalent comorbidities, each occurring in more than 100 of the subjects, are listed in Table 10. The table lists the comorbidities by ICD-9 code and provides the number of cases among the 2707 subjects (column titled "N") and name for each co-morbid condition or disorder.

TABLE 10

The most prevalent comorbidities

| ICD-9 Code | N | Name |
|---|---|---|
| N_299.00 | 342 | Autistic disorder, current or active state |
| N_299.80 | 267 | Other specified pervasive developmental disorders, current or active state |
| N_299.90 | 179 | Unspecified pervasive developmental disorder, current or active state |
| N_300.00 | 407 | Anxiety state unspecified |
| N_311 | 244 | Depressive disorder not elsewhere classified |
| N_312.9 | 568 | Unspecified disturbance of conduct |
| N_313.81 | 313 | Oppositional defiant disorder (ODD) |
| N_314.9 | 120 | Unspecified hyperkinetic syndrome of childhood |
| N_315.2 | 320 | Other specific developmental learning difficulties |
| N_315.31 | 189 | Expressive language disorder |
| N_315.32 | 157 | Mixed receptive-expressive language disorder |
| N_315.39 | 327 | Other developmental speech disorder |
| N_315.4 | 116 | Developmental coordination disorder |
| N_315.5 | 160 | Mixed development disorder |
| N_315.8 | 398 | Other specified delays in development |
| N_315.9 | 479 | Unspecified delay in development |
| N_319 | 110 | Unspecified intellectual disabilities |

The comorbidies in Table 10 tend to cluster into a few different groups: disorders related to anxiety, depression, or mood; prevalent developmental disorders; less prevalent developmental disorders; and autism and related disorders.

The genotype data and the comorbidity data were then combined to determine how many of the subjects with CNVs in Tier 1 or 2 mGluR network genes also had comorbidities. It was found that 316 of the subjects with such a CNV also had at least one comorbidity (about 18% of the CNV-positive subjects or about 12% of the total subjects) while 114 of the subjects without a Tier 1 or 2 mGluR network gene CNV had at least one comorbidity (about 15% of the CNV-negative subjects or about 4% of the total subjects). This difference showed a P value of 0.118. Thus, comorbidities tended to be more common in CNV-positive than in CNV-negative subjects overall.

When only subjects identifying as white ethnicity are considered, there was a highly significant correlation between mGluR CNVs and ADHD comorbidities. Specifically, 218 of 1483 subjects had at least one CNV in a Tier 1 or 2 mGluR network gene, and, of those 218 subjects, 169 also had a comorbidity whereas 49 did not. That difference showed a P value of 0.004.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method of treating 22q deletion and/or duplication syndrome in a subject comprising administering an effective amount of fasoracetam to a subject with 22q deletion and/or duplication syndrome, thereby treating 22q deletion and/or duplication syndrome, wherein the subject has at least one of oppositional defiant disorder (ODD), anxiety disorder, conduct disorder, Tourette's syndrome, autism, difficulty controlling anger, disruptive behavior, a mood disorder, a phobia, obsessive compulsive disorder (OCD), dermatillomania, a developmental disorder, or a movement disorder.

2. A method of treating 22q deletion and/or duplication syndrome in a subject comprising administering an effective amount of fasoracetam to a subject with 22q deletion and/or duplication syndrome, thereby treating 22q deletion and/or duplication syndrome, wherein the subject does not have at least one of oppositional defiant disorder (ODD), anxiety disorder, conduct disorder, Tourette's syndrome, autism, difficulty controlling anger, disruptive behavior, a mood disorder, a phobia, obsessive compulsive disorder (OCD), dermatillomania, a developmental disorder, or a movement disorder.

3. The method of claim 2, wherein the subject has ADHD.

4. The method of claim 1, wherein the subject has ODD.

5. The method of claim 4, wherein the method treats ODD in the subject.

6. The method of claim 1, wherein the step of administering an effective amount of fasoracetam to a subject with 22q deletion and/or duplication syndrome is preceded by detecting, in a sample obtained from the subject, the presence of a deletion or duplication at 22q11.2 and/or the presence of a genetic alteration in RANBP1.

7. The method of claim 1, wherein the subject does not have a copy number variation (CNV) or single nucleotide variation (SNV) in one or more of GRM1, GRM2, GRM3, GRM4, GRM5, GRM6, GRM7 or GRM8.

8. The method claim 1, wherein the fasoracetam is fasoracetam monohydrate.

9. The method of claim 1, wherein the subject has a genetic alteration.

10. The method of claim 1, wherein the subject has a deletion or a duplication at 22q11.2.

11. The method of claim 1, wherein the subject has a genetic alteration in at least one of a Tier 1, Tier 2, or Tier 3 metabotropic glutamate receptor (mGluR) network gene.

12. The method of claim 1, wherein the subject has attention deficit hyperactivity disorder (ADHD).

13. The method of claim 1, wherein the subject is a pediatric or adolescent subject.

14. The method of claim 1, wherein the subject is an adult subject.

15. The method of claim 1, wherein the fasoracetam is administered at a dose of 50-400 mg, and wherein the dose is administered once, twice, or three times daily.

16. The method of claim 1, wherein the fasoracetam is administered in combination with at least one of:
(i) a stimulant,
(ii) a nonstimulant,
(iii) an antidepressant,
(iv) an anxiolytic, (v) an anti-psychotic, and
(vi) a beta blocker.

17. The method of claim 1, wherein the fasoracetam is administered in combination with brain stimulation therapy selected from vagus nerve stimulation, repetitive transcranial magnetic stimulation, magnetic seizure therapy, and/or deep brain stimulation.

18. The method of claim 9, wherein the genetical alteration is at least one selected from the group consisting of a point mutation, insertion, deletion, or copy number variation (CNV) in RANBP1.

* * * * *